(12) United States Patent
Fischetti et al.

(10) Patent No.: US 10,590,403 B2
(45) Date of Patent: Mar. 17, 2020

(54) ACINETOBACTER LYSINS

(71) Applicant: The Rockefeller University, New York, NY (US)

(72) Inventors: Vincent Fischetti, New York, NY (US); Raymond Schuch, New York, NY (US); Rolf Lood, New York, NY (US); Benjamin Winer, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 15/321,905

(22) PCT Filed: Jun. 26, 2015

(86) PCT No.: PCT/US2015/037962
§ 371 (c)(1),
(2) Date: Dec. 23, 2016

(87) PCT Pub. No.: WO2015/200783
PCT Pub. Date: Dec. 30, 2015

(65) Prior Publication Data
US 2017/0130214 A1  May 11, 2017

Related U.S. Application Data

(60) Provisional application No. 62/017,618, filed on Jun. 26, 2014.

(51) Int. Cl.
| | |
|---|---|
| *A61K 9/00* | (2006.01) |
| *A61K 38/00* | (2006.01) |
| *A61K 47/64* | (2017.01) |
| *A61K 38/16* | (2006.01) |
| *A61K 38/47* | (2006.01) |
| *C12N 9/96* | (2006.01) |
| *C12N 9/88* | (2006.01) |
| *C12N 9/24* | (2006.01) |
| *A61L 2/16* | (2006.01) |
| *A61L 29/04* | (2006.01) |
| *A61L 29/08* | (2006.01) |
| *A61L 29/16* | (2006.01) |

(52) U.S. Cl.
CPC .......... *C12N 9/2402* (2013.01); *A61K 9/0014* (2013.01); *A61K 9/0019* (2013.01); *A61K 38/162* (2013.01); *A61K 38/47* (2013.01); *A61K 47/64* (2017.08); *A61L 2/16* (2013.01); *A61L 29/043* (2013.01); *A61L 29/085* (2013.01); *A61L 29/16* (2013.01); *C12N 9/88* (2013.01); *C12N 9/96* (2013.01); *A61K 38/00* (2013.01); *A61L 2202/24* (2013.01); *A61L 2300/254* (2013.01); *A61L 2300/406* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,997,862 A * | 12/1999 | Fischetti | ................ | C12N 9/503 424/434 |
| 6,238,661 B1 * | 5/2001 | Fischetti | ................ | C12N 9/503 424/431 |
| 6,562,958 B1 * | 5/2003 | Breton | ................... | C07K 14/22 536/23.1 |
| 7,144,712 B2 * | 12/2006 | Milich | ................... | A61K 39/12 435/69.3 |
| 7,320,795 B2 * | 1/2008 | Milich | ................ | A61K 39/015 424/189.1 |
| 7,604,975 B2 * | 10/2009 | Lee | .......................... | C12N 9/52 435/212 |
| 7,811,576 B2 * | 10/2010 | Milich | ................ | A61K 39/015 424/189.1 |
| 7,883,843 B2 * | 2/2011 | Milich | ................ | A61K 39/385 424/199.1 |
| 9,005,579 B2 * | 4/2015 | Nowinski | ............... | A61K 31/43 424/130.1 |
| 9,034,322 B2 * | 5/2015 | Fischetti | .............. | A61K 38/162 424/94.61 |
| 9,259,407 B2 * | 2/2016 | Baker, Jr. | .............. | A61K 9/1075 |
| 9,499,594 B2 * | 11/2016 | Schuch | ................... | C12N 9/503 |
| 9,707,279 B2 * | 7/2017 | Collin | .................... | A61K 38/47 |
| 9,731,010 B2 * | 8/2017 | Nowinski | ............... | A61K 31/43 |
| 9,872,843 B2 * | 1/2018 | Myntti | ................. | A61K 31/194 |
| 9,999,635 B2 * | 6/2018 | Sampson | ............... | A61K 33/20 |

(Continued)

FOREIGN PATENT DOCUMENTS

| | | |
|---|---|---|
| CN | 102940874 A | 2/2013 |
| RU | 2325398 C2 | 5/2008 |

(Continued)

OTHER PUBLICATIONS

Fischetti et al, Current Opinion in Microbiology, 2008, 11:393-400, available online Oct. 14, 2008 (Year: 2008).*
Fischetti, International Journal of Medical Microbiology, 2010, 300:357-362, (Year: 2010).*
Lood et al, Antimicrob. Agents Chemother., Apr. 2015, 59/4:1983-1991. available online Jan. 20, 2015 (Year: 2015).*
Oliveira et al, Trends in Food Science and Technology, 2012, 28:103-115 (Year: 2012).*
Raz et al, PLoS One, 2015 , 10/10:e0140784 , published:Oct. 20, 2015 (Year: 2015).*
Thandar et al, Antimicrobial Agents and Chemotherapy, May 2016, 60/5:2671-2679. available online: Feb. 8, 2016 (Year: 2016).*

(Continued)

*Primary Examiner* — Nita M. Minnifield
(74) *Attorney, Agent, or Firm* — Honigman LLP; Cynthia M. Bott; Jonathan P. O'Brien

(57) ABSTRACT

*Acinetobacter* lysin polypeptides and variants peptides with killing activity against gram negative bacteria. Methods for treating bacterial infections or bacterial colonization using *Acinetobacter* lysin polypeptides.

13 Claims, 40 Drawing Sheets

Specification includes a Sequence Listing.

(56) References Cited

U.S. PATENT DOCUMENTS

| | | | |
|---|---|---|---|
| 2003/0113298 A1* | 6/2003 | Fischetti | A61K 38/46 424/93.6 |
| 2004/0146984 A1* | 7/2004 | Lee | C12N 9/52 435/69.3 |
| 2005/0025781 A1* | 2/2005 | Milich | A61K 39/015 424/189.1 |
| 2006/0292135 A1* | 12/2006 | Loomis | C12Y 403/01024 424/94.1 |
| 2007/0077235 A1* | 4/2007 | Loomis | A61K 38/46 424/93.6 |
| 2010/0172918 A1 | 7/2010 | Yoon et al. | |
| 2011/0262508 A1* | 10/2011 | Watt | C07K 14/00 424/405 |
| 2012/0122766 A1 | 5/2012 | Gemba et al. | |
| 2013/0045211 A1* | 2/2013 | Nowinski | A61K 31/43 424/150.1 |
| 2014/0073639 A1* | 3/2014 | Fischetti | C07D 233/86 514/234.2 |
| 2014/0079671 A1* | 3/2014 | Da Costa Garcia | A61K 35/76 424/93.6 |
| 2015/0267185 A1* | 9/2015 | Fischetti | A61K 38/162 424/94.61 |
| 2015/0290299 A1* | 10/2015 | Schuch | C12N 9/503 424/94.61 |
| 2015/0306218 A1* | 10/2015 | Nowinski | A61K 31/43 424/146.1 |
| 2017/0127683 A1* | 5/2017 | Schuch | A01N 63/00 |
| 2017/0130214 A1* | 5/2017 | Fischetti | C12N 9/2402 |
| 2017/0298334 A1* | 10/2017 | Fischetti | A61K 38/162 |
| 2018/0369176 A1* | 12/2018 | Myntti | A61K 9/0014 |
| 2019/0070269 A1* | 3/2019 | Schuch | A61K 38/12 |
| 2019/0231863 A1* | 8/2019 | Mulder | A61K 47/10 |
| 2019/0247494 A1* | 8/2019 | Zhang | A61K 39/29 |

FOREIGN PATENT DOCUMENTS

| | | | |
|---|---|---|---|
| RU | 2468033 C2 | 11/2012 | |
| WO | 2001004328 A1 | 1/2001 | |
| WO | 2008006125 A1 | 1/2008 | |
| WO | WO-2011084882 A2 * | 7/2011 | A61K 31/43 |
| WO | 2012036580 A2 | 3/2012 | |
| WO | WO-2012145630 A2 * | 10/2012 | A61K 38/162 |
| WO | WO-2013170015 A1 * | 11/2013 | C12N 9/503 |
| WO | WO-2014124047 A1 * | 8/2014 | A61K 39/12 |
| WO | WO-2015200783 A2 * | 12/2015 | C12N 9/88 |
| WO | WO-2017049233 A2 * | 3/2017 | A61K 38/12 |
| WO | WO-2017049242 A2 * | 3/2017 | A61K 38/12 |
| WO | WO-2017197227 A1 * | 11/2017 | A61K 38/12 |

OTHER PUBLICATIONS

Briers et al, mBio, Jul./Aug. 2014, 5/4:e01379-14 published Jul. 1, 2014 (Year: 2014).*

Gopal et al Antimicrobial Agents and Chemotherapy, Mar. 2014. 58/3:1622-1629, published ahead of print Dec. 23, 2013 (Year: 2014).*

Greenspan et al, Nature Biotechnology, 1999, 7:936-937 (Year: 1999).*

Michalopoulos et al, Expert Opinion on Pharmacotherapy, 2010, 11/5:779-788, published online: Mar. 9, 2010 (Year: 2010).*

Vila et al, Expert Opinion Pharmacother., 2008, 9/4:587-599 (Year: 2008).*

Wong et al, Clinical Microbiology Reviews, Jan. 2017, 30/1:409-447, published Dec. 14, 2016 (Year: 2016).*

Burgess et al., JCB, 1990, 111:2129-2138 (Year: 1990).*

Lazar et al., Molecular and Cellular Biology, 1988, 8:1247-1252 (Year: 1988).*

Thomas E. Creighton, "Proteins: Structures and Molecular Properties, 1984", (pp. 314-315) (Year: 1984).*

Blythe et al, Protein Science, 2005, 14:246-248 (Year: 2005).*

Houghten et al (Vaccine 86, 1986, pp. 21-25) (Year: 1986).*

Bixler et al, Synthetic Vaccines, vol. 1, 1987, pp. 39-71 (Year: 1987).*

Bowie et al., Science, 1990, vol. 247, pp. 1306-1310 (Year: 1990).*

Kumar et al. PNAS Feb. 1991, 87:1337-1341 (Year: 1991).*

A0A009YLPO_ACIBA, Lysozyme Gene J500_0845 from Acinetobacter baumannii 479375, Uniprot Accession No. A0A009YLPO ACIBA, Jun. 11, 2014 [online]. [Retrieved on Nov. 2, 2015]. Retrieved from the internet <URL: http://www.uniprot.org/uniprot/A0A009YLP0> whole doc.

PCT International Search Report and Written Opinion, App. No. PCT/US2015/03792, dated Dec. 14, 2015, 5 pgs.

EP Supplementary Partial Search Report for EP 15812120.2/3164146, dated Nov. 15, 2017, 10 pages.

Lesho, Emil et al., "Emergence of colistin-resistance in extremely drug-resistant Acinetobacter baumannii containing a novel pmrCAB operon during colistin therapy of wound infections.", The Journal of Infectious Diseases, Oct. 2013, pp. 1142-1151, vol. 208, NR. 7.

Lesho, Emil et al., "Emergence of colistin-resistance in extremely drug-resistant Acinetobacter baumannii containing a novel pmrCAB operon during colistin therapy of wound infections,", Database Accession No. R4L440, Oct. 2013, Abstract Only, 1 pg.

Lood, Rolf et al., "Novel Phage Lysin Capable of Killing the Multidrug-Resistant Gram-Negative Bacterium Acinetobacter baumannii in a Mouse Bacteremia Model", Database Accession No. A0A0B5KND4, May 2015 Abstract Only, 1 pg.

Lood, Rolf et al., "Novel Phage Lysin Capable of Killing the Multidrug-Resistant Gram-Negative Bacterium Acinetobacter baumannii in a Mouse Bacteremia Model", Database Accession No. A0A0B5KZH1, May 2015, Abstract Only, 1 pg.

RU2017102306 Search Report dated Feb. 22, 2019, 4 pgs with English translation.

Chen, H. L. et al., "Identification of a novel antimicrobial peptide from human hepatitis B virus core protein arginine-rich domain (ARD).", PLoS Pathogens, 2013, vol. 9, No. 6, e1003425, 15 pgs.

GenBank: EXD36936.1, "phage lysozyme family protein [Acinetobacter sp. 479375]," Accession: EXD36936, NCBI Sequence Revision History [online], Feb. 25, 2014 uploaded, NCBI, <URL: https://www.ncbi.nlm.nih.gov/protein/588055426?sat=37&satkey=176914986>, 1 pg.

* cited by examiner

FIG. 4

ClustalW (v1.83) multiple sequence alignment

21 Sequences Aligned        Processing time: 1.8 seconds
Gaps Inserted = 540         Conserved Identities = 1
Score = 0

Pairwise Alignment Mode: Slow
Pairwise Alignment Parameters:
    Open Gap Penalty = 10.0   Extend Gap Penalty = 5.0

Multiple Alignment Parameters:
    Open Gap Penalty = 10.0   Extend Gap Penalty = 5.0
    Delay Divergent = 40%     Transitions: Weighted

```
F376    1 ------------------------------------------------------------  0
F311    1 ------------------------------------------------------------  0
F328    1 ------------------------------------------------------------  0
F324    1 ------------------------------------------------------------  0
F347    1 ------------------------------------------------------------  0
F351    1 ------------------------------------------------------------  0
F344    1 ------------------------------------------------------------  0
F340    1 ------------------------------------------------------------  0
F338    1 ATGAAGTTAATTGAAAACAATGCTTGGCAGTATCTATCTGTTAAGTTACCCGCCGTAGGT 60
F336    1 ------------------------------------------------------------  0
F334    1 ------------------------------------------------------------  0
F332    1 ATGAAGTTAATTGAAAACAATGCTTGGCAGTATCTATCTGTCAAGTTACCCGCCGTAGGT 60
F330    1 ------------------CTGGATCCGGTGATGACGAT--GACAAG---CTCGCCCT---T 35
F307    1 ------------------------------------------------------------  0
F309    1 ------------------------------------------------------------  0
F303    1 ------------------------------------------------------------  0
F301    1 ------------------------------------------------------------  0
F320    1 ------------------------------------------------------------  0
F306    1 ------------------------------------------------------------  0
F321    1 ------------------------------------------------------------  0
F315    1 ------------------------------------------------------------  0
F376    1 ------------------------------------------------------------  0
F311    1 ------------------------------------------------------------  0
```

FIG. 4 Cont.

```
F328    1 ---------------------------------------------------------------    0
F324    1 ---------------------------------------------------------------    0
F347    1 ---------------------------------------------------------------    0
F351    1 --------------------------------------------------------------C    1
F344    1 ---------------------------------------------------------------    0
F340    1 ---------------------------------------------------------------    0
F338   61 GCATTCATCATGCT-AATTTTATTGCCAGCACTACAATGGGGTGTTGATTATGAAGTTAT  119
F336    1 ---------------------------------------------------------------    0
F334    1 ---------------------------------------------------------------    0
F332   61 GCATTCATCATGCT-AATTTTATTGCCAGCACTACAATGGGGTGTTGATTATGAAGTTAT  119
F330   36 CCACAACTCGAGCCGAATTTTATTGCCAGCACTACAATGGGGTGTTGATTATGAAGTTAT   95
F307    1 ---------------------------------------------------------------    0
F309    1 ---------------------------------------------------------------    0
F303    1 ---------------------------------------------------------------    0
F301    1 ---------------------------------------------------------------    0
F320    1 ---------------------------------------------------------------    0
F306    1 ---------------------------------------------------------------    0
F321    1 ---------------------------------------------------------------    0
F315    1 ---------------------------------------------------------------    0
F376    1 --------------------------------TTAAGCCTCTGAAACACTCGTAACAGA   27
F311    1 ---------------------------------------------------------------    0
F328    1 ------------------------------------------------------CTAGCCGAT    9
F324    1 ---------------ATGAAAAT-TGAACAATATCTTGATGATT------TGATTAAACGC   39
F347    1 ---------------------------------------------------------TCACTGC    7
F351    2 TGAAGGAAACCGAAATGAATAT-TGAAAAATATCTTGATGAAT------TAATTAAGCGT   54
F344    1 ------------------------------------------------TCATATAAC-AAC   12
F340    1 --------------------------------TTAAGCCTCTGAAACACTCGTAACAGA   27
F338  120 TCCTGAAAAATATCATGCATTTGTTACTGGTACTTTGATGCTTGTTCTGTCATGGATTGG  179
F336    1 --------------------------------TTAGGCTTCCAAAACCCTAGTAGCTGT   27
F334    1 --------------------------------TTAGGCTTCCAAAACCCTAGTAGCTGT   27
F332  120 TCCTGAAAAATATCATGCATTTGTTACTGGTACTTTGATGCTTGTTCTGTCATGGATTGG  179
F330   96 TCCTGAAAAATATCATGCATTTGTTACTGGTACTTTGATGCTTGTTCTGTCATGGATTGG  155
F307    1 ---------------------------------------------------------GT    2
F309    1 ---------------ATGAAAAT-TGAACAATATCTTGATGATT------TGATTAAACGC   39
F303    1 ------------------------------------------------------CTAGCCGAT    9
F301    1 ------------------------------------------------------CTAGCCGAT    9
F320    1 ------------------------------------------------------CTAGCCGAT    9
```

FIG. 4 Cont.

```
F306    1 ------------------------------ATGTCAAACAAGACTAAAATCATAGT  26
F321    1 --------------ATGAAAAT-TGAACAATATCTTGATGATT------TGATTAAACGC  39
F315    1 ------------------------------------------------TCACTGC   7
F376   28 AACGATTTTTAGGACTGGTAAATCGTATCGGTGAGCAG---CTGGTTTACTTGTTTTGCC  84
F311    1 ---------------------------------------TCAT-TTTAA-AAA  12
F328   10 CCGGTTAGCGATCCAGCCATAAAAAAACTGCTCTTGGC---TTTTATTACGTTCAC-AGA  65
F324   40 GAAGGCGGTTATGTAA--ATAATCCAGTGGATCGAGG---AGGTGCTACCAAATAC-GGT  93
F347    8 GCTCCTATACATTT-------TGCGTGTCGTT--CTAC---TTGTCTGGTCCAGAC-GCC  54
F351   55 GAAGGCGGGTATGTAA--ATAACCCAGCTGATCGGGG---CGGTGCAACTAAATAT-GGC 108
F344   13 TCGATTGGCGATCCAACCATAGAAAAACTGTTCCTGGC---TAGGATTGCGTTCAC-AGA  68
F340   28 AACGATTTTTAGGACTGGTAAATCGTATCGGTGAGCAG---CTGGTTTACTTGTTTTGCC  84
F338  180 AAAGAAAATTTCTCAACCACGACTTAATGGCCCGCAATTAACAGGCCAGTTAGTA-GGG 237
F336   28 TACGCCTTTTAATTGTGGCAATGTATAACGCTTACTTG---CTGGTTGAGTTGTACGACC  84
F334   28 TACGCCTTTTAATTGTGGCAATGTATAACGCTTACCTG---CTGGTTGAGTTGTACGACC  84
F332  180 AAAGAAAATTTCTCAACCACGACTTAATGGCCCGCAATTAACAGGCCAGTTAGTA-GGG 237
F330  156 AAAGAAAATTTCTCAACCACGACTTAATGGCCCGCAATTAACAGGCCAGTTAGTA-GGG 213
F307    3 GAAAACAAGTAACCCA--GGAGTGGATTTAATCAAA-----------GGCTTTGAA-GGT  48
F309   40 GAAGGCGGTTATGTAA--ATAATCCAGTAGATCGAGG---AGGTGCTACCAAATAC-GGT  93
F303   10 CCGGTTAGCAATCCAGCCATAGAAGAATTGCTCTTGCT---TAGGATTACGCTCAC-AAA  65
F301   10 CCGGTTAGCGATCCAGCCATAAAAAAACTGCTCTTGGC---TTTTATTACGTTCAC-AGA  65
F320   10 CCGGTTAGCAATCCAGCCATAGAAGAATTGCTCTTGCT---TGGGATTACGCTCAC-AAA  65
F306   27 AACAACATTAAGCGCA--TCAGCGCTTTTTTTTGCATC---TTTAATTGGCTATGAG-GGG  81
F321   40 GAAGGTGGTTATGTAA--ATAATCCAGTAGATCGAGG---AGGTGCTACCAAATAC-GGT  93
F315    8 ACCGCCATACACTT-------GCTATAACAAT--CTTG---TTGGCGTGTCCAGAC-ACC  54
F376   85 ATACCACATAAAGGCTTCAAAAGCCGAAACGTCATATACTGCAAAACAAACTT-TATTTG 143
F311   13 T----AACTCCATTTCAGCTTTGCGACGT-TTCACCAGTCCTGC-CAATACACGACCGCC  66
F328   66 TTT-CAATGTATCGTTGGCCTTGCATAATATTTAACACGCGCAC-TAAGACCTTTTCGCC 123
F324   94 AT--TACTGAAGCTGTAGCACGTGAAAACGGCTATAAGGGCAAT-ATGAA-AGATTTGC 148
F347   55 ATAACACCCGTTTTTACGAA---CAGAGCAATCGCGCTTTGCA-ACGTACTTATATTTA 109
F351  109 AT--CACACAAGCTGTTGCGCGTGAAAATGGCTGGAATGGCAAT-ATGAA-AGATTTGC 163
F344   69 TTT-CAATGTAACGTTGCCCTTGCATGATATTAAGAACACGCAC-CAGGACTTTTTCGCC 126
F340   85 ATACCACATAAAGGCTTCAAAAGCCGAAACGTCATATACTGCAAAACAAACTT-TATTTG 143
F338  238 AT--CAATTCT-TTATTGAATATCCCAACACCAACAAAGCCTG-ATGAATTAGCTTGGA 292
F336   85 ATACCATCTGAATTCTTGAAAGTCAGAGTCATTATAAAGTGCATAACAAACTT-TATTTG 143
F334   85 ATACCATCTGAATTCTTGAAAGTCAGAGTCATTATAAAGTGCATAACAAACTT-TATTTG 143
F332  238 AT--CAATTCT-TTATTGAATATCCCAACACCAACAAAGCCTG-ATGAATTAGCTTGGA 292
F330  214 AT--CAATTCT-TTATTGAATATCCCAACACCAACAAAGCCTG-ATGAATTAGCTTGGA 268
```

FIG. 4 Cont.

```
F307   49 CTA-CGATTGA---AAGCC-TATGACGATGGTGTGGGCGTTTGG-ACCATTGGCTTTGGC 102
F309   94 AT--TACTGAAGCTGTAGCACGTGAAAACGGCTATAAGGGCAAT-ATGAA-AGATTTGC  148
F303   66 TTT-CGATATATCGCTGGCCTTGCATGATATTAAGAACTCGCAC-TAGGACTTTCTCACC 123
F301   66 TTT-CAATGTATCGTTGGCCTTGCATAATATTTAACACGCGCAC-TAAGACCTTTTCGCC 123
F320   66 TTT-CGATATATCGCTGGCCTTGCATGATATTAAGAACTCGCAC-TAGGACTTTCTCACC 123
F306   82 -TA-CAAATCA---AAGCCATATTTAGATAGCGCTAAAGTGGCA-ACGATTGGTATCGGA 135
F321   94 AT--TACTGAAGCTGTAGCACGTGAAAACGGCTATAAGGGCAAT-ATGAA-AGATTTGC  148
F315   55 ATAACAACCATTGGACCGAA---TCGAGCAATCACGCTTTGCA-ACATATTTGTATTTC  109
F376  144 ACTGATTACCACCTAAGCAAATTA-ATTTACCAGTAGGTGTTTTAC---CAACAACGAAA 199
F311   67 AGCTTTGTTCCATTTTGGGAATTCTGCTGCT-GCACCTTTATAGTCCTT-AGCATTTAAC 124
F328  124 TTCTTTGCCACGTTTGGCCAAGTAAGTTTTTAGAGCTCCTAAAGTGTTAGAACCATAAAC 183
F324  149 CTCTTGATGTGGCCAAA-GCAATTTA--TCGGAAACAGTACTGGA-TAGA-GCCAC-GTT 202
F347  110 AGTAAAGAGTCGCAAGCTGCTTTATATTGACCAGC-----CTTTA-----AATGCTTAAG 159
F351  164 CGCTTGATGTGGCCAAA-GCTATTTA--CAAGAAGCAATACTGGA-CAGC-TCCGC-GAT 217
F344  127 GTCTTTTCCACGCTTGGCCAGATAAGTTTTGAGTGCATTAAGAGTTGCTGGACCATAAAT 186
F340  144 ACTGATTACCACCTAAGCAAATTA-ATTTACCAGTGGGTGTTTTAC---CAACAACGAAA 199
F338  293 TTGCGGAAGCAAA-AAA-GCATCTTGGCCTTCAAGAAATACCTGG-TAAACAGCAT-AAC 348
F336  144 ACTGATTGCCTCCAAGGCATACTA-ACTTTCCAGACTTTTTGTCACGGCCAACTACAAAA 202
F334  144 ACTGATTGCCTCCAAGGCATACTA-ACTTTCCAGACTTTTTGTCACGGCCAACTACAAAA 202
F332  293 TTGCAGAAGCAAA-AAA-GCATCTTGGCCTTCAAGAAATACCTGG-TAAACAGCAT-AAC 348
F330  269 TTGCAGAAGCAAA-AAA-GCATCTTGGCCTTCAAGAAATACCTGG-TAAACAGCAT-AAC 324
F307  103 ACCATCAAATACCCGAACGGTGTGCGAGTCAAAAAAGGCGATA---CATGCACTGA-ATC 158
F309  149 CTCTTGATGTGGCCAAA-GCAATTTA--TCGGAAACAGTACTGGA-TAGA-GCCAC-GTT 202
F303  124 TTCTTTCCCACGTTTGGCCAAGTAAGTTTTGAGAGCTCCTAATGTGCTAGAACCATAAAC 183
F301  124 TTCTTTGCCACGTTTGGCCAAGTAAGTTTTTAGAGCTCCTAAAGTGTTAGAACCATAAAC 183
F320  124 TTCTTTCCCACGTTTGGCCAAGTAAGTTTTGAGAGCTCCTAATGTGCTAGAACCATAAAC 183
F306  136 TCCACTTCCTATGAAAACGGTACCAAGGTCAAAATGACTGACAAGCCGATTACAAA-AGA 194
F321  149 CTCTTGATGTGGCCAAA-GCAATTTA--TCGGAAACAGTACTGGA-TAGA-GCCAC-GTT 202
F315  110 AGTAATGAAGCACAAGCTTGCTTATATTGCCCTGC-----TTTGA-----GATTACGAAG 159
F376  200 GTTACATGGCCACCGCCCTCTCTTGATTTACCGCAACACACCCATAACAAGGCTTGTYT  259
F311  125 TTTTTTAGCAAAGTAGATTTGCTAAGATTGCCTTC-GCCTAAGT-TAT-AAGTGAATG-A 180
F328  184 GCCATCAACCTT-CAAGTCTGCATAACCAGCTTT--ACCTTGAT-TGTTAAGCAAGTTCA 239
F324  203 TTGATCAGGTTAATA---CTCTTAGCTCTGCAGT-------AGC-TG--AAGA------- 242
F347  160 CATTGATG------ATTT-TGCG-AATGTTGGCACACCGTATTGATACGTGAA---ATCA 208
F351  218 TTGACCAAGTAAATG---CTGTTTCTTCTGCAGT-------AGC-TG--AAGA------- 257
F344  187 TCCGTCAACTGT-TAAATCTGGCCAACCTGCTTT--ACCTTGGT-TATTCAGCAAATTTA 242
F340  200 GTTACATGGCCACCGCCCTCTCTTGATTTACCGCAACACACCCATAACAAGGCTTGTCT  259
```

FIG. 4 Cont.

```
F338  349 CCAACTATTTTAAAATGGCTCTCGGAGCTAAAGGCTTGGTGGGC-TG--ACGATGAAACG 405
F336  203 CAAACATGCCCACCACCCTTTCGAGTTTTAATAGCTACACAACCGTAAGCGGGTTTAGCT 262
F334  203 CAAACATGCCCACCACCCTTTCGAGTTTTAATAGCTACACAACCGTAAGCGGGTTTAGCT 262
F332  349 CCAACTATTTTAAAATGGCTCTCGGAGCTAAAGGCTTGGTGGGC-TG--ACGATGAAACG 405
F330  325 CCAACTATTTTAAAATGGCTCTCGGAGCTAAAGGCTTGGTGGGC-TG--ACGATGAAACG 381
F307  159 TCAAGCGGAAGAATA---CCTTCGCAA-TGACTT-------AGT-TG--TATTTGAAA-202
F309  203 TTGATCAGGTTAATA---CTCTTAGCTCTGCAGT-------AGC-TG--AAGA------- 242
F303  184 GCCATCAACCTT-CAAGTCTGCATAACCAGCTTT--ACCTTGAT-TGTTAAGCAAGTTCA 239
F301  184 GCCATCAACCTT-CAAGTCTGCATAACCAGCTTT--ACCTTGAT-TGTTAAGCAAGTTCA 239
F320  184 GCCATCAACCTT-CAAGTCTGCATAACCAGCTTT--ACCTTGAT-TGTTAAGCAAGTTCA 239
F306  195 ACGTGCTGTTCAA-A---TTGCCAAAGCTCACAT-------TGC-TA--AAGATGAGGTG 240
F321  203 TTGATCAGGTTAATA---CTCTTAGCTCTGCAGT-------AGC-TG--AAGA------- 242
F315  160 CATTGATG------AGCCGTTCC-AAT-TTGCTTGGCCATAGTTGTAAACAAA---GTCT 208
F376  260 AATTTGACTCCGCCTTCTTTGATGTATTC--AAGTGCGGCAT------ACCAGTTGAAAG 311
F311  181 GGCCAAAGCATCGAATTGGTTTTGATTAA-GTGGTACT----------TTCAC-CAAGC 227
F328  240 AAGCACGTTGTAAAAGTGGTTTTGCAAAG-TTGATACCACAG-------TTCACACCAGT 291
F324  243 ACTT----TTAGACACTGGT-GTGAACTG--TGGTATCAACT----TTGCAAAACCA--- 288
F347  209 AGGTA---TAGGTCATATTCAGTCTGTGA--TAATT---CGG------CT-----CGAGT 249
F351  258 GCTT----CTAGACACTGGT-GTGAATTG--CGGTACCGGAT----TTGCAAAACCT--- 303
F344  243 AAGCACGCTGTAAGAGTGGTTTTGCAAAT-CCGGTACCGCAA-------TTTACCCCAGT 294
F340  260 AATTTGACTCCGCCTTCTTTGATGTATTC--AAGTGCGGCAT------ACCAGTTGAAAG 311
F338  406 GCTTGGTGTGGGACCTTCGTTGCACATTGCTTGAAATCAGCTGGAATTGCTTATCCTAAG 465
F336  263 AATTT---TGTACCATAATTCACATAATC--CAATGCACGGT------ACCAATGCTTAG 311
F334  263 AATTT---TGTACCATAATTCACATAATC--CAATGCACGGT------ACCAATGCTTAG 311
F332  406 GCTTGGTGTGGGACCTTCGTTGCACATTGCTTGAAATCAGCTGGAATTGCTTATCCTAAG 465
F330  382 GCTTGGTGTGGGACCTTCGTTGCACATTGCTTGAAATCAGCTGGAATTGCTTATTCTAAG 441
F307  203 GCGC----TAT-CAATCGTTTGGTGAAAG--TTCCGCTTAAT-------CAAAACCA--- 245
F309  243 ACTT----TTAGACACTGGT-GTGAACTG--TGGTATCAACT----TTGCAAAACCA--- 288
F303  240 AAGCACGTTGTAAAAGTGGTTTTGCAAAG-TTGATACCACAG-------TTCACACCAGT 291
F301  240 AAGCACGTTGTAAAAGTGGTTTTGCAAAG-TTGATACCACAG-------TTCACACCAGT 291
F320  240 AAGCACGTTGTAAAAGTGGTTTTGCAAAG-TTGATACCACAG-------TTCACACCAGT 291
F306  241 GCAT----TTCGCAAGTCGTTGCAGGGCG--TGAGGCTAACT-------CAGACTGA--- 284
F321  243 ACTT----TTAGACACTGGT-GTGAACTG--TGGTATCAACT----TTGCAAAACCA--- 288
F315  209 AAGTA---CACATCATATTCAGTCTGAGT--TAGCCTCACGC------CCTGCAACGACT 257
F376  312 GATAA--AAGCCTGGTGGGGCCTTTGTTCC-TGATTT---ATAAGTTTTGGAACGCGAGT 365
F311  228 GATTG--ATAGCATTTTCAAATGCGACCAAGTCATTGCGAAGATATCCTTCTGCTTGAGA 285
F328  292 GTCTA--AAAGT-TCTTCAGCTACTGCAGAGCTAAGAGTATTAACCTGATCAAAACGTGG 348
```

FIG. 4 Cont.

```
F324  289 CTTTT--ACAACGTGCTTTGAACTTGCTTAACAATCAAGGTAAAGCTGGTTATGCAG--A 344
F347  250 TGTGG--AAGGCAG--------------------------------------------- 261
F351  304 CTTTT--ACAACGAGCTTTGAACTTGCTTAATAACCAAGGTAAAGCTGGATATGCAG--A 359
F344  295 ATCTA--AAAGC-TCTTCAGCAACTAACGAGCTAATTACATTCACTTGATCAAATCGCGG 351
F340  312 GATAA--AAGCCTGGTGGGGCCTTTGTTCC-TGATTT---ATAAGTTTTGGAACGCGAGT 365
F338  466 CATTG--GTACCGTGCATTGGATTATGTGAATTAT-GGTACAAAATTAGCTAAACCC--G 520
F336  312 GATAAGCAATTCCAGCTGATTTCAAGCAATGTGCAAC---GAAGGTCCCACACCAAGCCG 368
F334  312 GATAAGCAATTCCAGCTGATTTCAAGCAATGTGCAAC---GAAGGTCCCACACCAAGCCG 368
F332  466 CATTG--GTACCGTGCATTGGATTATGTGAATTAT-GGTACAAAATTAGCTAAACCC--G 520
F330  442 CATTG--GTACCGTGCATTGGATTATGTGAATTAT-GGTACAAAATTAGCTAAACCC--G 496
F307  246 -ATTC--GATGCTTTGGCCTCATTCACTTA-CAACCTTGGTGAGGGCAATCTTAGTA--T 299
F309  289 CTTTT--ACAACGTGCTTTGAACTTGCTTAACAATCAAGGTAAAGCTGGTTATACAG--A 344
F303  292 GTCTA--AAAGT-TCTTCAGCTACTGCAGAGCTAAGAGTATTAACCTGATCAAAACGTGG 348
F301  292 GTCTA--AAAGT-TCTTCAGCTACTGCAGAGCTAAGAGTATTAACCTGATCAAAACGTGG 348
F320  292 GTCTA--AAAGT-TCTTCAGCTACTGCAGAGCTAAGAGTATTAACCTGATCAAAACGTGG 348
F306  285 -ATAT--GATGTGTACTTAGACTTTGTTTA-CAACTATGGCCAAGCAAATTGGAACG--G 338
F321  289 CTTTT--ACAACGTGCTTTGAACTTGCTTAACAATCAAGGTAAAGCTGGTTATGCAG--A 344
F315  258 TGCGA--AATGCCACCTCATCTTTAGCAATGTGAGCTTTGGCAATTTGAACAGCACGTTC 315
F376  366 TTACACT-TCCTCTTTGAAATCCCGCCGTTTGG-AGA--CAGTGCGCAACGAATGTTCCG 421
F311  286 CTCAGTGCATATATCGCCTTTTTTGACACGC----ACTCCATTAGG------ATATTTAA 335
F328  349 CTCTATCCA-GTACTGTTTCCGATAAATTGCTTTGGCCACATCAAGAGGCAAATCTTTCA 407
F324  345 CTTGAAGGTTG-ATGGCGTTT-ATGGTTCTA---ACACTT--TAGGA-----GCTCTAAA 392
F347  262 ----------------------------------------------------------- 261
F351  360 TTTAGAGGTTG-ATGGTGTTT-ATGGCTCAG---CAACGC--TAGGT-----GCCCTTAA 407
F344  352 ATCTGTCCA-ATACTGCTTTTTATAAATGGCTTTGGCCACATCAAGCGGTAAATCTTTCA 410
F340  366 TTACACT-TCCTCTTTGAAATCCCGCCGTTTGG-AGA--CAGTGCGCAACGAATGTTCCG 421
F338  521 CTT-ACGGTTGTGTAGCTATT-AAAACTCGA---AAGGGTGGTGGGC-----ATGTTTGT 570
F336  369 TTTCATCGTCAGCCCACCAAGCCTTTAGCTCCG-AGAGCCATTTTAAAATAGTTGGGTTA 427
F334  369 TTTCATCGTCAGCCCACCAAGCCTTTAGCTCCG-AGAGCCATTTTAAAATAGTTGGGTTA 427
F332  521 CTT-ACGGTTGTGTAGCTATT-AAAACTCGA---AAGGGTGGTGGGC-----ATGTTTGT 570
F330  497 CTT-ACGGTTGTGTAGCTATT-AAAACTCGA---AAGGGTGGTGGGC-----GTGTTTGT 546
F307  300 ATC-AACTTTGCTAAAAAAGC-TTAATGCCA---AAGACTA-TAAAG-----GTGCTGCA 348
F309  345 CTTGAAGGTTG-ATGGCGTTT-ATGGTTCTA---GCACAT--TAGGA-----GCTCTCAA 392
F303  349 CTCTATCCA-GTACTGTTTCCGATAAATTGCTTTGGCCACATCAAGAGGCAAATCTTTCA 407
F301  349 CTCTATCCA-GTACTGTTTCCGATAAATTGCTTTGGCCACATCAAGAGGCAAATCTTTCA 407
F320  349 CTCTATCCA-GTACTGTTTCCGATAAATTGCTTTGGCCACATCAAGAGGCAAATCTTTCA 407
F306  339 CTC-ATCAATGCTTCGTAATC-TCAAAGCAG---GGCAATA-TAAGC-----AAGCTTGT 387
```

FIG. 4 Cont.

```
F321  345 CTTGAAGGTTG-ATGGCGTTT-ATGGTTCTA---ACACTT--TAGGA-----GCTCTAAA 392
F315  316 TTTTGTAATCGGCTTGTCAGTCATTTTGACCTT-GGTACCGTTTTCATAGGAAGTGGATC 374
F376  422 CACCATG---CAGTTTCATCGTCAAG---CCAAGAGG---ACTTTAAGTCCTTCAGCCAT 472
F311  336 T--TGTTC-C-AAATCCAATG----GTCCAAACGCCC-----ACACCAT----CGTCATA 378
F328  408 TATTGCCC-TTATAGCCGTTTTCACGTGCTACAGCTTCAGTAATACCGTATTTGGTAGCA 466
F324  393 A-ACTTAC-TTGGCCA-AACGTGGCAA--AGAAGGCG-----AAAAGGTATTAGTGCGCG 442
F347  262 ------------------------------------------------------------ 261
F351  408 A-ACATAC-TTGTCAA-AACGTGGGAA--AGAAGGTG-----AGAAGGTTCTGGTGCGAG 457
F344  411 TGTTGCCC-TTAAAGCCGTTAGTACGTGCTACTGCTTCAGTAATACCGTACTTTGTTTCA 469
F340  422 CACCATG---CAGTTTCATCGTCAAG---CCAAGAGG---ACTTTAAGTCCTTCAGCCAT 472
F338  571 T-TTGTAG-TTGGCCGTGACAAAAAGTCTGGAAAGTT-----AGTATGCCTTGGAGGCAA   6
F336  428 TGCTGTTTACCAGGTATTTCTTGAAGG--CCAAGATG---CTTTT--TTGCTTCTGCAAT 480
F334  428 TGCTGTTTACCAGGTATTTCTTGAAGG--CCAAGATG---CTTTT--TTGCTTCTGCAAT 480
F332  571 T-TTGTAG-TTGGCCGTGACAAAAAGTCTGGAAAGTT-----AGTATGCCTTGGAGGCAA 623
F330  547 T-TTGTAG-TTGGCCGTGACAAAAAGTCTGGAAAGTT-----AGTATGCCTTGGAGGCAA 599
F307  349 G-CTGAAT-TT--CCTAAATG-GAATA--AG--G--C-----GG---GTGGTCGT--GTC 387
F309  393 A-ACTTAC-TTGGCCA-AACGTGGGAA--AGAAGGTG-----AGAAAGTCCTAGTGCGAG 442
F303  408 TATTGCCC-TTATAGCCGTTTTCACGTGCTACAGCTTCAGTAATACCGTATTTGGTAGCA 466
F301  408 TATTGCCC-TTATAGCCGTTTTCACGTGCTACAGCTTCAGTAATACCGTATTTGGTAGCA 466
F320  408 TATTGCCC-TTATAGCCGTTTTCACGTGCTACAGCTTCAGTAATACCGTATTTGGTAGCA 466
F306  388 G-CTTCAT-TA--CTGAAATACAAATA--TGTTG--C-----AAAGCGTGATTGCTCGAT 434
F321  393 A-ACTTAC-TTGGCCA-AACGTGGCAA--AGAAGGCG-----AAAAGGTCTTAGTGCGCG 442
F315  375 CGATACCAATCGTTGCCACTTTAGCGCTATCTAAATA---TGGCTTTGATTTGTACCCCT 431
F376  473 TTGA--TGATT-GTCTGGTTGTGTTTGGGGCCGGCGATTTCAGCCAA--------CCCTA 521
F311  379 GGCTTTCAAAC-----GTTTACCTTC---AAA---GCCTTTG-ATT-----AGATTGATT 421
F328  467 CCTCCTCGATCTACTGGATTATTTAC---ATAACCGCCTACGCGTT-----TAATCAAAT 518
F324  443 T--GTTAAATA--------TTATGCA-----AGGCCAACGAT-ACATT----GAAATC---- 480
F347  262 ------------------------------------------------------------ 261
F351  458 T--GCTCAATA--------TTATGCA-----AGGGCAACGCT-ACATT----GAAATC---- 495
F344  470 CCGCCTCGATCTGCTGGGTTGTTTAC---GTACCCGCCCTCACGCT-----TAATTAACT 521
F340  473 TTGA--TGATT-GTCTGGTTGTGTTTGGGGCCGGCGATTTCAGCCAA--------CCCTA 521
F338  624 TCAGTCAAATAAAGTTTGTTATGCACTTTATAATGACTCTGACTTTCAA-GAATTCAGAT 682
F336  481 CCAAGCTAATTCATCAGGCTTTGTT-GGTGTTGGGATATTCAATAAAGAATTGATCCCTA 539
F334  481 CCAAGCTAATTCATCAGGCTTTGTT-GGTGTTGGGATATTCAATAAAGAATTGATCCCTA 539
F332  624 TCAGTCAAATAAAGTTTGTTATGCACTTTATAATGACTCTGACTTTCAA-GAATTCAGAT 682
F330  600 TCAGTCAAATAAAGTTTGTTATGCACTTTATAATGACTCTGACTTTCAA-GAATTCAGAT 658
F307  388 TTGGCTGGAT-----TAGTTA-AAC----GTCGCAAAGCTGAAAT-----GGAGTTAT-T 431
```

FIG. 4 Cont.

```
F309  443  T--TCTTAATA-------TCATGCA----AGGCCAGCGAT-ATATC----GAAATT----  480
F303  467  CCTCCTCGATCTACTGGATTATTTAC---ATAACCGCCTTCGCGTT-----TAATCAAAT  518
F301  467  CCTCCTCGATCTACTGGATTATTTAC---ATAACCGCCTTCGCGTT-----TAATCAAAT  518
F320  467  CCTCCTCGATCTACTGGATTATTTAC---ATAACCGCCTTCGCGTT-----TAATCAAAT  518
F306  435  TCGGTCCAATGG---TTGTTATGGT----GTCTGGACACGCCAAC-----AAGATCGT-T  481
F321  443  T--GTTAAATA-------TTATGCA----AGGCCAACGAT-ACATT----GAAATC----  480
F315  432  CATAGCCAATTAAAGATGCAAAAAAAAGCGCTGATGCGCTTAATGTTGTTACTATGATTT  491
F376  522  TGTGACGGCGAGCCT-CTGCGATCCACG-----GTAATTCTGGA-TTTGCACTC--AT--  570
F311  422  CCT---GA-GTT--ACTTG-TTTTCAT---------------------------------  441
F328  519  CATCAAGATATT--GTTCAATTTTCAT---------------------------------  543
F324  481  --TGTGAACGTA--ATAAAA--GCCAAGAGCAGTTTTTTTATGGCTG-GATCGCTAACCG  533
F347  262  ------------------------------------------------------------  261
F351  496  --TGTGAGCGTA--ATCCAA--AGCAGGAACAGTTTTTCTATGGCTG-GATTGCTAACCG  548
F344  522  CGTCCAGATATT--GTTCAATGTTCATTTCGGTTTCCTTCAGATGTAAAAAACCGCCCGA  579
F340  522  TGTGACGGCGAGCCT-CTGCGATCCACG-----GTAATTCTGGA-TTTGCACTC--AT--  570
F338  683  GGTATGGTCGTACAACTCAACCAGCAAGTAAGCGTTATACATTGCCACAATTAAAAGGCG  742
F336  540  CTAACTGGCCTGTTAATTGCGGGCCATTAAGTCGTGGTTGAGAAATTTTCTTTCCAATCC  599
F334  540  CTAACTGGCCTGTTAATTGCGGGCCATTAAGTCGTGGTTGAGAAATTTTCTTTCCAATCC  599
F332  683  GGTATGGTCGTACAACTCAACCAGCAAGTAAGCGTTATACATTGCCACAATTAAAAGGCG  742
F330  659  GGTATGGTCGTACAACTCAACCAGCAAGTAAGCGTTATACATTGCCACAATTAAAAGGCG  718
F307  432  TTTA-AAATGA-------------------------------------------------  441
F309  481  --TGTGAGCGTA--ATCCTA--AGCAAGAGCAATTCTTCTATGGCTG-GATTGCTAACCG  533
F303  519  CATCAAGATATT--GTTCAATTTTCAT---------------------------------  543
F301  519  CATCAAGATATT--GTTCAATTTTCATTTCACTTTCCTTTAGACGTAAAAAAGCCACCAG  576
F320  519  CATCAAGATATT--GTTCAATTTTCAT---------------------------------  543
F306  482  ATAGCAAGTGTATGGCGGTGCAATGA----------------------------------  507
F321  481  --TGTGAACGTA--ATAAAA--GCCAAGAGCAGTTTTTTTATGGCTG-GATCGCTAACCG  533
F315  492  TAGTCTTGTTTGACAT--------------------------------------------  507
F376  571  ------------------------------------------------------------  570
F311  442  ------------------------------------------------------------  441
F328  544  ------------------------------------------------------------  543
F324  534  GATCGGCTAG--------------------------------------------------  543
F347  262  ------------------------------------------------------------  261
F351  549  GATCGGCTAG--------------------------------------------------  558
F344  580  AGGCGGCAT---------------------------------------------------  588
F340  571  ------------------------------------------------------------  570
F338  743  TAACAGCTACTAGGGTTTTGGAAGCCTAA-------------------------------  771
```

FIG. 4 Cont.

```
F336  600  ATGACAGAACAAGCATCAAAGTACCAGTAACAAATGCATGATATTTTTCAGGAATAACTT  659
F334  600  ATGACAGAACAAGCATCAAAGTACCAGTAACAAATGCATGATGTTTTTCAGGAATAACTT  659
F332  743  TAACAGCTACTAGGGTTTTGGAAGCCTAA-------------------------------  771
F330  719  TAACAGCTACTAGGGTTTTGGAAGCCTAA-------------------------------  747
F307  442  ------------------------------------------------------------  441
F309  534  GATCGGCTAG--------------------------------------------------  543
F303  544  ------------------------------------------------------------  543
F301  577  TTGATCCGTGAACTTGATATTTATATTGATCCAGAAGTGCAGGCTGAGGTTTTTGGTCAG  636
F320  544  ------------------------------------------------------------  543
F306  508  ------------------------------------------------------------  507
F321  534  GATCGGCTAG--------------------------------------------------  543
F315  508  ------------------------------------------------------------  507
F376  571  ------------------------------------------------------------  570
F311  442  ------------------------------------------------------------  441
F328  544  ------------------------------------------------------------  543
F324  544  ------------------------------------------------------------  543
F347  262  ------------------------------------------------------------  261
F351  559  ------------------------------------------------------------  558
F344  589  ------------------------------------------------------------  588
F340  571  ------------------------------------------------------------  570
F338  772  ------------------------------------------------------------  771
F336  660  CATAATCAACACCCCATTGTAGTGCTGGCAATAAAATTAGCATGATGAATGCACCTACGG  719
F334  660  CATAATCAACACCCCATTGTAGTGCTGGCAATAAAATTAGCATGATGAATGCACCTACGG  719
F332  772  ------------------------------------------------------------  771
F330  748  ------------------------------------------------------------  747
F307  442  ------------------------------------------------------------  441
F309  544  ------------------------------------------------------------  543
F303  544  ------------------------------------------------------------  543
F301  637  ------------------------------------------------------------  636
F320  544  ------------------------------------------------------------  543
F306  508  ------------------------------------------------------------  507
F321  544  ------------------------------------------------------------  543
F315  508  ------------------------------------------------------------  507
F376  571  ------------------------------------------------------------  570
F311  442  ------------------------------------------------------------  441
F328  544  ------------------------------------------------------------  543
F324  544  ------------------------------------------------------------  543
```

FIG. 4 Cont.

```
F347  262 ------------------------------------------------------------ 261
F351  559 ------------------------------------------------------------ 558
F344  589 ------------------------------------------------------------ 588
F340  571 ------------------------------------------------------------ 570
F338  772 ------------------------------------------------------------ 771
F336  720 CGGGTAACTTAACAGATAGATACTGCCAAGCATTGTTTTCAATTAACTTCAT-------- 771
F334  720 CGGGTAACTTAACAGATAGATACTGCCAAGCATTGTTTTCAATTAACTTCAT-------- 771
F332  772 ------------------------------------------------------------ 771
F330  748 ------------------------------------------------------------ 747
F307  442 ------------------------------------------------------------ 441
F309  544 ------------------------------------------------------------ 543
F303  544 ------------------------------------------------------------ 543
F301  637 ------------------------------------------------------------ 636
F320  544 ------------------------------------------------------------ 543
F306  508 ------------------------------------------------------------ 507
F321  544 ------------------------------------------------------------ 543
F315  508 ------------------------------------------------------------ 507
```

FIG. 5

ClustalW (v1.83) multiple sequence alignment

21 Sequences Aligned      Processing time: 0.3 seconds
Gaps Inserted = 50          Conserved Identities = 1
                    Score = 83346

Pairwise Alignment Mode: Slow
Pairwise Alignment Parameters:
Open Gap Penalty = 10.0    Extend Gap Penalty = 0.1
Similarity Matrix: gonnet Multiple Alignment Parameters:
Open Gap Penalty = 10.0    Extend Gap Penalty = 0.1
Delay Divergent = 40%    Gap Distance = 8
Similarity Matrix: gonnet

```
F307   1 ------------------------------------------------------------   0
F376   1 ------------------------------------------------------------   0
F351   1 ------------------------------------------------------------   0
F347   1 ------------------------------------------------------------   0
F344   1 ------------------------------------------------------------   0
F340   1 ------------------------------------------------------------   0
F338   1 MKLIENNAWQYLSVKLPAVGAFIMLILLPALQWGVDYEVIPEKYHAFVTGTLMLVLSWIG  60
F336   1 MKLIENNAWQYLSVKLPAVGAFIMLILLPALQWGVDYEVIPEKYHAFVTGTLMLVLSWIG  60
F334   1 MKLIENNAWQYLSVKLPAVGAFIMLILLPALQWGVDYEVIPEKHHAFVTGTLMLVLSWIG  60
F332   1 MKLIENNAWQYLSVKLPAVGAFIMLILLPALQWGVDYEVIPEKYHAFVTGTLMLVLSWIG  60
F330   1 ----LDPVMTMTSSPFHNS----SRILLPALQWGVDYEVIPEKYHAFVTGTLMLVLSWIG  52
F328   1 ------------------------------------------------------------   0
F324   1 ------------------------------------------------------------   0
F321   1 ------------------------------------------------------------   0
F320   1 ------------------------------------------------------------   0
F315   1 ------------------------------------------------------------   0
F306   1 ------------------------------------------------------------   0
F303   1 ------------------------------------------------------------   0
F301   1 --------------------------------------------------------LTKN   4
F309   1 ------------------------------------------------------------   0
F311   1 ------------------------------------------------------------   0
```

FIG. 5 Cont.

```
F307    1  ----------------------------VKTSNPGVDLIKGFEGLRLKAYDDGVGVWTIGF  33
F376    1  ---------------------------MSANP-ELPWIAEARRHIGLAEIAGPKHNQTII  32
F351    1  ----------------------LKETEMNIEKYLDELIKREGGYVNNPADRGGATKYGIT  38
F347    1  -------------------------------------------------LPSTTR-----   6
F344    1  --------------MPPSGGFLHLKETEMNIEQYLDELIKREGGYVNNPADRGGETKYGIT 47
F340    1  ---------------------------MSANP-ELPWIAEARRHIGLAEIAGPKHNQTII  32
F338   61  KKISQPRLNGPQLTGQLVGINSLLNIPTPTKPDELAWIAEAKKHLGLQEIPGKQHNPTIL 120
F336   61  KKISQPRLNGPQLTGQLVGINSLLNIPTPTKPDELAWIAEAKKHLGLQEIPGKQHNPTIL 120
F334   61  KKISQPRLNGPQLTGQLVGINSLLNIPTPTKPDELAWIAEAKKHLGLQEIPGKQHNPTIL 120
F332   61  KKISQPRLNGPQLTGQLVGINSLLNIPTPTKPDELAWIAEAKKHLGLQEIPGKQHNPTIL 120
F330   53  KKISQPRLNGPQLTGQLVGINSLLNIPTPTKPDELAWIAEAKKHLGLQEIPGKQHNPTIL 112
F328    1  --------------------------MKIEQYLDDLIKRVGGYVNNPVDRGGATKYGIT  33
F324    1  --------------------------MKIEQYLDDLIKREGGYVNNPVDRGGATKYGIT  33
F321    1  --------------------------MKIEQYLDDLIKREGGYVNNPVDRGGATKYGIT  33
F320    1  --------------------------MKIEQYLDDLIKREGGYVNNPVDRGGATKYGIT  33
F315    1  ----------------MSNKTKIIVTTLSASALFFASLIGYEGYKSKPYLDSAKVATIGI  44
F306    1  ----------------MSNKTKIIVTTLSASALFFASLIGYEGYKSKPYLDSAKVATIGI  44
F303    1  --------------------------MKIEQYLDDLIKREGGYVNNPVDRGGATKYGIT  33
F301    5  LSLHFWININIKFTDQLVAFLRLKESEMKIEQYLDDLIKREGGYVNNPVDRGGATKYGIT  64
F309    1  --------------------------MKIEQYLDDLIKREGGYVNNPVDRGGATKYGIT  33
F311    1  --------------------------MKTSNSGINLIKGFEGKRLKAYDDGVGVWTIGF  33

F307   34  GTIKYPNGVRVKKGDTCTESQAEEYLRNDLVV-------------------------FES  68
F376   33  KWLKDLKSSWLDDETAWCGTFVAHCLQTAGFQRGSVNSRSKTYKSGTKAPPGFYPFNWYA  92
F351   39  QAVARENGWNGNMKDLPLDVAKAIYKKQYWTAPRFDQVNA------------VSSAVAEE  86
F347    7  ------------------------------------------------------------   6
F344   48  EAVARTNGFKGNMKDLPLDVAKAIYKKQYWTDPRFDQVNV------------ISSLVAEE  95
F340   33  KWLKDLKSSWLDDETAWCGTFVAHCLQTAGFQRGSVNSRSKTYKSGTKAPPGFYPFNWYA  92
F338  121  KWLSELKAWWADDETAWCGTFVAHCLKSAGIA--------------------YPKHWYR 159
F336  121  KWLSELKAWWADDETAWCGTFVAHCLKSAGIA--------------------YPKHWYR 159
F334  121  KWLSELKAWWADDETAWCGTFVAHCLKSAGIA--------------------YPKHWYR 159
F332  121  KWLSELKAWWADDETAWCGTFVAHCLKSAGIA--------------------YPKHWYR 159
F330  113  KWLSELKAWWADDETAWCGTFVAHCLKSAGIA--------------------YSKHWYR 151
F328   34  EAVARENGYKGNMKDLPLDVAKAIYRKQYWIEPRFDQVNT------------LSSAVAEE  81
F324   34  EAVARENGYKGNMKDLPLDVAKAIYRKQYWIEPRFDQVNT------------LSSAVAEE  81
F321   34  EAVARENGYKGNMKDLPLDVAKAIYRKQYWIEPRFDQVNT------------LSSAVAEE  81
F320   34  EAVARENGYKGNMKDLPLDVAKAIYRKQYWIEPRFDQVNT------------LSSAVAEE  81
F315   45  GSTSYENGTKVKMTDKPITKERAVQIAKAHIA-------------------------KDE  79
```

FIG. 5 Cont.

```
F306   45 GSTSYENGTKVKMTDKPITKERAVQIAKAHIA------------------------KDE  79
F303   34 EAVARENGYKGNMKDLPLDVAKAIYRKQYWIEPRFDQVNT------------LSSAVAEE  81
F301   65 EAVARENGYKGNMKDLPLDVAKAIYRKQYWIEPRFDQVNT------------LSSAVAEE 112
F309   34 EAVARENGYKGNMKDLPLDVAKAIYRKQYWIEPRFDQVNT------------LSSAVAEE  81
F311   34 GTIKYPNGVRVKKGDICTESQAEGYLRNDLVA------------------------FEN  68
F307   69 AINR--LVKVPLNQNQFDALASFTYNLG------EGNLSISTLLKKLNAKDYKGAAAEFP 120
F376   93 ALEYIKEGGVKLXKPCYGCVAVKSREGGGHVTFVVGKTP-TGKLICLGGNQSNKVCFAVY 151
F351   87 LLDTGVNCGTGFAKPLLQRALNLLNNQG------KAGYADLEVDGVYGSATLGALKTYLS 140
F347    7 ---------AELSQTEYDLYLDFTYQYG------VPTFAKSSMLKHLKAGQYKAACDSLL  51
F344   96 LLDTGVNCGTGFAKPLLQRALNLLNNQG------KAGWPDLTVDGIYGPATLNALKTYLA 149
F340   93 ALEYIKEGGVKLDKPCYGCVAVKSREGGGHVTFVVGKTP-TGKLICLGGNQSNKVCFAVY 151
F338  160 ALDYVNYG-TKLAKPAYGCVAIKTRKGGGHVCFVVGRDKKSGKLVCLGGNQSNKVCYALY 218
F336  160 ALDYVNYG-TKLAKPAYGCVAIKTRKGGGHVCFVVGRDKKSGKLVCLGGNQSNKVCYALY 218
F334  160 ALDYVNYG-TKLAKPAYGCVAIKTRKGGGHVCFVVGRDKKSGKLVCLGGNQSNKVCYALY 218
F332  160 ALDYVNYG-TKLAKPAYGCVAIKTRKGGGHVCFVVGRDKKSGKLVCLGGNQSNKVCYALY 218
F330  152 ALDYVNYG-TKLAKPAYGCVAIKTRKGGGRVCFVVGRDKKSGKLVCLGGNQSNKVCYALY 210
F328   82 LLDTGVNCGINFAKPLLQRALNLLNNQG------KAGYADLKVDGVYGSNTLGALKTYLA 135
F324   82 LLDTGVNCGINFAKPLLQRALNLLNNQG------KAGYADLKVDGVYGSNTLGALKTYLA 135
F321   82 LLDTGVNCGINFAKPLLQRALNLLNNQG------KAGYADLKVDGVYGSNTLGALKTYLA 135
F320   82 LLDTGVNCGINFAKPLLQRALNLLNNQG------KAGYADLKVDGVYGSSTLGALKTYLA 135
F315   80 VAFRKSLQGVRLTQTEYDVYLDFVYNYG------QANWNGSSMLRNLKAGQYKQACASLL 133
F306   80 VAFRKSLQGVRLTQTEYDVYLDFVYNYG------QANWNGSSMLRNLKAGQYKQACASLL 133
F303   82 LLDTGVNCGINFAKPLLQRALNLLNNQG------KAGYADLKVDGVYGSSTLGALKTYLA 135
F301  113 LLDTGVNCGINFAKPLLQRALNLLNNQG------KAGYADLKVDGVYGSNTLGALKTYLA 166
F309   82 LLDTGVNCGINFAKPLLQRALNLLNNQG------KAGYTDLKVDGVYGSSTLGALKTYLA 135
F311   69 AINR--LVKVPLNQNQFDALASFTYNLG------EGNLSKSTLLKKLNAKDYKGAAAEFP 120
F307  121 KWNKAGGR-----------VLAGLVKRRKAEMELFLK----------------------146
F376  152 DVSAFEAFMWYGKTSKPAAHRYDLPVLKIVSVTSVSEA--------------------189
F351  141 KRGKEGEKVLVRVLNIMQGQRYIEICERNPKQEQFFYGWIANRIG-------------185
F347   52 KYKYVAKRDCS-----VRKNGCYGVWTRQVERHAKCIGAQ--------------------86
F344  150 KRGKDGEKVLVRVLNIMQGQRYIEICERNPSQEQFFYGWIANRVVI--------------195
F340  152 DVSAFEAFMWYGKTSKPAAHRYDLPVLKIVSVTSVSEA--------------------189
F338  219 NDSDFQEFRWYGRTTQPASKRYTLPQLKGVTATRVLEA--------------------256
F336  219 NDSDFQEFRWYGRTTQPASKRYTLPQLKGVTATRVLEA--------------------256
F334  219 NDSDFQEFRWYGRTTQPAGKRYTLPQLKGVTATRVLEA--------------------256
F332  219 NDSDFQEFRWYGRTTQPASKRYTLPQLKGVTATRVLEA--------------------256
F330  211 NDSDFQEFRWYGRTTQPASKRYTLPQLKGVTATRVLEA--------------------248
```

FIG. 5 Cont.

```
F328  136  KRGKEGEKVLVRVLNIMQGQRYIEICERNKSQEQFFYGWIANRIG----------------180
F324  136  KRGKEGEKVLVRVLNIMQGQRYIEICERNKSQEQFFYGWIANRIG----------------180
F321  136  KRGKEGEKVLVRVLNIMQGQRYIEICERNKSQEQFFYGWIANRIG----------------180
F320  136  KRGKEGEKVLVRVLNIMQGQRYIEICERNPKQEQFFYGWIANRIG----------------180
F315  134  KYKYVAKRDCS-----IRSNGCYGVWTRQQDCYSKCMAVQ---------------------168
F306  134  KYKYVAKRDCS-----IRSNGCYGVWTRQQDRYSKCMAVQ---------------------168
F303  136  KRGKEGEKVLVRVLNIMQGQRYIEICERNPKQEQFFYGWIANRIG----------------180
F301  167  KRGKEGEKVLVRVLNIMQGQRYIEICERNKSQEQFFYGWIANRIG----------------211
F309  136  KRGKEGEKVLVRVLNIMQGQRYIEICERNPKQEQFFYGWIANRIG----------------180
F311  121  KWNKAGGR------------VLAGLVKRRKAEMELFLK-----------------------146
```

FIG. 8
0 Time
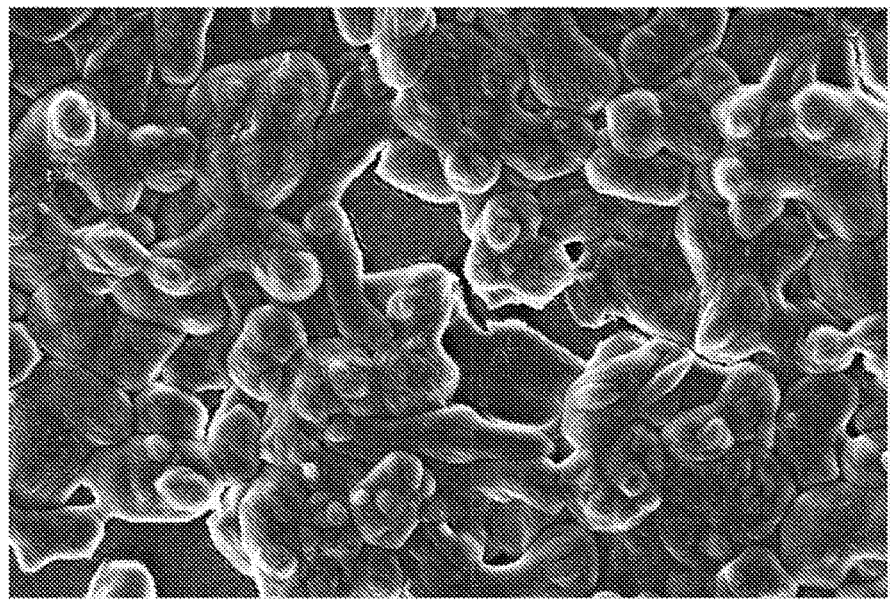
30 Min
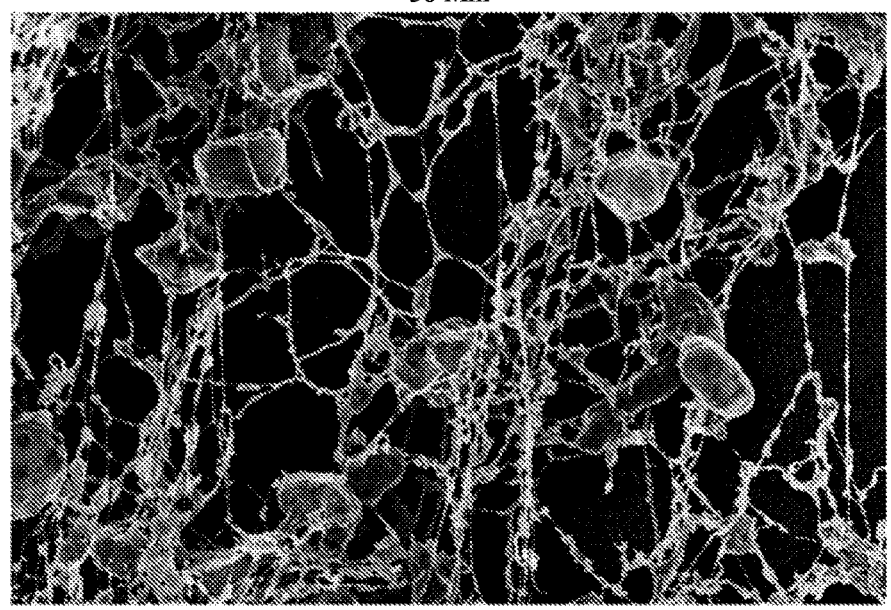

VKTSNPGVDL IKGFEGLRLK AYDDGVGVWT IGFGTIKYPN GVRVKKGDTC TESQAEEYLR
NDLVVFESAI NRLVKVPLNQ NQFDALASFT YNLGEGNLSI STLLKKLNAK DYKGAAAEFP
KWNKAGGRVL AGLVKRRKAE MELFLK (SEQ ID NO:1)

P307- NAKDYKGAAAEFPKWNKAGGRVLAGLVKRRK -- 3.4 kDa (SEQ ID NO:43)

P307Ex - NAKDYKGAAAEFPKWNKAGGRVLAGLVKRRKSQSRESQC -- 4.3 kDa (SEQ ID NO:45)

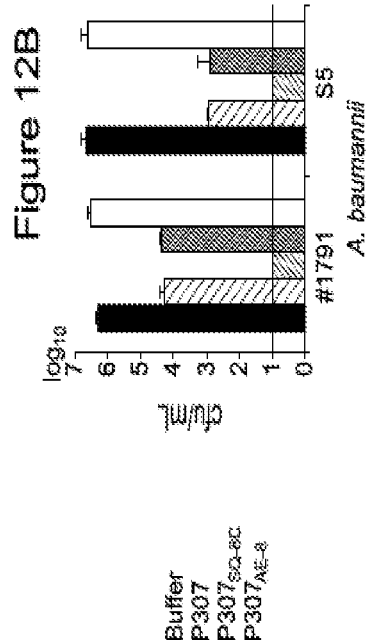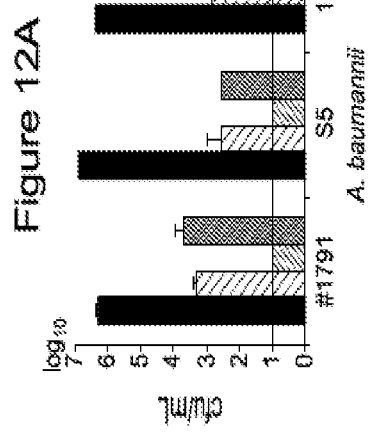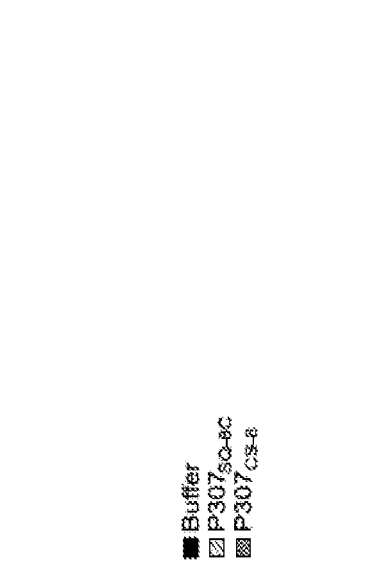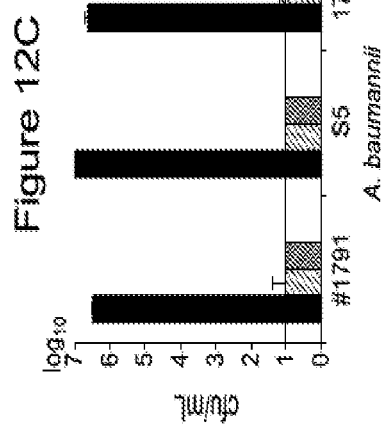
Figure 12A
Figure 12B
Figure 12C

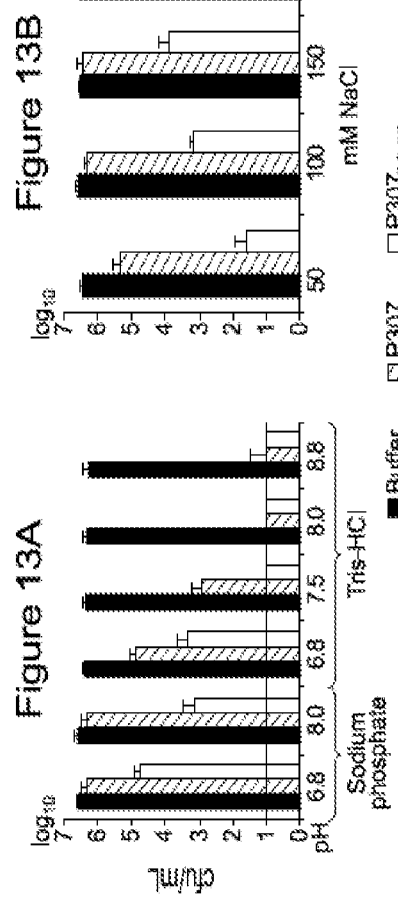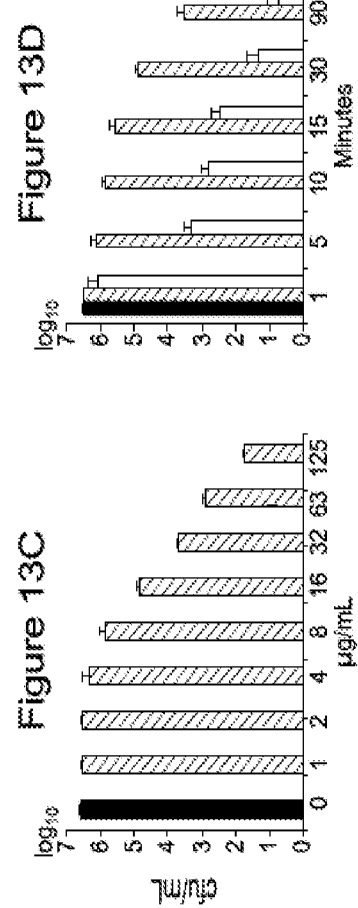

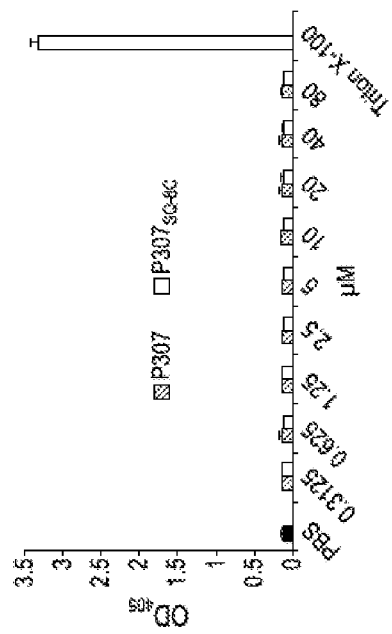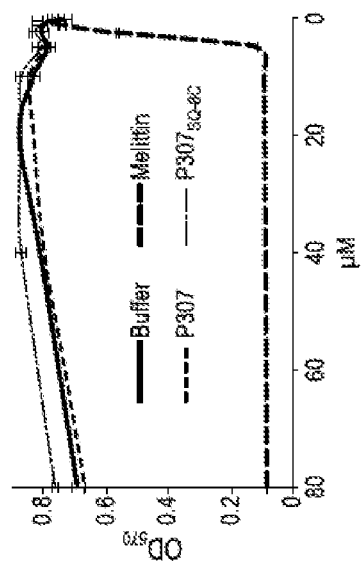
Figure 16B
Figure 16A

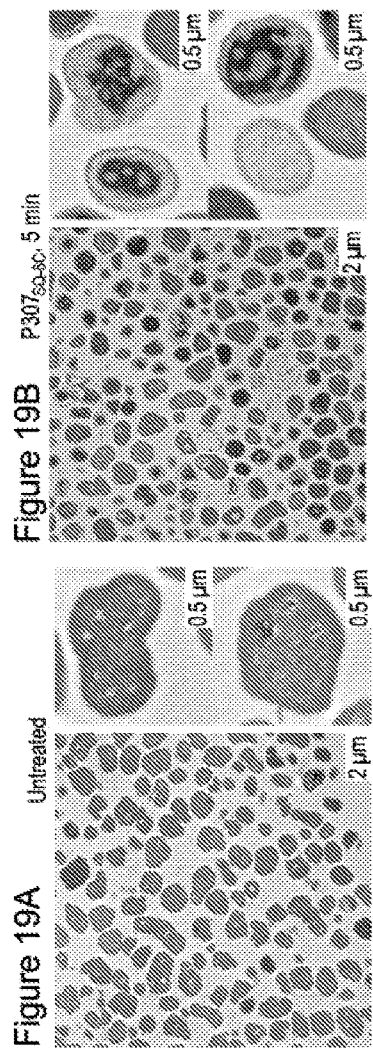
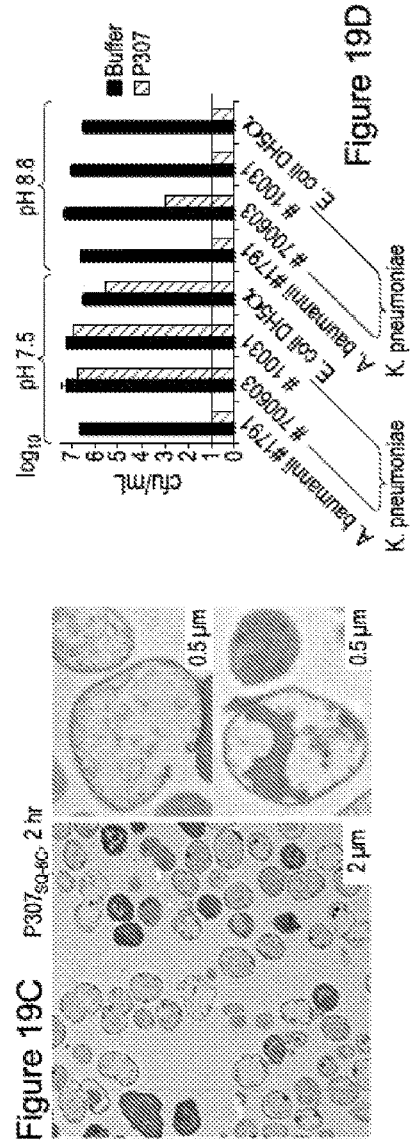

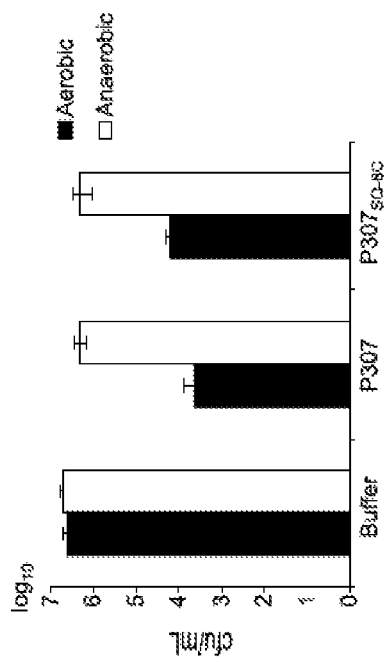
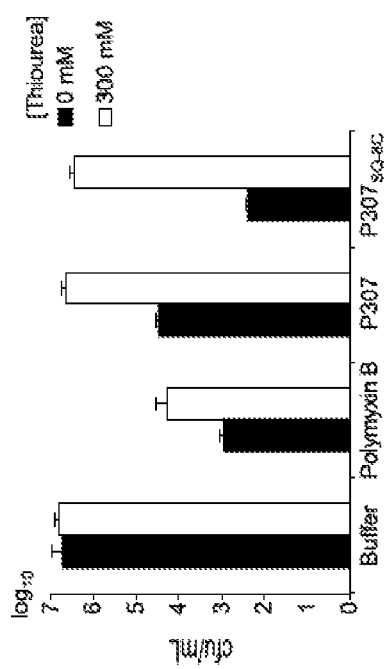
Figure 21A
Figure 21B

SEQUENCE LISTING

```
<160> NUMBER OF SEQ ID NOS: 53

<210> SEQ ID NO 1
<211> LENGTH: 146
<212> TYPE: PRT
<213> ORGANISM: Acinetobacter baumannii

<400> SEQUENCE: 1

Val Lys Thr Ser Asn Pro Gly Val Asp Leu Ile Lys Gly Phe Glu Gly
1               5                   10                  15

Leu Arg Leu Lys Ala Tyr Asp Asp Gly Val Gly Val Trp Thr Ile Gly
            20                  25                  30

Phe Gly Thr Ile Lys Tyr Pro Asn Gly Val Arg Val Lys Lys Gly Asp
        35                  40                  45

Thr Cys Thr Glu Ser Gln Ala Glu Glu Tyr Leu Arg Asn Asp Leu Val
    50                  55                  60

Val Phe Glu Ser Ala Ile Asn Arg Leu Val Lys Val Pro Leu Asn Gln
65                  70                  75                  80

Asn Gln Phe Asp Ala Leu Ala Ser Phe Thr Tyr Asn Leu Gly Glu Gly
                85                  90                  95

Asn Leu Ser Ile Ser Thr Leu Leu Lys Lys Leu Asn Ala Lys Asp Tyr
            100                 105                 110

Lys Gly Ala Ala Ala Glu Phe Pro Lys Trp Asn Lys Ala Gly Gly Arg
        115                 120                 125

Val Leu Ala Gly Leu Val Lys Arg Arg Lys Ala Glu Met Glu Leu Phe
    130                 135                 140

Leu Lys
145

<210> SEQ ID NO 2
<211> LENGTH: 189
<212> TYPE: PRT
<213> ORGANISM: Acinetobacter baumannii
<220> FEATURE:

Ala Pro Pro Gly Phe Tyr Pro Phe Asn Trp Tyr Ala Ala Leu Glu Tyr
                85                  90                  95

Ile Lys Glu Gly Gly Val Lys Leu Asx Lys Pro Cys Tyr Gly Cys Val
            100                 105                 110

Ala Val Lys Ser Arg Glu Gly Gly His Val Thr Phe Val Val Gly
            115                 120                 125

Lys Thr Pro Thr Gly Lys Leu Ile Cys Leu Gly Gly Asn Gln Ser Asn
145             130                 135                 140

Lys Val Cys Phe Ala Val Tyr Asp Val Ser Ala Phe Glu Ala Phe Met
145                 150                 155                 160

Trp Tyr Gly Lys Thr Ser Lys Pro Ala Ala His Arg Tyr Asp Leu Pro
                165                 170                 175

Val Leu Lys Ile Val Ser Val Thr Ser Val Ser Glu Ala
                180                 185

<210> SEQ ID NO 3
<211> LENGTH: 185
<212> TYPE: PRT
<213> ORGANISM: Acinetobacter baumannii

<400> SEQUENCE: 3

Leu Lys Glu Thr Glu Met Asn Ile Glu Lys Tyr Leu Asp Glu Leu Ile
1               5                   10                  15

Lys Arg Glu Gly Gly Tyr Val Asn Asn Pro Ala Asp Arg Gly Gly Ala
            20                  25                  30

Thr Lys Tyr Gly Ile Thr Gln Ala Val Ala Arg Glu Asn Gly Trp Asn
        35                  40                  45

Gly Asn Met Lys Asp Leu Pro Leu Asp Val Ala Lys Ala Ile Tyr Lys
50              55                  60

Lys Gln Tyr Trp Thr Ala Pro Arg Phe Asp Gln Val Asn Ala Val Ser
65                  70                  75                  80

Ser Ala Val Ala Glu Glu Leu Leu Asp Thr Gly Val Asn Cys Gly Thr
                85                  90                  95

Gly Phe Ala Lys Pro Leu Leu Gln Arg Ala Leu Asn Leu Leu Asn Asn
            100                 105                 110

Gln Gly Lys Ala Gly Tyr Ala Asp Leu Glu Val Asp Gly Val Tyr Gly
        115                 120                 125

Ser Ala Thr Leu Gly Ala Leu Lys Thr Tyr Leu Ser Lys Arg Gly Lys
        130                 135                 140

Glu Gly Glu Lys Val Leu Val Arg Val Leu Asn Ile Met Gln Gly Gln
145                 150                 155                 160

Arg Tyr Ile Glu Ile Cys Glu Arg Asn Pro Lys Gln Glu Gln Phe Phe
                165                 170                 175

Tyr Gly Trp Ile Ala Asn Arg Ile Gly
            180                 185

<210> SEQ ID NO 4
<211> LENGTH: 86
<212> TYPE: PRT
<213> ORGANISM: Acinetobacter baumannii

<400> SEQUENCE: 4

Leu Pro Ser Thr Thr Arg Ala Glu Leu Ser Gln Thr Glu Tyr Asp Leu
1               5                   10                  15

Tyr Leu Asp Phe Thr Tyr Gln Tyr Gly Val Pro Thr Phe Ala Lys Ser
            20                  25                  30

Ser Met Leu Lys His Leu Lys Ala Gly Gln Tyr Lys Ala Cys Asp
         35                  40                  45

Ser Leu Leu Lys Tyr Lys Tyr Val Ala Lys Arg Asp Cys Ser Val Arg
 50                  55                  60

Lys Asn Gly Cys Tyr Gly Val Trp Thr Arg Gln Val Glu Arg His Ala
 65                  70                  75                  80

Lys Cys Ile Gly Ala Gln
             85

<210> SEQ ID NO 5
<211> LENGTH: 195
<212> TYPE: PRT
<213> ORGANISM: Acinetobacter baumannii

<400> SEQUENCE: 5

Met Pro Pro Ser Gly Gly Phe Leu His Leu Lys Glu Thr Glu Met Asn
 1               5                  10                  15

Ile Glu Gln Tyr Leu Asp Glu Leu Ile Lys Arg Glu Gly Gly Tyr Val
                 20                  25                  30

Asn Asn Pro Ala Asp Arg Gly Gly Glu Thr Lys Tyr Gly Ile Thr Glu
             35                  40                  45

Ala Val Ala Arg Thr Asn Gly Phe Lys Gly Asn Met Lys Asp Leu Pro
 50                  55                  60

Leu Asp Val Ala Lys Ala Ile Tyr Lys Lys Gln Tyr Trp Thr Asp Pro
 65                  70                  75                  80

Arg Phe Asp Gln Val Asn Val Ile Ser Ser Leu Val Ala Glu Glu Leu
                 85                  90                  95

Leu Asp Thr Gly Val Asn Cys Gly Thr Gly Phe Ala Lys Pro Leu Leu
            100                 105                 110

Gln Arg Ala Leu Asn Leu Leu Asn Asn Gln Gly Lys Ala Gly Trp Pro
        115                 120                 125

Asp Leu Thr Val Asp Gly Ile Tyr Gly Pro Ala Thr Leu Asn Ala Leu
130                 135                 140

Lys Thr Tyr Leu Ala Lys Arg Gly Lys Asp Gly Glu Lys Val Leu Val
145                 150                 155                 160

Arg Val Leu Asn Ile Met Gln Gly Gln Arg Tyr Ile Glu Ile Cys Glu
                165                 170                 175

Arg Asn Pro Ser Gln Glu Gln Phe Phe Tyr Gly Trp Ile Ala Asn Arg
            180                 185                 190

Val Val Ile
        195

<210> SEQ ID NO 6
<211> LENGTH: 189
<212> TYPE: PRT
<213> ORGANISM: Acinetobacter baumannii

<400> SEQUENCE: 6

Met Ser Ala Asn Pro Glu Leu Pro Trp Ile Ala Glu Ala Arg Arg His
 1               5                  10                  15

Ile Gly Leu Ala Glu Ile Ala Gly Pro Lys His Asn Gln Thr Ile Ile
                 20                  25                  30

Lys Trp Leu Lys Asp Leu Lys Ser Ser Trp Leu Asp Asp Glu Thr Ala
             35                  40                  45

Trp Cys Gly Thr Phe Val Ala His Cys Leu Gln Thr Ala Gly Phe Gln
 50                  55                  60

-continued

Arg Gly Ser Val Asn Ser Arg Ser Lys Thr Tyr Lys Ser Gly Thr Lys
 65                  70                  75                  80

Ala Pro Pro Gly Phe Tyr Pro Phe Asn Trp Tyr Ala Ala Leu Glu Tyr
                 85                  90                  95

Ile Lys Glu Gly Gly Val Lys Leu Asp Lys Pro Cys Tyr Gly Cys Val
            100                 105                 110

Ala Val Lys Ser Arg Glu Gly Gly His Val Thr Phe Val Val Gly
            115                 120                 125

Lys Thr Pro Thr Gly Lys Leu Ile Cys Leu Gly Gly Asn Gln Ser Asn
            130                 135                 140

Lys Val Cys Phe Ala Val Tyr Asp Val Ser Ala Phe Glu Ala Phe Met
145                 150                 155                 160

Trp Tyr Gly Lys Thr Ser Lys Pro Ala Ala His Arg Tyr Asp Leu Pro
                165                 170                 175

Val Leu Lys Ile Val Ser Val Thr Ser Val Ser Glu Ala
            180                 185

<210> SEQ ID NO 7
<211> LENGTH: 256
<212> TYPE: PRT
<213> ORGANISM: Acinetobacter baumannii

<400> SEQUENCE: 7

Met Lys Leu Ile Glu Asn Asn Ala Trp Gln Tyr Leu Ser Val Lys Leu
 1               5                  10                  15

Pro Ala Val Gly Ala Phe Ile Met Leu Ile Leu Pro Ala Leu Gln
                20                  25                  30

Trp Gly Val Asp Tyr Glu Val Ile Pro Glu Lys Tyr His Ala Phe Val
             35                  40                  45

Thr Gly Thr Leu Met Leu Val Leu Ser Trp Ile Gly Lys Lys Ile Ser
         50                  55                  60

Gln Pro Arg Leu Asn Gly Pro Gln Leu Thr Gly Gln Leu Val Gly Ile
 65                  70                  75                  80

Asn Ser Leu Leu Asn Ile Pro Thr Pro Thr Lys Pro Asp Glu Leu Ala
                 85                  90                  95

Trp Ile Ala Glu Ala Lys Lys His Leu Gly Leu Gln Glu Ile Pro Gly
            100                 105                 110

Lys Gln His Asn Pro Thr Ile Leu Lys Trp Leu Ser Glu Leu Lys Ala
            115                 120                 125

Trp Trp Ala Asp Asp Glu Thr Ala Trp Cys Gly Thr Phe Val Ala His
            130                 135                 140

Cys Leu Lys Ser Ala Gly Ile Ala Tyr Pro Lys His Trp Tyr Arg Ala
145                 150                 155                 160

Leu Asp Tyr Val Asn Tyr Gly Thr Lys Leu Ala Lys Pro Ala Tyr Gly
                165                 170                 175

Cys Val Ala Ile Lys Thr Arg Lys Gly Gly His Val Cys Phe Val
            180                 185                 190

Val Gly Arg Asp Lys Lys Ser Gly Lys Leu Val Cys Leu Gly Gly Asn
            195                 200                 205

Gln Ser Asn Lys Val Cys Tyr Ala Leu Tyr Asn Asp Ser Asp Phe Gln
            210                 215                 220

Glu Phe Arg Trp Tyr Gly Arg Thr Thr Gln Pro Ala Ser Lys Arg Tyr
225                 230                 235                 240

Thr Leu Pro Gln Leu Lys Gly Val Thr Ala Thr Arg Val Leu Glu Ala
                245                 250                 255

<210> SEQ ID NO 8
<211> LENGTH: 256
<212> TYPE: PRT
<213> ORGANISM: Acinetobacter baumannii

<400> SEQUENCE: 8

Met Lys Leu Ile Glu Asn Asn Ala Trp Gln Tyr Leu Ser Val Lys Leu
1               5                   10                  15

Pro Ala Val Gly Ala Phe Ile Met Leu Ile Leu Pro Ala Leu Gln
            20                  25                  30

Trp Gly Val Asp Tyr Glu Val Ile Pro Glu Lys Tyr His Ala Phe Val
            35                  40                  45

Thr Gly Thr Leu Met Leu Val Leu Ser Trp Ile Gly Lys Lys Ile Ser
        50                  55                  60

Gln Pro Arg Leu Asn Gly Pro Gln Leu Thr Gly Gln Leu Val Gly Ile
65                  70                  75                  80

Asn Ser Leu Leu Asn Ile Pro Thr Pro Thr Lys Pro Asp Glu Leu Ala
                85                  90                  95

Trp Ile Ala Glu Ala Lys Lys His Leu Gly Leu Gln Glu Ile Pro Gly
            100                 105                 110

Lys Gln His Asn Pro Thr Ile Leu Lys Trp Leu Ser Glu Leu Lys Ala
        115                 120                 125

Trp Trp Ala Asp Asp Glu Thr Ala Trp Cys Gly Thr Phe Val Ala His
130                 135                 140

Cys Leu Lys Ser Ala Gly Ile Ala Tyr Pro Lys His Trp Tyr Arg Ala
145                 150                 155                 160

Leu Asp Tyr Val Asn Tyr Gly Thr Lys Leu Ala Lys Pro Ala Tyr Gly
                165                 170                 175

Cys Val Ala Ile Lys Thr Arg Lys Gly Gly His Val Cys Phe Val
            180                 185                 190

Val Gly Arg Asp Lys Lys Ser Gly Lys Leu Val Cys Leu Gly Gly Asn
        195                 200                 205

Gln Ser Asn Lys Val Cys Tyr Ala Leu Tyr Asn Asp Ser Asp Phe Gln
210                 215                 220

Glu Phe Arg Trp Tyr Gly Arg Thr Thr Gln Pro Ala Ser Lys Arg Tyr
225                 230                 235                 240

Thr Leu Pro Gln Leu Lys Gly Val Thr Ala Thr Arg Val Leu Glu Ala
                245                 250                 255

<210> SEQ ID NO 9
<211> LENGTH: 256
<212> TYPE: PRT
<213> ORGANISM: Acinetobacter baumannii

<400> SEQUENCE: 9

Met Lys Leu Ile Glu Asn Asn Ala Trp Gln Tyr Leu Ser Val Lys Leu
1               5                   10                  15

Pro Ala Val Gly Ala Phe Ile Met Leu Ile Leu Pro Ala Leu Gln
            20                  25                  30

Trp Gly Val Asp Tyr Glu Val Ile Pro Glu Lys His His Ala Phe Val
            35                  40                  45

Thr Gly Thr Leu Met Leu Val Leu Ser Trp Ile Gly Lys Lys Ile Ser
        50                  55                  60

Gln Pro Arg Leu Asn Gly Pro Gln Leu Thr Gly Gln Leu Val Gly Ile
65                  70                  75                  80

```
Asn Ser Leu Leu Asn Ile Pro Thr Pro Thr Lys Pro Asp Glu Leu Ala
                85                  90                  95

Trp Ile Ala Glu Ala Lys Lys His Leu Gly Leu Gln Glu Ile Pro Gly
            100                 105                 110

Lys Gln His Asn Pro Thr Ile Leu Lys Trp Leu Ser Glu Leu Lys Ala
        115                 120                 125

Trp Trp Ala Asp Asp Glu Thr Ala Trp Cys Gly Thr Phe Val Ala His
130                 135                 140

Cys Leu Lys Ser Ala Gly Ile Ala Tyr Pro Lys His Trp Tyr Arg Ala
145                 150                 155                 160

Leu Asp Tyr Val Asn Tyr Gly Thr Lys Leu Ala Lys Pro Ala Tyr Gly
                165                 170                 175

Cys Val Ala Ile Lys Thr Arg Lys Gly Gly Gly His Val Cys Phe Val
            180                 185                 190

Val Gly Arg Asp Lys Lys Ser Gly Lys Leu Val Cys Leu Gly Gly Asn
        195                 200                 205

Gln Ser Asn Lys Val Cys Tyr Ala Leu Tyr Asn Asp Ser Asp Phe Gln
210                 215                 220

Glu Phe Arg Trp Tyr Gly Arg Thr Thr Gln Pro Ala Gly Lys Arg Tyr
225                 230                 235                 240

Thr Leu Pro Gln Leu Lys Gly Val Thr Ala Thr Arg Val Leu Glu Ala
                245                 250                 255

<210> SEQ ID NO 10
<211> LENGTH: 256
<212> TYPE: PRT
<213> ORGANISM: Acinetobacter baumannii

<400> SEQUENCE: 10

Met Lys Leu Ile Glu Asn Asn Ala Trp Gln Tyr Leu Ser Val Lys Leu
1               5                   10                  15

Pro Ala Val Gly Ala Phe Ile Met Leu Ile Leu Pro Ala Leu Gln
            20                  25                  30

Trp Gly Val Asp Tyr Glu Val Ile Pro Glu Lys Tyr His Ala Phe Val
        35                  40                  45

Thr Gly Thr Leu Met Leu Val Leu Ser Trp Ile Gly Lys Lys Ile Ser
    50                  55                  60

Gln Pro Arg Leu Asn Gly Pro Gln Leu Thr Gly Gln Leu Val Gly Ile
65                  70                  75                  80

Asn Ser Leu Leu Asn Ile Pro Thr Pro Thr Lys Pro Asp Glu Leu Ala
                85                  90                  95

Trp Ile Ala Glu Ala Lys Lys His Leu Gly Leu Gln Glu Ile Pro Gly
            100                 105                 110

Lys Gln His Asn Pro Thr Ile Leu Lys Trp Leu Ser Glu Leu Lys Ala
        115                 120                 125

Trp Trp Ala Asp Asp Glu Thr Ala Trp Cys Gly Thr Phe Val Ala His
130                 135                 140

Cys Leu Lys Ser Ala Gly Ile Ala Tyr Pro Lys His Trp Tyr Arg Ala
145                 150                 155                 160

Leu Asp Tyr Val Asn Tyr Gly Thr Lys Leu Ala Lys Pro Ala Tyr Gly
                165                 170                 175

Cys Val Ala Ile Lys Thr Arg Lys Gly Gly Gly His Val Cys Phe Val
            180                 185                 190

Val Gly Arg Asp Lys Lys Ser Gly Lys Leu Val Cys Leu Gly Gly Asn
```

```
                195                 200                 205
    Gln Ser Asn Lys Val Cys Tyr Ala Leu Tyr Asn Asp Ser Asp Phe Gln
        210                 215                 220

Glu Phe Arg Trp Tyr Gly Arg Thr Thr Gln Pro Ala Ser Lys Arg Tyr
    225                 230                 235                 240

Thr Leu Pro Gln Leu Lys Gly Val Thr Ala Thr Arg Val Leu Glu Ala
                    245                 250                 255

<210> SEQ ID NO 11
<211> LENGTH: 248
<212> TYPE: PRT
<213> ORGANISM: Acinetobacter baumannii

<400> SEQUENCE: 11

Leu Asp Pro Val Met Thr Met Thr Ser Ser Pro Phe His Asn Ser Ser
    1               5                   10                  15

Arg Ile Leu Leu Pro Ala Leu Gln Trp Gly Val Asp Tyr Glu Val Ile
                    20                  25                  30

Pro Glu Lys Tyr His Ala Phe Val Thr Gly Thr Leu Met Leu Val Leu
                35                  40                  45

Ser Trp Ile Gly Lys Lys Ile Ser Gln Pro Arg Leu Asn Gly Pro Gln
        50                  55                  60

Leu Thr Gly Gln Leu Val Gly Ile Asn Ser Leu Leu Asn Ile Pro Thr
    65                  70                  75                  80

Pro Thr Lys Pro Asp Glu Leu Ala Trp Ile Ala Glu Ala Lys Lys His
                    85                  90                  95

Leu Gly Leu Gln Glu Ile Pro Gly Lys Gln His Asn Pro Thr Ile Leu
                100                 105                 110

Lys Trp Leu Ser Glu Leu Lys Ala Trp Trp Ala Asp Asp Glu Thr Ala
            115                 120                 125

Trp Cys Gly Thr Phe Val Ala His Cys Leu Lys Ser Ala Gly Ile Ala
        130                 135                 140

Tyr Ser Lys His Trp Tyr Arg Ala Leu Asp Tyr Val Asn Tyr Gly Thr
    145                 150                 155                 160

Lys Leu Ala Lys Pro Ala Tyr Gly Cys Val Ala Ile Lys Thr Arg Lys
                    165                 170                 175

Gly Gly Gly Arg Val Cys Phe Val Val Gly Arg Asp Lys Lys Ser Gly
                180                 185                 190

Lys Leu Val Cys Leu Gly Gly Asn Gln Ser Asn Lys Val Cys Tyr Ala
            195                 200                 205

Leu Tyr Asn Asp Ser Asp Phe Gln Glu Phe Arg Trp Tyr Gly Arg Thr
        210                 215                 220

Thr Gln Pro Ala Ser Lys Arg Tyr Thr Leu Pro Gln Leu Lys Gly Val
    225                 230                 235                 240

Thr Ala Thr Arg Val Leu Glu Ala
                    245

<210> SEQ ID NO 12
<211> LENGTH: 180
<212> TYPE: PRT
<213> ORGANISM: Acinetobacter baumannii

<400> SEQUENCE: 12

Met Lys Ile Glu Gln Tyr Leu Asp Asp Leu Ile Lys Arg Val Gly Gly
    1               5                   10                  15

Tyr Val Asn Asn Pro Val Asp Arg Gly Gly Ala Thr Lys Tyr Gly Ile
```

```
                    20                  25                  30
Thr Glu Ala Val Ala Arg Glu Asn Gly Tyr Lys Gly Asn Met Lys Asp
                35                  40                  45

Leu Pro Leu Asp Val Ala Lys Ala Ile Tyr Arg Lys Gln Tyr Trp Ile
         50                  55                  60

Glu Pro Arg Phe Asp Gln Val Asn Thr Leu Ser Ser Ala Val Ala Glu
 65                  70                  75                  80

Glu Leu Leu Asp Thr Gly Val Asn Cys Gly Ile Asn Phe Ala Lys Pro
                 85                  90                  95

Leu Leu Gln Arg Ala Leu Asn Leu Leu Asn Asn Gln Gly Lys Ala Gly
                100                 105                 110

Tyr Ala Asp Leu Lys Val Asp Gly Val Tyr Gly Ser Asn Thr Leu Gly
                115                 120                 125

Ala Leu Lys Thr Tyr Leu Ala Lys Arg Gly Lys Glu Gly Glu Lys Val
                130                 135                 140

Leu Val Arg Val Leu Asn Ile Met Gln Gly Gln Arg Tyr Ile Glu Ile
145                 150                 155                 160

Cys Glu Arg Asn Lys Ser Gln Glu Gln Phe Phe Tyr Gly Trp Ile Ala
                165                 170                 175

Asn Arg Ile Gly
            180

<210> SEQ ID NO 13
<211> LENGTH: 180
<212> TYPE: PRT
<213> ORGANISM: Acinetobacter baumannii

<400> SEQUENCE: 13

Met Lys Ile Glu Gln Tyr Leu Asp Asp Leu Ile Lys Arg Glu Gly Gly
 1               5                  10                  15

Tyr Val Asn Asn Pro Val Asp Arg Gly Gly Ala Thr Lys Tyr Gly Ile
                20                  25                  30

Thr Glu Ala Val Ala Arg Glu Asn Gly Tyr Lys Gly Asn Met Lys Asp
                35                  40                  45

Leu Pro Leu Asp Val Ala Lys Ala Ile Tyr Arg Lys Gln Tyr Trp Ile
         50                  55                  60

Glu Pro Arg Phe Asp Gln Val Asn Thr Leu Ser Ser Ala Val Ala Glu
 65                  70                  75                  80

Glu Leu Leu Asp Thr Gly Val Asn Cys Gly Ile Asn Phe Ala Lys Pro
                 85                  90                  95

Leu Leu Gln Arg Ala Leu Asn Leu Leu Asn Asn Gln Gly Lys Ala Gly
                100                 105                 110

Tyr Ala Asp Leu Lys Val Asp Gly Val Tyr Gly Ser Asn Thr Leu Gly
                115                 120                 125

Ala Leu Lys Thr Tyr Leu Ala Lys Arg Gly Lys Glu Gly Glu Lys Val
                130                 135                 140

Leu Val Arg Val Leu Asn Ile Met Gln Gly Gln Arg Tyr Ile Glu Ile
145                 150                 155                 160

Cys Glu Arg Asn Lys Ser Gln Glu Gln Phe Phe Tyr Gly Trp Ile Ala
                165                 170                 175

Asn Arg Ile Gly
            180

<210> SEQ ID NO 14
<211> LENGTH: 180
```

```
<212> TYPE: PRT
<213> ORGANISM: Acinetobacter baumannii

<400> SEQUENCE: 14

Met Lys Ile Glu Gln Tyr Leu Asp Asp Leu Ile Lys Arg Glu Gly Gly
1               5                   10                  15

Tyr Val Asn Asn Pro Val Asp Arg Gly Gly Ala Thr Lys Tyr Gly Ile
            20                  25                  30

Thr Glu Ala Val Ala Arg Glu Asn Gly Tyr Lys Gly Asn Met Lys Asp
        35                  40                  45

Leu Pro Leu Asp Val Ala Lys Ala Ile Tyr Arg Lys Gln Tyr Trp Ile
    50                  55                  60

Glu Pro Arg Phe Asp Gln Val Asn Thr Leu Ser Ser Ala Val Ala Glu
65                  70                  75                  80

Glu Leu Leu Asp Thr Gly Val Asn Cys Gly Ile Asn Phe Ala Lys Pro
                85                  90                  95

Leu Leu Gln Arg Ala Leu Asn Leu Leu Asn Asn Gln Gly Lys Ala Gly
            100                 105                 110

Tyr Ala Asp Leu Lys Val Asp Gly Val Tyr Gly Ser Asn Thr Leu Gly
        115                 120                 125

Ala Leu Lys Thr Tyr Leu Ala Lys Arg Gly Lys Glu Gly Glu Lys Val
    130                 135                 140

Leu Val Arg Val Leu Asn Ile Met Gln Gly Gln Arg Tyr Ile Glu Ile
145                 150                 155                 160

Cys Glu Arg Asn Lys Ser Gln Glu Gln Phe Phe Tyr Gly Trp Ile Ala
                165                 170                 175

Asn Arg Ile Gly
            180

<210> SEQ ID NO 15
<211> LENGTH: 180
<212> TYPE: PRT
<213> ORGANISM: Acinetobacter baumannii

<400> SEQUENCE: 15

Met Lys Ile Glu Gln Tyr Leu Asp Asp Leu Ile Lys Arg Glu Gly Gly
1               5                   10                  15

Tyr Val Asn Asn Pro Val Asp Arg Gly Gly Ala Thr Lys Tyr Gly Ile
            20                  25                  30

Thr Glu Ala Val Ala Arg Glu Asn Gly Tyr Lys Gly Asn Met Lys Asp
        35                  40                  45

Leu Pro Leu Asp Val Ala Lys Ala Ile Tyr Arg Lys Gln Tyr Trp Ile
    50                  55                  60

Glu Pro Arg Phe Asp Gln Val Asn Thr Leu Ser Ser Ala Val Ala Glu
65                  70                  75                  80

Glu Leu Leu Asp Thr Gly Val Asn Cys Gly Ile Asn Phe Ala Lys Pro
                85                  90                  95

Leu Leu Gln Arg Ala Leu Asn Leu Leu Asn Asn Gln Gly Lys Ala Gly
            100                 105                 110

Tyr Ala Asp Leu Lys Val Asp Gly Val Tyr Gly Ser Ser Thr Leu Gly
        115                 120                 125

Ala Leu Lys Thr Tyr Leu Ala Lys Arg Gly Lys Glu Gly Glu Lys Val
    130                 135                 140

Leu Val Arg Val Leu Asn Ile Met Gln Gly Gln Arg Tyr Ile Glu Ile
145                 150                 155                 160
```

```
Cys Glu Arg Asn Pro Lys Gln Glu Gln Phe Phe Tyr Gly Trp Ile Ala
                165                 170                 175

Asn Arg Ile Gly
            180

<210> SEQ ID NO 16
<211> LENGTH: 168
<212> TYPE: PRT
<213> ORGANISM: Acinetobacter baumannii

<400> SEQUENCE: 16

Met Ser Asn Lys Thr Lys Ile Ile Val Thr Thr Leu Ser Ala Ser Ala
1               5                   10                  15

Leu Phe Phe Ala Ser Leu Ile Gly Tyr Glu Gly Tyr Lys Ser Lys Pro
                20                  25                  30

Tyr Leu Asp Ser Ala Lys Val Ala Thr Ile Gly Ile Gly Ser Thr Ser
            35                  40                  45

Tyr Glu Asn Gly Thr Lys Val Lys Met Thr Asp Lys Pro Ile Thr Lys
        50                  55                  60

Glu Arg Ala Val Gln Ile Ala Lys Ala His Ile Ala Lys Asp Glu Val
65                  70                  75                  80

Ala Phe Arg Lys Ser Leu Gln Gly Val Arg Leu Thr Gln Thr Glu Tyr
                85                  90                  95

Asp Val Tyr Leu Asp Phe Val Tyr Asn Tyr Gly Gln Ala Asn Trp Asn
            100                 105                 110

Gly Ser Ser Met Leu Arg Asn Leu Lys Ala Gly Gln Tyr Lys Gln Ala
        115                 120                 125

Cys Ala Ser Leu Leu Lys Tyr Lys Tyr Val Ala Lys Arg Asp Cys Ser
130                 135                 140

Ile Arg Ser Asn Gly Cys Tyr Gly Val Trp Thr Arg Gln Gln Asp Cys
145                 150                 155                 160

Tyr Ser Lys Cys Met Ala Val Gln
                165

<210> SEQ ID NO 17
<211> LENGTH: 168
<212> TYPE: PRT
<213> ORGANISM: Acinetobacter baumannii

<400> SEQUENCE: 17

Met Ser Asn Lys Thr Lys Ile Ile Val Thr Thr Leu Ser Ala Ser Ala
1               5                   10                  15

Leu Phe Phe Ala Ser Leu Ile Gly Tyr Glu Gly Tyr Lys Ser Lys Pro
                20                  25                  30

Tyr Leu Asp Ser Ala Lys Val Ala Thr Ile Gly Ile Gly Ser Thr Ser
            35                  40                  45

Tyr Glu Asn Gly Thr Lys Val Lys Met Thr Asp Lys Pro Ile Thr Lys
        50                  55                  60

Glu Arg Ala Val Gln Ile Ala Lys Ala His Ile Ala Lys Asp Glu Val
65                  70                  75                  80

Ala Phe Arg Lys Ser Leu Gln Gly Val Arg Leu Thr Gln Thr Glu Tyr
                85                  90                  95

Asp Val Tyr Leu Asp Phe Val Tyr Asn Tyr Gly Gln Ala Asn Trp Asn
            100                 105                 110

Gly Ser Ser Met Leu Arg Asn Leu Lys Ala Gly Gln Tyr Lys Gln Ala
        115                 120                 125
```

```
Cys Ala Ser Leu Leu Lys Tyr Lys Tyr Val Ala Lys Arg Asp Cys Ser
            130                 135                 140

Ile Arg Ser Asn Gly Cys Tyr Gly Val Trp Thr Arg Gln Gln Asp Arg
145                 150                 155                 160

Tyr Ser Lys Cys Met Ala Val Gln
                165
```

<210> SEQ ID NO 18
<211> LENGTH: 180
<212> TYPE: PRT
<213> ORGANISM: Acinetobacter baumannii

<400> SEQUENCE: 18

```
Met Lys Ile Glu Gln Tyr Leu Asp Asp Leu Ile Lys Arg Glu Gly Gly
1               5                   10                  15

Tyr Val Asn Asn Pro Val Asp Arg Gly Gly Ala Thr Lys Tyr Gly Ile
            20                  25                  30

Thr Glu Ala Val Ala Arg Glu Asn Gly Tyr Lys Gly Asn Met Lys Asp
        35                  40                  45

Leu Pro Leu Asp Val Ala Lys Ala Ile Tyr Arg Lys Gln Tyr Trp Ile
    50                  55                  60

Glu Pro Arg Phe Asp Gln Val Asn Thr Leu Ser Ser Ala Val Ala Glu
65                  70                  75                  80

Glu Leu Leu Asp Thr Gly Val Asn Cys Gly Ile Asn Phe Ala Lys Pro
                85                  90                  95

Leu Leu Gln Arg Ala Leu Asn Leu Leu Asn Asn Gln Gly Lys Ala Gly
            100                 105                 110

Tyr Ala Asp Leu Lys Val Asp Gly Val Tyr Gly Ser Ser Thr Leu Gly
        115                 120                 125

Ala Leu Lys Thr Tyr Leu Ala Lys Arg Gly Lys Glu Gly Glu Lys Val
    130                 135                 140

Leu Val Arg Val Leu Asn Ile Met Gln Gly Gln Arg Tyr Ile Glu Ile
145                 150                 155                 160

Cys Glu Arg Asn Pro Lys Gln Glu Gln Phe Phe Tyr Gly Trp Ile Ala
                165                 170                 175

Asn Arg Ile Gly
            180
```

<210> SEQ ID NO 19
<211> LENGTH: 211
<212> TYPE: PRT
<213> ORGANISM: Acinetobacter baumannii

<400> SEQUENCE: 19

```
Leu Thr Lys Asn Leu Ser Leu His Phe Trp Ile Asn Ile Asn Ile Lys
1               5                   10                  15

Phe Thr Asp Gln Leu Val Ala Phe Leu Arg Leu Lys Glu Ser Glu Met
            20                  25                  30

Lys Ile Glu Gln Tyr Leu Asp Asp Leu Ile Lys Arg Glu Gly Gly Tyr
        35                  40                  45

Val Asn Asn Pro Val Asp Arg Gly Gly Ala Thr Lys Tyr Gly Ile Thr
    50                  55                  60

Glu Ala Val Ala Arg Glu Asn Gly Tyr Lys Gly Asn Met Lys Asp Leu
65                  70                  75                  80

Pro Leu Asp Val Ala Lys Ala Ile Tyr Arg Lys Gln Tyr Trp Ile Glu
                85                  90                  95
```

```
Pro Arg Phe Asp Gln Val Asn Thr Leu Ser Ser Ala Val Ala Glu Glu
            100                 105                 110

Leu Leu Asp Thr Gly Val Asn Cys Gly Ile Asn Phe Ala Lys Pro Leu
        115                 120                 125

Leu Gln Arg Ala Leu Asn Leu Leu Asn Asn Gln Gly Lys Ala Gly Tyr
    130                 135                 140

Ala Asp Leu Lys Val Asp Gly Val Tyr Gly Ser Asn Thr Leu Gly Ala
145                 150                 155                 160

Leu Lys Thr Tyr Leu Ala Lys Arg Gly Lys Glu Gly Glu Lys Val Leu
                165                 170                 175

Val Arg Val Leu Asn Ile Met Gln Gly Gln Arg Tyr Ile Glu Ile Cys
            180                 185                 190

Glu Arg Asn Lys Ser Gln Glu Gln Phe Phe Tyr Gly Trp Ile Ala Asn
        195                 200                 205

Arg Ile Gly
        210

<210> SEQ ID NO 20
<211> LENGTH: 180
<212> TYPE: PRT
<213> ORGANISM: Acinetobacter baumannii

<400> SEQUENCE: 20

Met Lys Ile Glu Gln Tyr Leu Asp Asp Leu Ile Lys Arg Glu Gly Gly
1               5                   10                  15

Tyr Val Asn Asn Pro Val Asp Arg Gly Gly Ala Thr Lys Tyr Gly Ile
            20                  25                  30

Thr Glu Ala Val Ala Arg Glu Asn Gly Tyr Lys Gly Asn Met Lys Asp
        35                  40                  45

Leu Pro Leu Asp Val Ala Lys Ala Ile Tyr Arg Lys Gln Tyr Trp Ile
    50                  55                  60

Glu Pro Arg Phe Asp Gln Val Asn Thr Leu Ser Ser Ala Val Ala Glu
65                  70                  75                  80

Glu Leu Leu Asp Thr Gly Val Asn Cys Gly Ile Asn Phe Ala Lys Pro
                85                  90                  95

Leu Leu Gln Arg Ala Leu Asn Leu Leu Asn Asn Gln Gly Lys Ala Gly
            100                 105                 110

Tyr Thr Asp Leu Lys Val Asp Gly Val Tyr Gly Ser Ser Thr Leu Gly
        115                 120                 125

Ala Leu Lys Thr Tyr Leu Ala Lys Arg Gly Lys Glu Gly Glu Lys Val
    130                 135                 140

Leu Val Arg Val Leu Asn Ile Met Gln Gly Gln Arg Tyr Ile Glu Ile
145                 150                 155                 160

Cys Glu Arg Asn Pro Lys Gln Glu Gln Phe Phe Tyr Gly Trp Ile Ala
                165                 170                 175

Asn Arg Ile Gly
            180

<210> SEQ ID NO 21
<211> LENGTH: 146
<212> TYPE: PRT
<213> ORGANISM: Acinetobacter baumannii

<400> SEQUENCE: 21

Met Lys Thr Ser Asn Ser Gly Ile Asn Leu Ile Lys Gly Phe Glu Gly
1               5                   10                  15
```

```
Lys Arg Leu Lys Ala Tyr Asp Asp Gly Val Gly Val Trp Thr Ile Gly
         20                  25                  30

Phe Gly Thr Ile Lys Tyr Pro Asn Gly Val Arg Val Lys Lys Gly Asp
             35                  40                  45

Ile Cys Thr Glu Ser Gln Ala Glu Gly Tyr Leu Arg Asn Asp Leu Val
 50                  55                  60

Ala Phe Glu Asn Ala Ile Asn Arg Leu Val Lys Val Pro Leu Asn Gln
 65                  70                  75                  80

Asn Gln Phe Asp Ala Leu Ala Ser Phe Thr Tyr Asn Leu Gly Glu Gly
                 85                  90                  95

Asn Leu Ser Lys Ser Thr Leu Leu Lys Lys Leu Asn Ala Lys Asp Tyr
            100                 105                 110

Lys Gly Ala Ala Ala Glu Phe Pro Lys Trp Asn Lys Ala Gly Gly Arg
        115                 120                 125

Val Leu Ala Gly Leu Val Lys Arg Arg Lys Ala Glu Met Glu Leu Phe
130                 135                 140

Leu Lys
145

<210> SEQ ID NO 22
<211> LENGTH: 441
<212> TYPE: DNA
<213> ORGANISM: Acinetobacter baumannii

<400> SEQUENCE: 22
gtgaaaacaa gtaacccagg agtggattta atcaaaggct ttgaaggtct acgattgaaa      60
gcctatgacg atggtgtggg cgtttggacc attggctttg caccatcaa atacccgaac     120 ggtgtgcgag tcaaaaaagg cgatacatgc actgaatctc aagcggaaga atacctt cgc   180 aatgacttag ttgtatttga agcgctatc aatcgtttgg tgaaagttcc gcttaatcaa    240
aaccaattcg atgctttggc ctcattcact acaaccttg gtgagggcaa tcttagtata    300
tcaactttgc taaaaaagct taatgccaaa gactataaag gtgctgcagc tgaatttcct    360
aaatggaata aggcgggtgg tcgtgtcttg gctggattag ttaaacgtcg caaagctgaa    420
atggagttat ttttaaaatg a                                               441

<210> SEQ ID NO 23
<211> LENGTH: 570
<212> TYPE: DNA
<213> ORGANISM: Acinetobacter baumannii

<400> SEQUENCE: 23
ttaagcctct gaaacactcg taacagaaac gattttaggg actggtaaat cgtatcggtg     60
agcagctggt ttacttgttt tgccatacca cataaaggct tcaaaagccg aaacgtcata   120
tactgcaaaa caaactttat ttgactgatt accacctaag caaattaatt taccagtagg   180
tgttttacca acaacgaaag ttacatggcc accgccctct cttgatttta ccgcaacaca   240
cccataacaa ggcttgtgta atttgactcc gccttctttg atgtattcaa gtgcggcata   300
ccagttgaaa ggataaaagc ctggtgggc ctttgttcct gatttataag ttttggaacg    360
cgagtttaca cttcctcttt gaaatcccgc cgtttggaga cagtgcgcaa cgaatgttcc    420
gcaccatgca gtttcatcgt caagccaaga ggactttaag tccttcagcc atttgatgat   480
tgtctggttg tgtttgggc cggcgatttc agccaaccct atgtgacggg gagcctctgc   540
gatccacggt aattctggat ttgcactcat                                      570
```

<210> SEQ ID NO 24
<211> LENGTH: 558
<212> TYPE: DNA
<213> ORGANISM: Acinetobacter baumannii

<400> SEQUENCE: 24

| | | | | | |
|---|---|---|---|---|---|
| ctgaaggaaa | ccgaaatgaa | tattgaaaaa | tatcttgatg | aattaattaa | gcgtgaaggc | 60 |
| gggtatgtaa | ataacccagc | tgatcggggc | ggtgcaacta | aatatggcat | cacacaagct | 120 |
| gttgcgcgtg | aaaatggctg | gaatggcaat | atgaaagatt | tgccgcttga | tgtggccaaa | 180 |
| gctatttaca | agaagcaata | ctggacagct | ccgcgatttg | accaagtaaa | tgctgtttct | 240 |
| tctgcagtag | ctgaagagct | tctagacact | ggtgtgaatt | gcggtaccgg | atttgcaaaa | 300 |
| cctcttttac | aacgagcttt | gaacttgctt | aataaccaag | gtaaagctgg | atatgcagat | 360 |
| ttagaggttg | atggtgttta | tggctcagca | acgctaggtg | cccttaaaac | atacttgtca | 420 |
| aaacgtggga | agaaggtga | gaaggttctg | gtgcgagtgc | tcaatattat | gcaagggcaa | 480 |
| cgctacattg | aaatctgtga | gcgtaatcca | aagcaggaac | agttttcta | tggctggatt | 540 |
| gctaaccgga | tcggctag | | | | | 558 |

<210> SEQ ID NO 25
<211> LENGTH: 261
<212> TYPE: DNA
<213> ORGANISM: Acinetobacter baumannii

<400> SEQUENCE: 25

| | | | | | |
|---|---|---|---|---|---|
| tcactgcgct | cctatacatt | ttgcgtgtcg | ttctacttgt | ctggtccaga | cgccataaca | 60 |
| cccgttttta | cgaacagagc | aatcgcgctt | tgcaacgtac | ttatatttaa | gtaaagagtc | 120 |
| gcaagctgct | ttatattgac | cagcctttaa | atgcttaagc | attgatgatt | ttgcgaatgt | 180 |
| tggcacaccg | tattgatacg | tgaaatcaag | gtataggtca | tattcagtct | gtgataattc | 240 |
| ggctcgagtt | gtggaaggca | g | | | | 261 |

<210> SEQ ID NO 26
<211> LENGTH: 588
<212> TYPE: DNA
<213> ORGANISM: Acinetobacter baumannii

<400> SEQUENCE: 26

| | | | | | |
|---|---|---|---|---|---|
| tcatataaca | actcgattgg | cgatccaacc | atagaaaaac | tgttcctggc | taggattgcg | 60 |
| ttcacagatt | tcaatgtaac | gttgcccttg | catgatatta | agaacacgca | ccaggacttt | 120 |
| ttcgccgtct | tttccacgct | tggccagata | agttttgagt | gcattaagag | ttgctggacc | 180 |
| ataaattccg | tcaactgtta | aatctggcca | acctgcttta | ccttggttat | tcagcaaatt | 240 |
| taaagcacgc | tgtaagagtg | gttttgcaaa | tccggtaccg | caatttaccc | cagtatctaa | 300 |
| aagctcttca | gcaactaacg | agctaattac | attcacttga | tcaaatcgcg | gatctgtcca | 360 |
| atactgcttt | ttataaatgg | cttttggcca | catcaagcggt | aaatctttca | tgttgccctt | 420 |
| aaagccgtta | gtacgtgcta | ctgcttcagt | aataccgtac | tttgtttcac | cgcctcgatc | 480 |
| tgctggttg | tttacgtacc | cgccctcacg | cttaattaac | tcgtccagat | attgttcaat | 540 |
| gttcatttcg | gtttccttca | gatgtaaaaa | accgcccgaa | ggcggcat | | 588 |

<210> SEQ ID NO 27
<211> LENGTH: 570
<212> TYPE: DNA
<213> ORGANISM: Acinetobacter baumannii

<400> SEQUENCE: 27

```
ttaagcctct gaaacactcg taacagaaac gattttagg actggtaaat cgtatcggtg      60
agcagctggt ttacttgttt tgccatacca cataaaggct tcaaaagccg aaacgtcata    120
tactgcaaaa caaactttat ttgactgatt accacctaag caaattaatt taccagtggg    180
tgttttacca acaacgaaag ttacatggcc accgccctct cttgatttta ccgcaacaca    240
cccataacaa ggcttgtcta atttgactcc gccttcttg atgtattcaa gtgcggcata     300
ccagttgaaa ggataaaagc ctggtggggc ctttgttcct gatttataag ttttggaacg    360
cgagtttaca cttcctcttt gaaatcccgc cgtttggaga cagtgcgcaa cgaatgttcc    420
gcaccatgca gtttcatcgt caagccaaga ggactttaag tccttcagcc atttgatgat    480
tgtctggttg tgtttgggggc cggcgatttc agccaaccct atgtgacggc gagcctctgc   540
gatccacggt aattctggat ttgcactcat                                     570
```

<210> SEQ ID NO 28
<211> LENGTH: 771
<212> TYPE: DNA
<213> ORGANISM: Acinetobacter baumannii

<400> SEQUENCE: 28

```
atgaagttaa ttgaaaacaa tgcttggcag tatctatctg ttaagttacc cgccgtaggt     60
gcattcatca tgctaatttt attgccagca ctacaatggg gtgttgatta tgaagttatt    120
cctgaaaaat atcatgcatt tgttactggt actttgatgc ttgttctgtc atggattgga    180
aagaaaattt ctcaaccacg acttaatggc ccgcaattaa caggccagtt agtagggatc    240
aattctttat tgaatatccc aacaccaaca aagcctgatg aattagcttg gattgcggaa    300
gcaaaaaagc atcttggcct tcaagaaata cctggtaaac agcataaccc aactatttta    360
aaatggctct cggagctaaa ggcttggtgg gctgacgatg aaacggcttg gtgtgggacc    420
ttcgttgcac attgcttgaa atcagctgga attgcttatc ctaagcattg gtaccgtgca    480
ttggattatg tgaattatgg tacaaaatta gctaaaccc cttacggttg tgtagctatt    540
aaaactcgaa agggtggtgg gcatgtttgt tttgtagttg gccgtgacaa aaagtctgga    600
aagttagtat gccttggagg caatcagtca aataaagttt gttatgcact ttataatgac    660
tctgactttc aagaattcag atggtatggt cgtacaactc aaccagcaag taagcgttat    720
acattgccac aattaaaagg cgtaacagct actagggttt tggaagccta a             771
```

<210> SEQ ID NO 29
<211> LENGTH: 771
<212> TYPE: DNA
<213> ORGANISM: Acinetobacter baumannii

<400> SEQUENCE: 29

```
ttaggcttcc aaaaccctag tagctgttac gccttttaat tgtggcaatg tataacgctt     60
acttgctggt tgagttgtac gaccatacca tctgaattct tgaaagtcag agtcattata    120
aagtgcataa caaactttat ttgactgatt gcctccaagg catactaact ttccagactt    180
tttgtcacgg ccaactacaa aacaaacatg cccaccaccc tttcgagttt taatagctac    240
acaaccgtaa gcgggtttag ctaattttgt accataattc acataatcca atgcacggta    300
ccaatgctta ggataagcaa ttccagctga tttcaagcaa tgtgcaacga aggtcccaca    360
ccaagccgtt tcatcgtcag cccaccaagc ctttagctcc gagagccatt ttaaaatagt    420
```

```
tgggttatgc tgtttaccag gtatttcttg aaggccaaga tgcttttttg cttctgcaat      480
ccaagctaat tcatcaggct ttgttggtgt tgggatattc aataaagaat tgatccctac      540
taactggcct gttaattgcg ggccattaag tcgtggttga gaaattttct ttccaatcca      600
tgacagaaca agcatcaaag taccagtaac aaatgcatga tattttttcag gaataacttc     660 ataatcaaca ccccattgta gtgctggcaa taaaattagc atgatgaatg cacctacggc      720
gggtaactta acagatagat actgccaagc attgttttca attaacttca t               771
```

<210> SEQ ID NO 30
<211> LENGTH: 771
<212> TYPE: DNA
<213> ORGANISM: Acinetobacter baumannii

<400> SEQUENCE: 30

```
ttaggcttcc aaaaccctag tagctgttac gccttttaat tgtggcaatg tataacgctt       60
acctgctggt tgagttgtac gaccatacca tctgaattct tgaaagtcag agtcattata     120
aagtgcataa caaactttat ttgactgatt gcctccaagg catactaact ttccagactt     180
tttgtcacgg ccaactacaa aacaaacatg cccaccaccc tttcgagttt taatagctac     240
acaaccgtaa gcgggtttag ctaattttgt accataattc acataatcca atgcacggta     300
ccaatgctta ggataagcaa ttccagctga tttcaagcaa tgtgcaacga aggtcccaca     360
ccaagccgtt tcatcgtcag cccaccaagc ctttagctcc gagagccatt ttaaaatagt     420
tgggttatgc tgtttaccag gtatttcttg aaggccaaga tgcttttttg cttctgcaat     480
ccaagctaat tcatcaggct ttgttggtgt tgggatattc aataaagaat tgatccctac     540
taactggcct gttaattgcg ggccattaag tcgtggttga gaaattttct ttccaatcca     600
tgacagaaca agcatcaaag taccagtaac aaatgcatga tgttttttcag gaataacttc    660 ataatcaaca ccccattgta gtgctggcaa taaaattagc atgatgaatg cacctacggc     720
gggtaactta acagatagat actgccaagc attgttttca attaacttca t              771
```

<210> SEQ ID NO 31
<211> LENGTH: 771
<212> TYPE: DNA
<213> ORGANISM: Acinetobacter baumannii

<400> SEQUENCE: 31

```
atgaagttaa ttgaaaacaa tgcttggcag tatctatctg tcaagttacc cgccgtaggt       60
gcattcatca tgctaatttt attgccagca ctacaatggg gtgttgatta tgaagttatt     120
cctgaaaaat atcatgcatt tgttactggt actttgatgc ttgttctgtc atggattgga     180
aagaaaattt ctcaaccacg acttaatggc ccgcaattaa caggccagtt agtagggatc     240
aattctttat tgaatatccc aacaccaaca aagcctgatg aattagcttg gattgcagaa     300
gcaaaaaagc atcttggcct tcaagaaata cctggtaaac agcataaccc aactatttta     360
aaatggctct cggagctaaa ggcttggtgg gctgacgatg aaacggcttg gtgtgggacc     420
ttcgttgcac attgcttgaa atcagctgga attgcttatc ctaagcattg gtaccgtgca     480
ttggattatg tgaattatgg tacaaaatta gctaaacccg cttacggttg tgtagctatt     540
aaaactcgaa agggtggtgg gcatgttttgt tttgtagttg gccgtgacaa aaagtctgga     600
aagttagtat gccttggagg caatcagtca aataaagttt gttatgcact ttataatgac     660
tctgactttc aagaattcag atggtatggt cgtacaactc aaccagcaag taagcgttat     720
acattgccac aattaaaagg cgtaacagct actagggttt tggaagccta a              771
```

<210> SEQ ID NO 32
<211> LENGTH: 747
<212> TYPE: DNA
<213> ORGANISM: Acinetobacter baumannii

<400> SEQUENCE: 32

```
ctggatccgg tgatgacgat gacaagctcg cccttccaca actcgagccg aattttattg        60
ccagcactac aatggggtgt tgattatgaa gttattcctg aaaaatatca tgcatttgtt       120
actggtactt tgatgcttgt tctgtcatgg attggaaaga aatttctca accacgactt       180 aatggcccgc aattaacagg ccagttagta gggatcaatt ctttattgaa tatcccaaca       240
ccaacaaagc ctgatgaatt agcttggatt gcagaagcaa aaaagcatct tggccttcaa       300
gaaatacctg gtaaacagca taacccaact attttaaaat ggctctcgga gctaaaggct       360
tggtgggctg acgatgaaac ggcttggtgt gggaccttcg ttgcacattg cttgaaatca       420 gctgaattg cttattctaa gcattggtac cgtgcattgg attatgtgaa ttatggtaca       480
aaattagcta aacccgctta cggttgtgta gctattaaaa ctcgaaaggg tggtgggcgt       540
gtttgttttg tagttggccg tgacaaaaag tctggaaagt tagtatgcct tggaggcaat       600
cagtcaaata aagtttgtta tgcactttat aatgactctg actttcaaga attcagatgg       660
tatggtcgta caactcaacc agcaagtaag cgttatacat tgccacaatt aaaaggcgta       720
acagctacta gggttttgga agcctaa                                             747
```

<210> SEQ ID NO 33
<211> LENGTH: 543
<212> TYPE: DNA
<213> ORGANISM: Acinetobacter baumannii

<400> SEQUENCE: 33

```
ctagccgatc cggttagcga tccagccata aaaaaactgc tcttggcttt tattacgttc        60
acagatttca atgtatcgtt ggccttgcat aatatttaac acgcgcacta agacctttc        120 gccttctttg ccacgtttgg ccaagtaagt ttttagagct cctaaagtgt tagaaccata       180
aacgccatca accttcaagt ctgcataacc agctttacct tgattgttaa gcaagttcaa       240
agcacgttgt aaaagtggtt ttgcaaagtt gataccacag ttcacaccag tgtctaaaag       300
ttcttcagct actgcagagc taagagtatt aacctgatca aaacgtggct ctatccagta       360
ctgtttccga taaattgctt tggccacatc aagaggcaaa tctttcatat tgcccttata       420
gccgttttca cgtgctacag cttcagtaat accgtatttg gtagcacctc ctcgatctac       480
tggattattt acataaccgc ctacgcgttt aatcaaatca tcaagatatt gttcaatttt       540
cat                                                                       543
```

<210> SEQ ID NO 34
<211> LENGTH: 543
<212> TYPE: DNA
<213> ORGANISM: Acinetobacter baumannii

<400> SEQUENCE: 34

```
atgaaaattg aacaatatct tgatgatttg attaaacgcg aaggcggtta tgtaaataat        60
ccagtggatc gaggaggtgc taccaaatac ggtattactg aagctgtagc acgtgaaaac       120
ggctataagg gcaatatgaa agatttgcct cttgatgtgg ccaaagcaat ttatcggaaa       180
cagtactgga tagagccacg ttttgatcag gttaatactc ttagctctgc agtagctgaa       240
```

```
gaacttttag acactggtgt gaactgtggt atcaactttg caaaaccact tttacaacgt    300
gctttgaact tgcttaacaa tcaaggtaaa gctggttatg cagacttgaa ggttgatggc    360
gtttatggtt ctaacacttt aggagctcta aaaacttact tggccaaacg tggcaaagaa    420
ggcgaaaagg tattagtgcg cgtgttaaat attatgcaag ccaacgata cattgaaatc     480 tgtgaacgta ataaaagcca agagcagttt ttttatggct ggatcgctaa ccggatcggc    540
tag                                                                  543
```

```
<210> SEQ ID NO 35
<211> LENGTH: 543
<212> TYPE: DNA
<213> ORGANISM: Acinetobacter baumannii

<400> SEQUENCE: 35
atgaaaattg aacaatatct tgatgatttg attaaacgcg aaggtggtta tgtaaataat    60
ccagtagatc gaggaggtgc taccaaatac ggtattactg aagctgtagc acgtgaaaac    120
ggctataagg gcaatatgaa agatttgcct cttgatgtgg ccaaagcaat ttatcggaaa    180
cagtactgga tagagccacg ttttgatcag gttaatactc ttagctctgc agtagctgaa    240
gaacttttag acactggtgt gaactgtggt atcaactttg caaaaccact tttacaacgt    300
gctttgaact tgcttaacaa tcaaggtaaa gctggttatg cagacttgaa ggttgatggc    360
gtttatggtt ctaacacttt aggagctcta aaaacttact tggccaaacg tggcaaagaa    420
ggcgaaaagg tcttagtgcg cgtgttaaat attatgcaag ccaacgata cattgaaatc     480 tgtgaacgta ataaaagcca agagcagttt ttttatggct ggatcgctaa ccggatcggc    540
tag                                                                  543
```

```
<210> SEQ ID NO 36
<211> LENGTH: 543
<212> TYPE: DNA
<213> ORGANISM: Acinetobacter baumannii

<400> SEQUENCE: 36
ctagccgatc cggttagcaa tccagccata gaagaattgc tcttgcttgg gattacgctc    60
acaaatttcg atatatcgct ggccttgcat gatattaaga actcgcacta ggactttctc    120
accttctttc ccacgtttgg ccaagtaagt tttgagagct cctaatgtgc tagaaccata    180
aacgccatca accttcaagt ctgcataacc agctttacct tgattgttaa gcaagttcaa    240
agcacgttgt aaaagtggtt ttgcaaagtt gataccacag ttcacaccag tgtctaaaag    300
ttcttcagct actgcagagc taagagtatt aacctgatca aaacgtggct ctatccagta    360
ctgtttccga taaattgctt tggccacatc aagaggcaaa tctttcatat tgcccttata    420
gccgttttca cgtgctacag cttcagtaat accgtatttg gtagcacctc ctcgatctac    480
tggattattt ataaccgc cttcgcgttt aatcaaatca tcaagatatt gttcaattt     540 cat                                                                  543
```

```
<210> SEQ ID NO 37
<211> LENGTH: 507
<212> TYPE: DNA
<213> ORGANISM: Acinetobacter baumannii

<400> SEQUENCE: 37
tcactgcacc gccatacact tgctataaca atcttgttgg cgtgtccaga caccataaca    60
accattggac cgaatcgagc aatcacgctt tgcaacatat ttgtatttca gtaatgaagc    120
```

```
acaagcttgc ttatattgcc ctgctttgag attacgaagc attgatgagc cgttccaatt        180
tgcttggcca tagttgtaaa caaagtctaa gtacacatca tattcagtct gagttagcct        240
cacgccctgc aacgacttgc gaaatgccac ctcatctttta gcaatgtgag ctttggcaat       300
ttgaacagca cgttctttg taatcggctt gtcagtcatt ttgaccttgg taccgttttc         360
ataggaagtg gatccgatac caatcgttgc cactttagcg ctatctaaat atggctttga        420
tttgtacccc tcatagccaa ttaaagatgc aaaaaaaagc gctgatgcgc ttaatgttgt        480
tactatgatt ttagtcttgt ttgacat                                            507

<210> SEQ ID NO 38
<211> LENGTH: 507
<212> TYPE: DNA
<213> ORGANISM: Acinetobacter baumannii

<400> SEQUENCE: 38
atgtcaaaca agactaaaat catagtaaca acattaagcg catcagcgct ttttttttgca       60 tctttaattg gctatgaggg gtacaaatca aagccatatt tagatagcgc taaagtggca       120
acgattggta tcggatccac ttcctatgaa acggtacca aggtcaaaat gactgacaag         180
ccgattacaa aagaacgtgc tgttcaaatt gccaaagctc acattgctaa agatgaggtg       240
gcatttcgca agtcgttgca gggcgtgagg ctaactcaga ctgaatatga tgtgtactta       300
gactttgttt acaactatgg ccaagcaaat tggaacggct catcaatgct tcgtaatctc       360
aaagcagggc aatataagca agcttgtgct tcattactga aatacaaata tgttgcaaag      420
cgtgattgct cgattcggtc caatggttgt tatggtgtct ggacacgcca acaagatcgt       480
tatagcaagt gtatggcggt gcaatga                                           507

<210> SEQ ID NO 39
<211> LENGTH: 543
<212> TYPE: DNA
<213> ORGANISM: Acinetobacter baumannii

<400> SEQUENCE: 39
ctagccgatc cggttagcaa tccagccata gaagaattgc tcttgcttag gattacgctc       60
acaaatttcg atatatcgct ggccttgcat gatattaaga actcgcacta ggactttctc      120
accttctttc ccacgtttgg ccaagtaagt tttgagagct cctaatgtgc tagaaccata      180
aacgccatca accttcaagt ctgcataacc agctttacct tgattgttaa gcaagttcaa      240
agcacgttgt aaaagtggtt ttgcaaagtt gataccacag ttcaccag tgtctaaaag       300 ttcttcagct actgcagagc taagagtatt aacctgatca aaacgtggct ctatccagta      360
ctgtttccga taaattgctt tggccacatc aagaggcaaa tctttcatat tgcccttata     420 gccgtttca cgtgctacag cttcagtaat accgtatttg gtagcaccctc ctcgatctac      480 tggattattt acataaccgc cttcgcgttt aatcaaatca tcaagatatt gttcaatttt     540
cat                                                                    543

<210> SEQ ID NO 40
<211> LENGTH: 636
<212> TYPE: DNA
<213> ORGANISM: Acinetobacter baumannii

<400> SEQUENCE: 40
ctagccgatc cggttagcga tccagccata aaaaaactgc tcttggcttt tattacgttc       60
```

```
acagatttca atgtatcgtt ggccttgcat aatatttaac acgcgcacta agacctttc        120
gccttctttg ccacgtttgg ccaagtaagt ttttagagct cctaaagtgt tagaaccata        180
aacgccatca accttcaagt ctgcataacc agctttacct tgattgttaa gcaagttcaa        240
agcacgttgt aaaagtggtt ttgcaaagtt gataccacag ttcacaccag tgtctaaaag        300
ttcttcagct actgcagagc taagagtatt aacctgatca aaacgtggct ctatccagta        360
ctgtttccga taaattgctt tggccacatc aagaggcaaa tctttcatat tgcccttata        420
gccgttttca cgtgctacag cttcagtaat accgtatttg gtagcacctc ctcgatctac        480
tggattattt acataaccgc cttcgcgttt aatcaaatca tcaagatatt gttcaatttt        540
catttcactt tcctttagac gtaaaaaagc caccagttga tccgtgaact tgatatttat        600
attgatccag aagtgcaggc tgaggttttt ggtcag                                  636
```

<210> SEQ ID NO 41
<211> LENGTH: 543
<212> TYPE: DNA
<213> ORGANISM: Acinetobacter baumannii

<400> SEQUENCE: 41

```
atgaaaattg aacaatatct tgatgatttg attaaacgcg aaggcggtta tgtaaataat         60
ccagtagatc gaggaggtgc taccaaatac ggtattactg aagctgtagc acgtgaaaac        120
ggctataagg gcaatatgaa agatttgcct cttgatgtgg ccaaagcaat ttatcggaaa        180
cagtactgga tagagccacg ttttgatcag gttaatactc ttagctctgc agtagctgaa        240
gaacttttag acactggtgt gaactgtggt atcaactttg caaaaccact tttacaacgt        300
gctttgaact tgcttaacaa tcaaggtaaa gctggttata cagacttgaa ggttgatggc        360
gtttatggtt ctagcacatt aggagctctc aaaacttact tggccaaacg tgggaaagaa        420
ggtgagaaag tcctagtgcg agttcttaat atcatgcaag ccagcgata tatcgaaatt         480
tgtgagcgta atcctaagca agagcaattc ttctatggct ggattgctaa ccggatcggc        540
tag                                                                      543
```

<210> SEQ ID NO 42
<211> LENGTH: 441
<212> TYPE: DNA
<213> ORGANISM: Acinetobacter baumannii

<400> SEQUENCE: 42

```
tcattttaaa ataactccca tttcagcttt gcgacgtttc accagtcctg ccaatacacg         60
accgccagct tgttccatt tgggaattc tgctgctgca cctttatagt ccttagcatt         120
taacttttt agcaaagtag atttgctaag attgccttcg cctaagttat aagtgaatga        180
ggccaaagca tcgaattggt tttgattaag tggtactttc accaagcgat tgatagcatt        240
ttcaaatgcg accaagtcat tgcgaagata tccttctgct tgagactcag tgcatatatc        300
gcctttttg acacgcactc cattaggata tttaattgtt ccaaatccaa tggtccaaac        360
gcccacacca tcgtcatagg ctttcaaacg tttaccttca aagcctttga ttagattgat        420
tcctgagtta cttgttttca t                                                  441
```

<210> SEQ ID NO 43
<211> LENGTH: 31
<212> TYPE: PRT
<213> ORGANISM: Acinetobacter baumannii

<400> SEQUENCE: 43

-continued

Asn Ala Lys Asp Tyr Lys Gly Ala Ala Ala Glu Phe Pro Lys Trp Asn
1               5                   10                  15

Lys Ala Gly Gly Arg Val Leu Ala Gly Leu Val Lys Arg Lys
            20                  25                  30

<210> SEQ ID NO 44
<211> LENGTH: 8
<212> TYPE: PRT
<213> ORGANISM: Artificial Sequence
<220> FEATURE:
<223> OTHER INFORMATION: Ex

<400> SEQUENCE: 44

Ser Gln Ser Arg Glu Ser Gln Cys
1               5

<210> SEQ ID NO 45
<211> LENGTH: 39
<212> TYPE: PRT
<213> ORGANISM: Artificial Sequence
<220> FEATURE:
<223> OTHER INFORMATION: P307Ex

<400> SEQUENCE: 45

Asn Ala Lys Asp Tyr Lys Gly Ala Ala Ala Glu Phe Pro Lys Trp Asn
1               5                   10                  15

Lys Ala Gly Gly Arg Val Leu Ala Gly Leu Val Lys Arg Lys Ser
            20                  25                  30

Gln Ser Arg Glu Ser Gln Cys
        35

<210> SEQ ID NO 46
<211> LENGTH: 13
<212> TYPE: DNA
<213> ORGANISM: Artificial Sequence
<220> FEATURE:
<223> OTHER INFORMATION: Primer

<400> SEQUENCE: 46
aattcggctc gag                                                        13

<210> SEQ ID NO 47
<211> LENGTH: 19
<212> TYPE: DNA
<213> ORGANISM: Artificial Sequence
<220> FEATURE:
<223> OTHER INFORMATION: Primer

<400> SEQUENCE: 47
ccatgactcg agccgaatt                                                  19

<210> SEQ ID NO 48
<211> LENGTH: 7
<212> TYPE: PRT
<213> ORGANISM: Artificial Sequence
<220> FEATURE:
<223> OTHER INFORMATION: Peptide Extension

<400> SEQUENCE: 48

Ala Glu Met Leu Phe Leu Lys
1               5

<210> SEQ ID NO 49
<211> LENGTH: 39

```
<212> TYPE: PRT
<213> ORGANISM: Artificial Sequence
<220> FEATURE:
<223> OTHER INFORMATION: P307AE-8

<400> SEQUENCE: 49

Asn Ala Lys Asp Tyr Lys Gly Ala Ala Ala Glu Phe Pro Lys Trp Asn
1               5                   10                  15
Lys Ala Gly Gly Arg Val Leu Ala Gly Leu Val Lys Arg Lys Ala
            20                  25                  30
Glu Met Glu Leu Phe Leu Lys
            35

<210> SEQ ID NO 50
<211> LENGTH: 8
<212> TYPE: PRT
<213> ORGANISM: Artificial Sequence
<220> FEATURE:
<223> OTHER INFORMATION: Peptide Extension

<400> SEQUENCE: 50

Cys Ser Gln Arg Gln Ser Glu Ser
1               5

<210> SEQ ID NO 51
<211> LENGTH: 39
<212> TYPE: PRT
<213> ORGANISM: Artificial Sequence
<220> FEATURE:
<223> OTHER INFORMATION: P307CS-8

<400> SEQUENCE: 51

Asn Ala Lys Asp Tyr Lys Gly Ala Ala Ala Glu Phe Pro Lys Trp Asn
1               5                   10                  15
Lys Ala Gly Gly Arg Val Leu Ala Gly Leu Val Lys Arg Lys Cys
            20                  25                  30
Ser Gln Arg Gln Ser Glu Ser
            35

<210> SEQ ID NO 52
<211> LENGTH: 8
<212> TYPE: PRT
<213> ORGANISM: Artificial Sequence
<220> FEATURE:
<223> OTHER INFORMATION: Peptide Extension

<400> SEQUENCE: 52

Ser Gln Ser Arg Glu Ser Gln Ala
1               5

<210> SEQ ID NO 53
<211> LENGTH: 39
<212> TYPE: PRT
<213> ORGANISM: Artificial Sequence
<220> FEATURE:
<223> OTHER INFORMATION: P307SQ-8A

<400> SEQUENCE: 53

Asn Ala Lys Asp Tyr Lys Gly Ala Ala Ala Glu Phe Pro Lys Trp Asn
1               5                   10                  15
```

```
Lys Ala Gly Gly Arg Val Leu Ala Gly Leu Val Lys Arg Arg Lys Ser
            20                  25                  30
Gln Ser Arg Glu Ser Gln Ala
            35
```

ACINETOBACTER LYSINS

CROSS-REFERENCE TO RELATED APPLICATION

This application is a United States National Phase of PCT/US2015/037962, filed Jun. 26, 2015, which claims the benefit of priority to U.S. Provisional Application Ser. No. 62/017,618, filed Jun. 26, 2014. The entire contents of which are incorporated herein by reference.

SEQUENCE LISTING

This application incorporates by reference in its entirety the sequence listing entitled "235932-406445_Sequence_Listing_ST25", (57 KB) which was created on Jan. 18, 2017, and filed electronically herewith.

FIELD

Compositions comprising a bacteriophage lytic enzyme specific for *Acinetobacter* and method for treating *Acinetobacter* infections.

BACKGROUND

*Acinetobacter baumannii-calcoaceticus* complex and other members of this species frequently colonize the human skin without harm. However, injuries to the skin from scrapes, wounds or surgery, can result in *Acinetobacter* infection of the wound, blood, soft tissues, and central nervous system. Given that >80% of *Acinetobacter* sp. are also multiply drug resistant (MDR) (at least three classes of antibiotics), these infections may result in adverse clinical outcomes, including high rates of morbidity and mortality, prolonged hospital stay, and substantial health care expenses. Military personnel and athletes have an increased the risk of injuries (from skin abrasions to severe wounds) that would be susceptible to infection by *Acinetobacter* spp., thus methods to remove them quickly and effectively would reduce or eliminate downstream complications. Outbreaks caused by MDR *Acinetobacter* have been reported in hospitals all over the world; more recently, they have become a serious problem in military medical facilities. Because of its MDR, *Acinetobacter* infections are difficult to treat so infections by these organisms usually result in a poor outcome. Thus, new and better ways of controlling this pathogen are needed.

*Acinetobacter baumannii* strains resistant to all known antibiotics have now been reported. Acting in synergy with this emerging resistance profile is the uncanny ability of *A. baumannii* to survive for prolonged periods throughout a hospital environment, thus potentiating its ability for nosocomial spread. The organism commonly targets hospitalized subjects, who are critically ill with breaches in skin integrity and airway protection. As such, hospital-acquired pneumonia is still the most common infection caused by *A. baumannii*. However, recently, infections involving the central nervous system, skin and soft tissue, and bone have emerged as highly problematic for certain institutions. Because of this resistance problem, new methods to control these pathogens must be developed.

Antimicrobial agents known as bacteriophage-encoded lysins have been identified. Bacteriophages are viruses that infect bacterial and it is estimated that there are $10^6$ distinct bacteriophage species. Bacteriophage lysins are generally genus- or species-specific, i.e., a *Staphylococcus aureus* phage lysin may have activity only against *Staphylococcus aureus* providing a targeted therapeutic approach. In some cases, lysins may have activity against several genera or species.

Bacteriophage infect their host bacteria to produce more virus particles. At the end of the reproductive cycle they are faced with a problem, how to release the progeny phage trapped within the bacterium. They solve this problem by producing an enzyme called "lysin" that degrades the cell wall of the infected bacteria to release the progeny phage. The lytic system consists of a holin and at least one peptidoglycan hydrolase, or lysin, capable of degrading the bacterial cell wall. Typically, the holin is expressed in the late stages of phage infection forming a pore in the cell membrane, allowing the lysin(s) to gain access to the cell wall peptidoglycan resulting in release of progeny phage. Significantly, exogenously added lysin, in the absence of a holin, can lyse the cell wall of healthy, uninfected cells, producing a phenomenon known as "lysis from without".

SUMMARY

We have recently identified, purified and characterized several phage lysins that specifically attack *Acinetobacter* bacteria. This is a breakthrough since most lysins have antibacterial activity only against gram-positive bacteria. The purified phage lysins of the present invention are well suited for a variety of applications such as treatment of bacterial infections, and disinfection.

BRIEF DESCRIPTION OF THE DRAWINGS

FIG. 4. Alignment of nucleotide sequences for cloned lysins.

FIG. 5. Alignment of amino acid sequences of cloned lysins.

FIG. 8. Scanning electron micrograph of 3-day biofilms of strain 1791 *A. baumannii* before and after treatment with F307 polypeptide.

FIG. 11. Sequence of F307, P307 polypeptide without and with short extension (P307Ex).

FIG. 12. FIG. 12A is a graph a comparison of in vitro bactericidal activities of P307, P307SQ-8C and P307$_{AE-8}$ against *A. baumannii* strains #1791, S5 and ATCC17978. FIG. 12B shows the comparative in vivo bactericidal activity of P307, P307SQ-8C, and P307CS-8 against *A. baumannii* strains #1791 and S5. FIG. 12C shows a comparison of the comparative in vivo bactericidal activity of P307SQ-8C and P307CS-8 against *A. baumannii* strains #1791, S5 and ATCC17978.

FIG. 13. The in vitro bactericidal activities of P307 and P307SQ-8C against *A. baumannii* strain #1791 to investigate the pH optimum (13A), and NaCl optimum (13B). The same conditions, except for the variables, were used with 50 mM Tris-HCl, pH 7.5 to determine the concentration optimum (13C), and killing kinetics (13D). The error bars show standard deviation and the black horizontal line marks the limit of detection.

FIG. 15.

FIG. 16. FIG. 16 shows the cytotoxic effects of P307 and P307SQ-8C as measured by B cell survival (16A) and hemolysis (16B).

FIG. 17 B shows the effect of substitution of the terminal cysteine residue of P307SQ-8C with alanine (P307SQ-8A).

FIG. 19. FIGS. 7 A-C show representative transmission electron microscopy images of *A. baumanii* strain no. 1791: untreated control (19A), treated with 300 µg/mL P307SQ-8C for 5 minutes (19B) and for 2 hours (19C). Magnification, ×2600 (left, scale bar=2 µm) and ×5000 (right top and bottom, scale bar=0.5 µm). FIG. 7D shows the bactericidal activity of P307SQ-8C on gram negative bacteria *K. pneumoniae* and *E. coli* at pH 7.5 and 8.8.

FIG. 21. Shows the inhibition of bactericidal activity of P307 or P307SQ-8C by hydroxyl radical scavenger, thiourea and anaerobic condition.

DETAILED DESCRIPTION

Figure 1A:
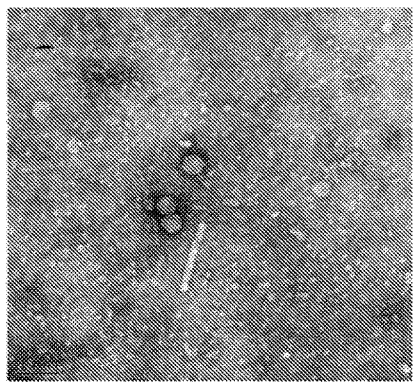
FIG. 1A. Negative staining electron micrograph showing phage induced from *A. baumannii* strain 1790.

The present invention provides polypeptides having antibacterial activity and for methods for using the disclosed polypeptides. As used herein, the singular forms "a", "an" and "the" include plural references unless the context clearly dictates otherwise.

Terms such as "comprises", "comprised", "comprising", "contains", "containing" and the like have the meaning attributed in United States patent law; they are inclusive or open-ended and do not exclude additional, un-recited elements or method steps. Terms such as "consisting essentially of" and "consists essentially of" have the meaning attributed in United States patent law; they allow for the inclusion of additional ingredients or steps that do not materially affect the basic and novel characteristics of the claimed invention. The terms "consists of" and "consisting of" have the meaning ascribed to them in United States patent law; namely that these terms are close ended In a first aspect, the invention provides polypeptides that comprise an amino acid sequence that has at least 90%, or at least 91%, or at least 92%, or at least 93%, or at least 94%, or at least 95%, or at least 96%, or at least 97%, or at least 98%, or at least 99%, or 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment has antibacterial activity.

In another embodiment of the first aspect, the polypeptides comprise an amino acid sequence that has at least 95%, or at least 96%, or at least 97%, or at least 98%, or at least 99%, or 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment has antibacterial activity.

In yet another embodiment of the first aspect, the polypeptides comprise an amino acid sequence that has 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment has antibacterial activity.

In a second aspect, the invention provides polypeptides that consist of an amino acid sequence that has at least 90%, or at least 91%, or at least 92%, or at least 93%, or at least 94%, or at least 95%, or at least 96%, or at least 97%, or at least 98%, or at least 99%, or 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment has antibacterial activity.

In another embodiment of the second aspect, the polypeptides consist of an amino acid sequence that has at least 95%, or at least 96%, or at least 97%, or at least 98%, or at least 99%, or 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment has antibacterial activity.

In yet another embodiment of the second aspect, the polypeptides consists of an amino acid sequence that has 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment has antibacterial activity.

In a third aspect, the invention provides polypeptides that comprise an amino acid sequence that has at least at least 80%, or at least 85%, or at least 90%, or at least 91%, or at least 92%, or at least 93%, or at least 94%, or at least 95%, or at least 96%, or at least 97%, or at least 98%, or at least 99%, or 100%, to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment is conjugated to an antimicrobial peptide to yield a conjugated polypeptide and the conjugated polypeptide has antibacterial activity.

In one embodiment of the third aspect the polypeptide comprises an amino acid sequence that has at least 90%, or at least 92%, or at least 94%, or at least 95%, or at least 96%, or at least 97%, or at least 98%, or at least 99%, or 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment is conjugated to an antimicrobial peptide to yield a conjugated polypeptide and the conjugated polypeptide has antibacterial activity.

In a fourth aspect, the invention provides polypeptides that consists of an amino acid sequence that has at least at least 80%, or at least 85%, or at least 90%, or at least 91%, or at least 92%, or at least 93%, or at least 94%, or at least 95%, or at least 96%, or at least 97%, or at least 98%, or at least 99%, or 100%, to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment is conjugated to an antimicrobial peptide to yield a conjugated polypeptide and the conjugated polypeptide has antibacterial activity.

In one embodiment of the fourth aspect the polypeptide consists of an amino acid sequence that has at least 90%, or at least 92%, or at least 94%, or at least 95%, or at least 96%, or at least 97%, or at least 98%, or at least 99%, or 100%, identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, or SEQ ID NO:21, or a fragment of the polypeptide, wherein the polypeptide or fragment is conjugated to an antimicrobial peptide to yield a conjugated polypeptide and the conjugated polypeptide has antibacterial activity.

In some embodiments of the third or fourth aspect, the antimicrobial peptide comprises the amino acid sequence SQSRESQC (SEQ ID NO:44) wherein at least one amino is cysteine and 0, 1, 2, 3, 4, 5, 6, or 7 amino acids of the antimicrobial peptide are conservatively substituted. 0, 1, 2, 3, 4, 5, 6, or 7 amino acids of the antimicrobial peptide are conservatively substituted. In other embodiments of the third or fourth aspects, the antimicrobial peptide comprises the amino acid sequence SQSRESQC (SEQ ID NO:44). In still other embodiments of the third or fourth aspect, the antimicrobial peptide comprises the amino acid sequence SQSRESQC (SEQ ID NO:44) wherein 0, 1, 2, 3, 4, 5, 6, or 7 amino acids of the antimicrobial peptide are conservatively substituted and the antimicrobial peptide consists of 8 amino acids. In yet other embodiments of the third or fourth aspect, the antimicrobial peptide consists of the amino acid sequence SQSRESQC (SEQ ID NO:44).

In some embodiments of the third or fourth aspect, the antimicrobial peptide comprises the amino acid sequence CSQRQSES (SEQ ID NO:50) wherein at least one amino is cysteine and 0, 1, 2, 3, 4, 5, 6, or 7 amino acids of the antimicrobial peptide are conservatively substituted. In other embodiments of the third or fourth aspects, the antimicrobial peptide comprises the amino acid sequence CSQRQSES (SEQ ID NO:50). In still other embodiments of the third or fourth aspect, the antimicrobial peptide comprises the amino acid sequence CSQRQSES (SEQ ID NO:50) wherein 0, 1, 2, 3, 4, 5, 6, or 7, amino acids of the antimicrobial peptide are conservatively substituted and the antimicrobial peptide consists of 8 amino acids. In yet other embodiments of the third or fourth aspect, the antimicrobial peptide consists of the amino acid sequence CSQRQSES (SEQ ID NO:50).

In some embodiments of the third or fourth aspect, the C-terminus of the polypeptide or the fragment is conjugated to the antimicrobial peptide. In other embodiments of the third or fourth aspect, the C-terminus of the polypeptide or the fragment is conjugated to the N-terminus of the antimicrobial peptide. In still other embodiments of the third or fourth aspect, the N-terminus of the polypeptide or fragment is conjugated to the antimicrobial peptide. In yet other embodiments of the third or fourth aspect, the N-terminus of the polypeptide or fragment is conjugated to the C-terminus of the antimicrobial peptide. For any of the embodiments of the third or fourth aspect the antimicrobial peptide can be conjugated to the polypeptide or fragment via a peptide bond.

Another embodiment of the peptides of the present disclosure is a peptide having the amino acid sequence NAKDYKGAAAEFPKWNKAGGRVLAGLVKRRKSQSRESQA (SEQ ID NO: 53). Another embodiment is a peptide having the amino acid sequence NAKDYKGAAAEFPKWNKAGGRVLAGLVKRRKCSQRQSES (SEQ ID NO:51).

In some embodiments the polypeptides, polypeptide fragments or conjugated polypeptides have antibacterial activity against a gram-negative bacterium. In some embodiments, the gram-negative bacterium is of the genus *Acinetobacter*.

In some embodiments the polypeptides, polypeptide fragments or conjugated polypeptides have antibacterial activity against *E. coli, P. aeruginosa* or *A. baumannii*.

In some embodiments the polypeptides, polypeptide fragments or conjugated polypeptides have antibacterial activity against a gram-positive bacterium. In some embodiments, the gram-positive bacterium is *S. aureus* or *B. anthracis*.

In some embodiments, the polypeptide is lyophilized.

Specific embodiments of the polypeptides of the invention are provided in Table 1.

TABLE 1

| SEQ ID NO: 1 | F307 |
| SEQ ID NO: 2 | F376 |
| SEQ ID NO: 3 | F351 |
| SEQ ID NO: 4 | F347 |
| SEQ ID NO: 5 | F344 |
| SEQ ID NO: 6 | F340 |
| SEQ ID NO: 7 | F338 |
| SEQ ID NO: 8 | F336 |
| SEQ ID NO: 9 | F334 |
| SEQ ID NO: 10 | F332 |
| SEQ ID NO: 11 | F330 |
| SEQ ID NO: 12 | F328 |
| SEQ ID NO: 13 | F324 |
| SEQ ID NO: 14 | F321 |
| SEQ ID NO: 15 | F320 |
| SEQ ID NO: 16 | F315 |
| SEQ ID NO: 17 | F306 |
| SEQ ID NO: 18 | F303 |
| SEQ ID NO: 19 | F301 |
| SEQ ID NO: 20 | F309 |
| SEQ ID NO: 21 | F311 |
| SEQ ID NO: 43 | P307 |
| SEQ ID NO: 44 | SQSRESQC |
| SEQ ID NO: 45 | P307SQ-8C (P307Ex) |
| SEQ ID NO: 48 | AEMLFLK |
| SEQ ID NO: 49 | P307AE-8 |
| SEQ ID NO: 50 | CSQRQSES |
| SEQ ID NO: 51 | P307CS-8 |
| SEQ ID NO: 52 | SQSRESQA |
| SEQ ID NO: 53 | P307SQ-8A |

P307SQ-8C and P307Ex are used interchangeably herein.

The invention also provides for pharmaceutical compositions comprising the polypeptides, polypeptide fragments or conjugated polypeptides of the invention. In some embodiments, the compositions are pharmaceutical compositions, which comprise a pharmaceutically acceptable carrier, buffering agent, or preservative.

In some embodiments, the pharmaceutical composition is formulated for topical administration. In other embodiments, the pharmaceutical composition is formulated for subcutaneous delivery. In still other embodiments, the pharmaceutical composition is formulated for intravenous delivery. In yet other embodiments, the pharmaceutical composition is formulated for oral delivery.

In some embodiments, the composition further comprises an antibiotic. Examples of suitable antibiotics include, but are not limited to, amoxicillin, augmentin, amoxicillin, ampicillin, azlocillin, flucloxacillin, mezlocillin, methicillin, penicillin G, penicillin V, cephalexin, cefazedone, cefuroxime, loracarbef, cemetazole, cefotetan, cefoxitin, ciprofloxacin, levaquin, and floxacin, tetracycline, doxycycline, or minocycline, gentamycin, amikacin, and tobramycin, clarithromycin, azithromycin, erythromycin, daptomycin, neomycin, kanamycin, or streptomycin.

In some embodiments, the pharmaceutical composition further comprises a clotting agent.

In some embodiments, the pharmaceutical composition is lyophilized.

The present invention also provides for methods for treating a subject in need thereof, comprising administering to the subject a pharmaceutical composition comprising a polypeptide, polypeptide fragment or conjugated polypeptide of the invention, and a pharmaceutically acceptable carrier, buffering agent, or preservative.

In one embodiment the method is a method for treating a subject in need thereof, comprising administering to the subject a pharmaceutical composition comprising a polypeptide of the invention, and a pharmaceutically acceptable carrier, buffering agent, or preservative.

In another embodiment the method is a method for treating a subject in need thereof, comprising administering to the subject a pharmaceutical composition comprising a polypeptide fragment of the invention, and a pharmaceutically acceptable carrier, buffering agent, or preservative.

In one embodiment the method is a method for treating a subject in need thereof, comprising administering to the subject a pharmaceutical composition comprising a conjugated polypeptide of the invention, and a pharmaceutically acceptable carrier, buffering agent, or preservative.

In one embodiment the method is a method for treating having a bacterial infection and the treatment is therapeutic treatment comprising administering to the subject a pharmaceutical composition comprising a conjugated polypeptide of the invention, and a pharmaceutically acceptable carrier, buffering agent, or preservative. In some embodiments, the subject has a bacterial infection that is non-responsive to other treatment modalities. For example, the bacterial infection may be resistant to one or more antibiotic. In one embodiment, the bacterial infection is a wound infection.

In one embodiment the method is a method for prophylactically treating a subject in need thereof comprising administering to the subject a pharmaceutical composition comprising a conjugated polypeptide of the invention, and a pharmaceutically acceptable carrier, buffering agent, or preservative. In some embodiments the subject has undergone, or is undergoing surgery and the surgical wound is contacted with a pharmaceutical composition of the invention. In certain embodiments, the surgical wound is irrigated with the pharmaceutical composition prior to closure of the wound. In other embodiments the pharmaceutical composition is applied to the wound after closure, for example the pharmaceutical composition is applied to the sutured or stapled area of the wound.

In some embodiments, the method comprises administering a pharmaceutical composition of the invention is administered in combination with an antibiotic. In some embodiments, the method comprises topically administering a pharmaceutical composition of the invention. In other embodiments, the method comprises administering a pharmaceutical composition of the invention subcutaneously. In still other embodiments, the method comprises administering a pharmaceutical composition of the invention by intravenous injection. In yet other embodiments, the method comprises administering a pharmaceutical composition of the invention orally.

In some embodiments, the pharmaceutical composition is in a unit dosage form. In other embodiments, the pharmaceutical composition is in the form of a cream, ointment, salve, gel, lozenge, spray, or aerosol.

Also provided, are methods for treating a bacterial infection comprising inhibiting the formation of or disrupting a bacterial biofilm comprising administering to a subject in need thereof, a composition comprising a polypeptide, polypeptide fragment or conjugated polypeptide of the invention in an amount effective to kill bacteria in the biofilm.

Additionally provided, are methods of disinfecting an article comprising contacting the article with a composition comprising a polypeptide, polypeptide fragment or conjugated polypeptide of the invention to the article for a time sufficient to disinfect the article. In some embodiments, the article is a hard surface. In some embodiments, the article is a countertop, keyboard, surgical instrument, or medical device.

Additionally provided, are methods for inhibiting the formation of or disrupting a bacterial biofilm on an article comprising contacting the article with a polypeptide, polypeptide fragment or conjugated polypeptide of the invention, in an amount effective to kill bacteria in the biofilm.

Also provided, are articles of manufacture that contain a composition comprising a polypeptide, polypeptide fragment or conjugated polypeptide of the invention. In some embodiments, the article of manufacture is a spray bottle that contains a polypeptide, polypeptide fragment or conjugated polypeptide of the invention.

In some embodiments, the article of manufacture contains a pharmaceutical composition comprising a polypeptide, polypeptide fragment or conjugated polypeptide of the invention and a carrier, buffering agent or preservative. In some embodiments, the article of manufacture is a vial. In some embodiments, the article of manufacture is a delivery device. In some embodiments, the composition contained by the article of manufacture is lyophilized.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

Such amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Be: Leu, Val), (Leu: Be, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity" as known in the art, is a relationship between two or more polypeptide sequences, as determined by comparing the sequences. "Identity" can be readily calculated by known algorithms well known in the art. Preferred methods to determine identity are designed to give the largest match between the sequences tested. Methods to determine identity are codified in publicly available computer programs. The percent identity between two sequences can be determined using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST).

Identity can be measured as "local identity" or "global identity". Local identity refers the degree of sequence relatedness between polypeptides as determined by the match between strings of such sequences. Global identity refers to the degree of sequence relatedness of a polypeptide compared to the full-length of a reference polypeptide. Unless specified otherwise, as used herein identity means global identity. The percentages for global identity herein are calculated using the ClustalW algorithm used through the software MacVector, using the default settings; both for local and global identity.

Production of Polypeptides

Polypeptides of the present invention can be produced by any known method. For example, polypeptides can be produced in bacteria including, without limitation, *E. coli*, or in other existing system for polypeptide (e.g., *Bacillus subtilis*, baculovirus expression systems using *Drosophila* Sf9 cells, yeast or filamentous fungal expression systems, mammalian cell expression systems), or they can be chemically synthesized.

If the a polypeptide is to be produced in bacteria, e.g., *E. coli*, the nucleic acid molecule encoding the peptide may also encode a leader sequence that permits the secretion of the mature peptide from the cell. Thus, the sequence encoding the peptide can include the pre sequence and the pro sequence of, for example, a naturally occurring bacterial ST peptide. The secreted, mature peptide can be purified from the culture medium.

The sequence encoding a peptide described herein is can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector may be a bacterial or bacteriophage DNA vector such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B subtilis, Pseudomonas, Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences. A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during peptide production.

One embodiment of a nucleic acid according to the present invention is a nucleic acid that encodes a polypeptide comprising an amino acid sequence that has at least 90% sequence identity to the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:45, or a fragment of the polypeptide, wherein the polypeptide or fragment has antibacterial activity.

In another embodiment, the nucleic acid encodes a polypeptide comprising an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:45, or a fragment of the polypeptide, wherein the polypeptide or fragment has antibacterial activity.

In yet another embodiment, the nucleic acid encodes a polypeptide consisting of an amino acid sequence nucleic acid of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:45, or a fragment of the polypeptide, wherein the polypeptide or fragment has antibacterial activity.

In still another embodiment, the nucleic acid comprises the nucleotide sequence of SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

In still another embodiment, the nucleic acid consists of the nucleotide sequence of SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

Another embodiment is an expression vector that comprises a nucleic acid that encodes a polypeptide comprising an amino acid sequence that has at least 90% sequence identity to the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:45, or a fragment of the polypeptide, wherein the polypeptide or fragment has antibacterial activity.

In another embodiment, the expression vector comprises a nucleic acid that encodes a polypeptide comprising an amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:45, or a fragment of the polypeptide, wherein the polypeptide or fragment has antibacterial activity.

In yet another embodiment, the expression vector comprises a nucleic acid that encodes a polypeptide consisting of an amino acid sequence nucleic acid of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, or SEQ ID NO:45, or a fragment of the polypeptide, wherein the polypeptide or fragment has antibacterial activity.

In still another embodiment, the expression vector comprises a nucleic acid that comprises the nucleotide sequence of SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

In still another embodiment, the expression vector comprises a nucleic acid that consists of the nucleotide sequence of SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42.

Table 2 provides specific embodiments of the nucleic acids of the invention showing the nucleotide SEQ ID NO: that corresponds to the polypeptides they encode.

TABLE 2

| Nucleotide SEQ ID NO: | Corresponding Amino Acid SEQ ID NO: |
| --- | --- |
| 22 | 1 |
| 23 | 2 |
| 24 | 3 |
| 25 | 4 |
| 26 | 5 |
| 27 | 6 |
| 28 | 7 |
| 29 | 8 |
| 30 | 9 |
| 31 | 10 |
| 32 | 11 |
| 33 | 12 |
| 34 | 13 |
| 35 | 14 |
| 36 | 15 |
| 37 | 16 |
| 38 | 17 |
| 39 | 18 |
| 40 | 19 |
| 41 | 20 |
| 42 | 21 |

The nucleic acid that encodes a polypeptide described herein can also be fused to a nucleic acid encoding a peptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the peptide of interest to the reading frame of the gene encoding the affinity tag such that a translational fusion is generated. Expression of the fusion gene results in translation of a single peptide that includes both the peptide of interest and the affinity tag. In some instances where affinity tags are utilized, DNA sequence encoding a protease recognition site will be fused between the reading frames for the affinity tag and the peptide of interest.

Genetic constructs and methods suitable for production of immature and mature forms of the polypeptides and variants described herein in protein expression systems other than bacteria, and well known to those skilled in the art, can also be used to produce polypeptides in a biological system.

Polypeptides and variants thereof can be synthesized by the solid-phase method using an automated peptide synthesizer. For example, the peptide can be synthesized on Cyc(4-$CH_2$ Bxl)-$OCH_2$-4-(oxymethyl)-phenylacetamidomethyl resin using a double coupling program. Peptides can also be synthesized by many other methods including solid phase synthesis using traditional FMOC protection (i.e., coupling with DCC-HOBt and deprotection with piperdine in DMF).

Therapeutic and Prophylactic Compositions and their Use

This invention provides methods of treatment comprising administering to a subject in need thereof an effective amount of a polypeptide of the invention. The subject is human or another animal, including but not limited to primates such as monkeys and chimpanzees; livestock animals such as cows, pigs, horse or chickens; and companion animals such as dogs cats, and rodents. In a specific embodiment the subject is a human. In another specific embodiment the subject is a non-human mammal. In one embodiment the polypeptides are administered as the sole antibacterial agent. In another embodiment the polypeptides are administered in combination with one or more other antibacterial agents.

Methods of administration of the disclosed pharmaceutical compositions can be oral or parenteral and include but are not limited to intradermal, intramuscular, intraperitoneal, intravenous, intra-articular, intra-synovial, subcutaneous, intranasal, epidural, topical and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. In a specific embodiment, it may be desirable to administer the pharmaceutical compositions of the invention locally to the area in need of treatment, such as topical use on the skin; any suitable method known to the art may be used.

In one aspect of the invention provides for pharmaceutical compositions comprising the polypeptides of the present disclosure for therapeutic or prophylactic treatment of bacterial infections. An embodiment of the invention is a pharmaceutical composition formulated for topical treatment. Another embodiment of the invention is a pharmaceutical composition formulated for systemic infections.

Such compositions comprise a therapeutically effective amount of a polypeptide of the invention and a pharmaceutically acceptable carrier, buffering agent, or preservative. The term "pharmaceutically acceptable carrier" as used herein, includes, but is not limited to, solvents, diluents, or other liquid vehicle, dispersion or suspension aids, surface active agents, isotonic agents, thickening or emulsifying agents, solid binders, lubricants and the like, as suited to the particular dosage form desired. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition can also contain of wetting or emulsifying agents, preservatives, or pH buffering agents. These compositions can take the form of a solution, suspension, emulsion, tablet, pill, lozenge, capsule, powder, patches for topical administration and the like. For topical applications, the pharmaceutically acceptable compositions may be formulated in a suitable ointment, lotion or cream containing the active component suspended or dissolved in one or more carriers. Carriers for topical administration include, but are not limited to, mineral oil, liquid petrolatum, white petrolatum, propylene glycol, polyoxyethylene-polyoxypropylene compounds, emulsifying wax, polysorbate 60, cetyl esters wax, ceteary alcohol, 2-octyldodecanol, benzyl alcohol and water. The composition can be formulated as a suppository with traditional binders and carriers such as triglycerides. Oral formulation can include standard carriers such as pharmaceutical grades of mannitol, lactose, starch, magnesium stearate, sodium saccharine, cellulose, magnesium carbonate, etc. One of skill in the art is well versed in formulation of therapeutic agents. See e.g. Remington The Science and Practice of Pharmacy, 20th Edition, Lippincott Williams & White, Baltimore, Md. (2000); *Remington's Pharmaceutical Sciences,* 19th Edition (Mack Publishing Company, 1995).

The invention also provide a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use, or sale of pharmaceuticals or biologic products, which notice reflects (a) approval by the agency of manufacture, use or sale for human administration, (b) directions for use, or both.

EXAMPLES

The following examples are put forth so as to provide additional information to one of skill in the art of how to make and use the polypeptides described herein, and are not intended to limit the scope of what the inventors regard as their invention. Efforts have been made to ensure accuracy with respect to numbers used (e.g., amounts, temperature, etc.) however, some experimental errors and deviations should be accounted for. Unless indicated otherwise, molecular weight is average molecular weight, and the temperature is in degrees Centigrade.

Example 1

Identification of Polypeptides Having Antibacterial Activity.

Figure 1B:
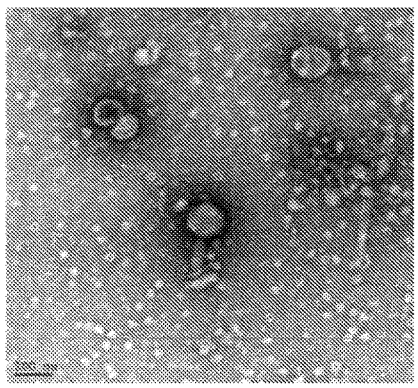
FIG. 1B. Negative staining electron micrograph showing phage induced from *A. baumannii* strain 1794
Figure 1C:
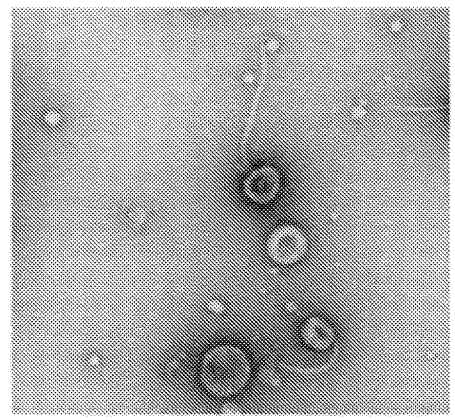
FIG. 1C. Negative staining electron micrograph showing phage induced from *A. baumannii* strain 1796

Fifteen clinical isolates of *A. baumannii* were obtained from a New York hospital. Strains of *A. baumannii* were isolated and treated with mitomycin C to induce prophage induction. The supernatants were collected and phage were precipitated with polyethylene glycol (PEG). Supernatants from three of the *A. baumannii* isolates were examined by negative staining EM and images taken of the phage (FIGS. 1A, 1B, and 1C).

Phage DNA was separated from co-precipitated compounds by agarose gel electrophoresis and extraction of high-molecular-weight DNA. From this DNA, an expressible linker shotgun library (E-LASL) was constructed as previously described. (Schmitz J E. et al., 2008, Appl. Environ. Microbiol. 74:1649-1652.) Briefly, for all samples, 100 ng of DNA was fragmented with the restriction enzyme TSP509I (consensus sequence AATT) Following phenol-chloroform extraction and ethanol precipitation, the DNA was ligated to 40 ng of linker sequence, with a complementary 5' overhang (AATTCGGCTCGAG, where the overhang is underlined (SEQ ID NO:46). The ligation mixture was used as the template for Taq-based PCR using the linker-targeted primer CCATGACTCGAGCCGAATT (SEQ ID NO:47).

The amplified inserts were ligated into the arabinose-inducible pBAD plasmid using the pBAD TOPO® TA expression kit; Invitrogen, per the manufacturer's directions. The recombinant vectors were transformed into competent *E. Coli* TOP10 (Invitrogen). To determine which clones had lytic activity, the *E. coli* were plated on LB agar supplemented with 100 μg/ml ampicillin and 5% defibrinated sheep's blood. Following overnight growth at 37° C., the plates were placed in a sealed container that was attached to the outlet of a commercial nebulizer. Nebulized arabinose was continuously pumped into the container for 1 hour. The plates were returned to 37° C. and colonies were identified that developed a zone of hemolysis in the surrounding blood agar. Chosen clones were streaked onto separate LB-ampicillin plates (lacking arabinose) and allowed to propagate without induced expression. (Schmitz J E, et al., 2010 Appl. Environ. Microbiol. 76:7181-7187).

To determine killing activity for *A. baumannii*, a secondary screen was done essentially as described in Schmitz J E, et al., 2010 Appl. Environ. Microbiol. 76:7181-7187. Hits were streaked as approximately 1-cm by 2-cm patches onto LB-ampicillin plates supplemented with 0.2% arabinose. Following overnight incubation at 37° C., the plates were exposed to chloroform vapor to kill and permeabilize any still-viable *E. coli*. The patches were then overlaid with molten soft agar containing *A. baumannii* and observed for clearing zones. Twenty-one positive clones were identified that exhibited a clear zone around the clone. FIG. 2 shows a representative screen of lysin clone activity in clearing live *A. baumannii* imbedded in the agar.

The inserts of the positive closes were sequenced and compared to the sequences in the NCBI protein database. The alignments showed that among the 21 clones there are four classes of lytic activity: i) nine were in the glycosyl hydrolase family, ii) seven were phage baseplate lysozymes, iii) two were lysozyme autolysins, and iv) three were lysins. (FIG. 3). For ease of reference here in, regardless of class, the polypeptides encoded by these sequences are referred to as "lysins". FIG. 4 shows a sequence alignment based on similarity of the nucleotide sequences encoding the 21 clones. FIG. 5 shows a sequence alignment based on similarity of the polypeptide sequences of the 21 clones.

Example 2

Activity of Positive Clones.

Twenty-one different constructs were screened for activity against thirteen different *A. baumannii* clinical isolates. The constructs were recombinantly expressed in *E. coli*. Cells were grown at 30° C. 200 rpm, and when reaching mid-log phase they were induced by adding 0.2% arabinose. Induction continued overnight. In the morning, cells were spun down, washed 3× with 50 mM sodium phosphate buffer pH 7.0, before being homogenized in an Emulsiflex homogenizer. Cell debris was removed by centrifugation (16000 g, 45 min) and the lysate passed through a 0.22 um sterile filter to generate the crude lysate.

*A. baumannii* grown overnight in TSB, were mixed with 50° C. soft agar TSB and poured onto a TSB agar plate as a top agar layer. The plate was allowed to solidify in room temperature. Crude lysates (10 ul) were added to a soft agar plate with *A. baumannii*, and incubated for 2 hours at room temperature each day, while being kept at 4° C. for the remainder of the time. Plates were incubated until clearing zones were visible (4-5 days). A clearing zone larger than the original spot of the crude lysate was scored. The number above each lysin indicates how many stains for which that lysin was the most efficient.

Results are shown in FIG. 6. The lysin construct is shown on the x-axis and the percent of *Acinetobacter* strains lysed is shown on the y-axis. The numbers above each bar indicates the number of strains for which that lysin was the most efficient, no number indicates one strain. As can be seen, Lysin F307 lysed about 90% of the strains tested and was the most active against seven strains.

Example 3

Lysis of *A. baumannii* by F307.

FIG. 7 shows representative Transmission Electron Micrographs of *A. baumannii* strain 1791 cells after treatment with F307 polypeptide. The micrographs show that F307 caused lysis through extrusion of the cytoplasmic membrane to the outside of the cell. (See FIG. 7, arrows). Two 100 mL culture of *A. baumannii* strain 1791 were started in BHI media and grown in a 500 mL flask for 1.5 h at 37° C., 200 rpm. The cells were then centrifuged and washed one time with 1×PBS buffer. They were then resuspended in 1.2 mL of 1×PBS. EDTA at a final concentration of 250 μM was added to each sample. To the experimental sample 300 μL of lysin (~1.2 mg final concentration) and incubated the control (EDTA alone) and experimental (EDTA+F307 lysin) at 25° C. Time points were taken at 0.5, 1, 5, 10, 15, and 30 minutes. The reactions were quenched and cells were fixed using 2.5% Gluteraldhyde in CAC buffer (10 mm sodium cacodylate, 0.1 m CaCl2, pH 6.5).

Example 4

Effect of F307 Polypeptide on *A. baumannii* Biofilms on Catheters In Vitro and In Vivo.

In Vitro Treatment of Catheter Adherent *A. baumannii* 1791 with F307 Lysin

Catheter tubing (CareFusion Ref#72023E) was cut using a sterile scalpel into 3-inch long sections. An overnight culture of *A. baumannii* 1791 was used to inoculate 1:1000 a 50 mL of TSB 0.2% Glucose (~1×105 CFU/mL). Each 3-inch catheter tube was seeded with 300-350 of the 1:1000 diluted culture. The catheters were then clamped and placed in plastic containers in a 37° C. incubator for 3 days to allow for biofilm formation to occur. After the 3 days catheters were washed twice with either PBS or Sodium Phosphate buffer pH 7.5 and then had 300-350 μL of F307 added to the tube (~1 mg final concentration). The catheters were then clamped. Catheters were taken at time points 0, 15 minutes, 30 minutes, and 1 hour. The catheters were washed twice with 50 mM Sodium Phosphate pH 7.5 and were cut into small pieces. These were placed into a 1.5 mL ependorff tube and 500 μL of 50 mM NaP buffer pH 7.5 was added. The tubes were sonicated for 20 minutes, and vortexed for 1 minute. The samples were then serial diluted and 20 μL was plated onto a quadrant of a BHI agar plate and incubated at 37° C. overnight. CFU's were calculated the following morning.

An approximate 4-log drop in the number of colony forming units (CFU's of *A. baumannii* was observed after 30 minutes of treatment. Table 3 shows CFU counts. FIG. 8 shows Scanning Electron micrographs of 3-day biofilms of *A. baumannii* strain 1791 before and after treatment with 250 μg F307 polypeptide.

TABLE 3

Treatment of *A. baumannii* biofilms on catheters.

| Sample | CFU |
|---|---|
| no treatment | $1.4 \times 10^7$ |
| no treatment replicate | $3.0 \times 10^6$ |
| 15 minutes F307 treatment | $9.0 \times 10^4$ |
| 30 minutes F307 treatment | $6.0 \times 10^3$ |

Example 5

Figure 9:
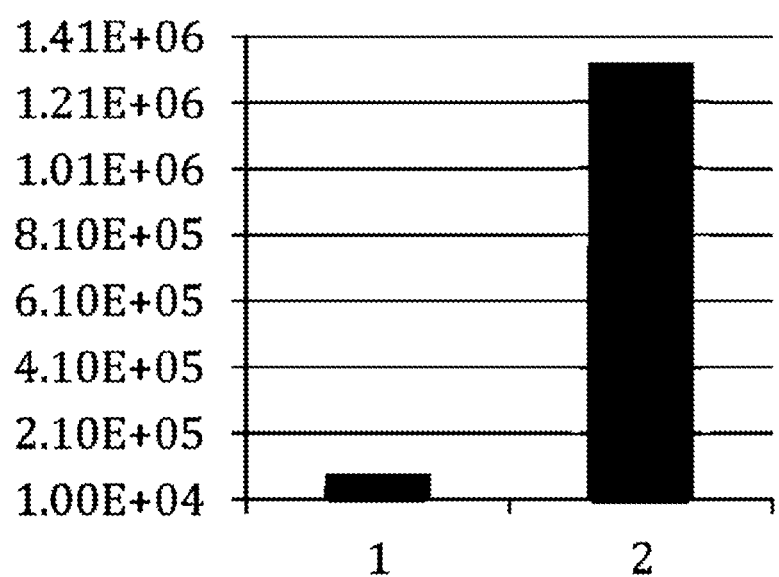
FIG. 9. Is a graph showing reduction in bacterial counts on whole catheter pieces with *Acinetobacter* biofilm after treatment with F307 polypeptide.

Mouse Catheter Model: Several 3 inch section of catheter tubing were seeded (1:1000) with *A. baumannii* strain 1791. *A. baumannii* biofilms were formed as described above. The back of twenty BALB/C mice were shaved, their backs were sterilized, and then an incision was made to place a 1 inch section of the catheter with a biofilm already formed under the dermis of the back. The incisions were then stapled shut. After 24 hours, 250 µl of F307 (1 mg) (n=10) or 250 µl control vehicle (n=10) was injected directly into the catheter that was under the dermis of the mouse. The treatment was repeated after 4 hours. After 3 hours the catheters were removed from the mice, and assayed as described in Experiment 4. FIG. 9 shows the reduction of bacterial counts by approximately 2-logs in mice treatment with F307 polypeptide compared with control.

Example 6

F307 Polypeptide Rescues Mice from Death after a Lethal Injection of *A. baumannii*.

Figure 10:
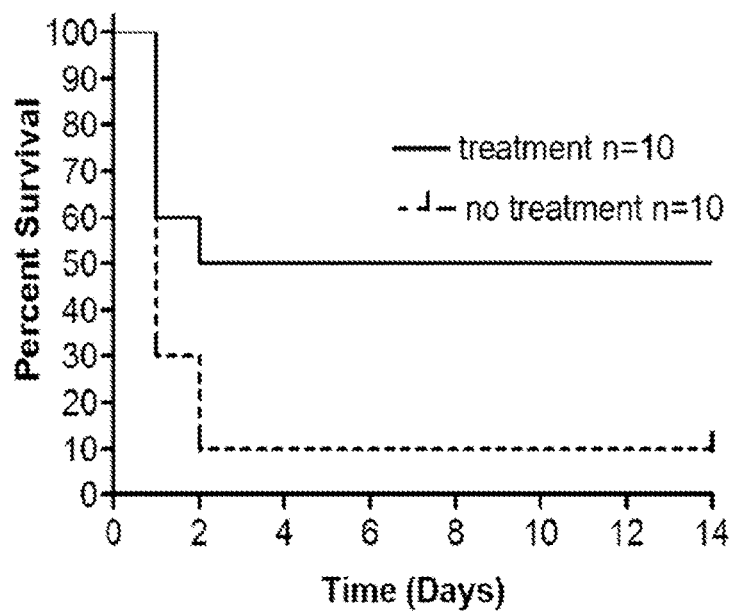
FIG. 10. Is a graph showing the survival of mice infected with *A. baumannii* treated with F307 polypeptide versus control.

Twenty-two C57BL/6 mice were given $10^8$ CFU of *A. baumannii* strain intraperitoneally (IP). Two hours later, two mice were euthanized and organs examine as described below, ten mice injected IP with 1 mg of F307 and ten mice were injected IP with control vehicle. Treated animals showed 50% survival with this dose of lysin, whereas control mice showed only 10% survival 14 days after infection (FIG. 10).

The organs from the two mice that were euthanized after infection were examined to confirm that the organs were infected with *A. baumannii* at the time of treatment with F307 polypeptide. Liver, spleen, kidney, and heart were dissected from the mice. The organs were then homogenized in 500 µl of 1×PBS. Dilutions were made and were plated onto Brain Heart infusion (BHI) plates. The plates were incubated at 37° C. overnight. The number of colony forming units was counted. Control mice were sacrificed at the two hour time point and showed *Acinetobacter* in all organs examined indicating that the organs were infected with *A. baumannii* at the time of treatment.

Example 7

P307 polypeptide (SEQ ID NO:43) was tested in duplicate against 18 clinical isolates of *A. baumannii* strains. *A. baumannii* strains were cultured ON to reach stationary phase. Cells were washed 3× in 20 mM Tris pH 7.5 and resuspended in the same buffer to an OD (595 nm) of around 0.7. To these cells, P307 (250 ug/ml) or a corresponding volume of buffer, was added, and the mixture was allowed to incubate for 60 minutes at room temperature. Dilutions of the mixtures were made and plated on TSB Agar plates for subsequent counting of colony forming units.

P307 polypeptide treatment resulted in a 1 to 8-log drop in bacterial viability, versus control, after incubation for 60 minutes with 250 µg of P307. Results are show in Table 4. When P307 was compared with the full length F307 polypeptide (SEQ ID NO:1) the P307 polypeptide had higher activity.

TABLE 4

P307 activity against 18 *A. baumannii* strains.

| Strain | Control 1 | Control 2 | Control Average | P307 1 | P307 2 | P307 Average | Difference | Log drop |
|---|---|---|---|---|---|---|---|---|
| 1775 | 1.00E+08 | 4.50E+08 | 2.75E+08 | 1.00E+07 | 1.50E+07 | 1.25E+07 | 2.20E+01 | 1.34 |
| 1776 | 5.50E+08 | 3.50E+08 | 4.50E+08 | 8.80E+05 | 7.50E+05 | 8.15E+05 | 5.52E+02 | 2.74 |
| 1777 | 7.00E+08 | 4.00E+08 | 5.50E+08 | 6.50E+06 | 9.00E+06 | 7.75E+06 | 7.10E+01 | 1.85 |
| 1788 | 2.00E+08 | 3.00E+08 | 2.50E+08 | 1.50E+07 | 1.20E+07 | 1.35E+07 | 1.85E+01 | 1.27 |
| 1789 | 4.50E+08 | 3.50E+08 | 4.00E+08 | 1.10E+07 | 1.30E+07 | 1.20E+07 | 3.33E+01 | 1.52 |
| 1790 | 1.50E+08 | 2.00E+08 | 1.75E+08 | 5.50E+05 | 1.80E+05 | 3.65E+05 | 4.79E+02 | 2.68 |
| 1791 | 9.0E+08 | 4.5E+08 | 6.8E+08 | 2.2E+05 | 2.2E+05 | 2.2E+05 | 3.1E+03 | 3.49 |
| 1792 | 1.2E+09 | 8.5E+08 | 1.0E+09 | 7.1E+05 | 7.5E+05 | 7.3E+05 | 1.4E+03 | 3.15 |
| 1793 | 3.5E+08 | 5.0E+08 | 4.3E+08 | 6.5E+05 | 5.6E+05 | 6.1E+05 | 7.0E+02 | 2.85 |
| 1794 | 7.5E+08 | 4.0E+08 | 5.8E+08 | 7.0E+05 | 6.0E+05 | 6.5E+05 | 8.8E+02 | 2.95 |
| 1795 | 9.5E+08 | 1.3E+09 | 1.1E+09 | 9.0E+06 | 2.5E+07 | 1.7E+07 | 6.6E+01 | 1.82 |
| 1796 | 1.0E+09 | 7.0E+08 | 8.5E+08 | 8.2E+05 | 8.2E+05 | 8.2E+05 | 1.0E+03 | 3.02 |
| 1797 | 1.2E+09 | 9.0E+08 | 1.1E+09 | 6.7E+05 | 6.5E+05 | 6.6E+05 | 1.6E+03 | 3.20 |
| 1798 | 4.0E+08 | 4.0E+08 | 4.0E+08 | 2.7E+05 | 6.5E+05 | 4.6E+05 | 8.7E+02 | 2.94 |
| 1799 | 5.5E+08 | 3.5E+08 | 4.5E+08 | 2.9E+07 | 7.0E+06 | 1.8E+07 | 2.5E+01 | 1.40 |
| S1 | 1.4E+09 | 1.1E+09 | 1.3E+09 | 4.2E+07 | 3.0E+07 | 3.6E+07 | 3.5E+01 | 1.54 |
| S3 | 2.5E+08 | 2.0E+08 | 2.3E+08 | 6.8E+05 | 6.5E+05 | 6.7E+05 | 3.4E+02 | 2.53 |
| S5 | 1.1E+09 | 8.5E+08 | 9.8E+08 | 1.0E+00 | 1.0E+00 | 1.0E+00 | 9.8E+08 | 8.99 |

Example 8

Addition of a Short Extension Peptide Resulted in Increased Antibacterial Activity of P307.

The peptide SQSRESQC (SEQ ID NO:44) is derived from hepatitis C virus and has been shown to have antimicrobial activity against gram-positive and gram-negative bacteria. We conjugated this sequence to P307 (P307Ex) to determine its effect on the activity. The sequence of F307, p307 and the P307Ex (SEQ ID Nos: 1, 43 and 45 respectively) are provided in FIG. 11 where a portion of the sequence of F307 is underlined to show the location of P307 and a portion of the sequence of P307 is double underline to show the location of the antimicrobial sequence.

P307 and P307Ex were assayed in duplicate against six bacterial strains. Antibacterial acidity was measured as described in Example 5. Treatment with P307Ex resulted in a 3.2 log drop in *A. baumannii* 1791 whereas treatment with P307 resulted in a 2.9 log drop demonstrating that the addition of the antimicrobial peptide increased the activity of P307. The results are shown in Table 5.

TABLE 5

| Strain | Control 1 | P307 EX1 | P307 EX 2 | P307Ex Average | Difference | Log drop |
|---|---|---|---|---|---|---|
| 1775 | 5.00E+08 | 1.60E+05 | 1.10E+05 | 1.35E+05 | 3.70E+03 | 3.5 |
| 1776 | 5.00E+08 | 5.50E+05 | 6.50E+05 | 6.00E+05 | 8.33E+02 | 2.9 |
| 1777 | 6.50E+08 | 6.50E+04 | 2.80E+05 | 1.73E+05 | 3.77E+03 | 3.5 |
| 1788 | 3.50E+08 | 8.80E+05 | 5.80E+05 | 7.30E+05 | 4.79E+02 | 2.6 |
| 1789 | 4.00E+08 | 1.10E+07 | 1.30E+07 | 1.20E+07 | 3.33E+01 | 1.5 |
| 1790 | 2.00E+08 | 1.50E+04 | 2.00E+04 | 1.75E+04 | 1.14E+04 | 4.0 |
| 1791 | 3.50E+08 | 4.00E+04 | 4.50E+04 | 4.25E+04 | 8.24E+03 | 3.9 |
| 1792 | 1.00E+08 | 4.00E+04 | 5.00E+03 | 2.25E+04 | 4.44E+03 | 3.6 |
| 1793 | 1.50E+08 | 3.50E+04 | 2.00E+04 | 2.75E+04 | 5.45E+03 | 3.7 |
| 1794 | 5.00E+07 | 1.40E+05 | 1.00E+05 | 1.20E+05 | 4.17E+02 | 2.6 |
| 1795 | 4.00E+08 | 5.50E+04 | 1.30E+05 | 9.25E+04 | 4.32E+03 | 3.6 |
| 1796 | 2.50E+08 | 3.80E+05 | 2.50E+05 | 3.15E+05 | 7.94E+02 | 2.8 |
| 1797 | 2.50E+08 | 5.50E+06 | 8.50E+06 | 7.00E+06 | 3.57E+01 | 1.5 |
| 1798 | 3.50E+08 | 3.40E+05 | 3.70E+05 | 3.55E+05 | 9.86E+02 | 3.0 |
| 1799 | 3.50E+08 | 5.00E+03 | 3.00E+04 | 1.75E+04 | 2.00E+04 | 4.3 |
| S1 | 8.50E+08 | 5.90E+05 | 7.00E+05 | 6.45E+05 | 1.32E+03 | 3.1 |
| S3 | 3.00E+08 | 1.60E+07 | 1.40E+07 | 1.50E+07 | 2.00E+01 | 1.3 |
| S5 | 1.50E+09 | 5.00E+05 | 2.90E+05 | 3.95E+05 | 3.80E+03 | 3.57 |

P307 and P307Ex were tested for activity against *A. baumannii* strain 1791, *E. coli*, *P. aeruginosa* strain PAO1, *S. aureus* strain RN4220, *S. aureus* strain 8325 and *B. anthracis*. As shown in Table 6, P307 and P307 were most active against *A. baumannii* and *B. anthracis*.

TABLE 6

P307 and P307Ex against other bacterial species.

| Sample | A. baumannii 1791 | E. coli | B. anthracis Δsterne | Pseudomonas aeruginosa PAO1 | S. aureus RN4220 | S. aureus 8325 |
|---|---|---|---|---|---|---|
| control 1 | 5.50E+08 | 5.50E+08 | 2.40E+07 | 1.30E+09 | 1.50E+09 | 6.50E+08 |
| control 2 | 2.60E+08 | 4.50E+08 | 2.80E+07 | 4.50E+08 | 7.50E+08 | 9.50E+08 |
| P307EX 1 | 1.10E+05 | 3.50E+08 | 2.60E+03 | 4.70E+07 | 5.20E+07 | 3.20E+07 |
| P307EX 2 | 3.90E+05 | 3.00E+08 | 2.90E+03 | 3.70E+07 | 5.80E+07 | 3.60E+07 |
| P307 1 | 5.80E+05 | 3.50E+08 | 3.10E+03 | 5.60E+07 | 8.00E+08 | 4.80E+07 |
| P307 2 | 3.70E+05 | 3.50E+08 | 4.00E+03 | 4.00E+07 | 4.50E+08 | 4.40E+07 |
| average control | 4.05E+08 | 5.00E+08 | 2.60E+07 | 8.75E+08 | 1.13E+09 | 8.00E+08 |
| average P307EX | 2.50E+05 | 3.25E+08 | 2.75E+03 | 4.20E+07 | 5.50E+07 | 3.40E+07 |
| average P307 | 4.75E+05 | 3.50E+08 | 3.55E+03 | 4.80E+07 | 6.25E+08 | 4.60E+07 |
| difference P307EX | 1.62E+03 | 1.54E+00 | 9.45E+03 | 2.08E+01 | 2.05E+01 | 2.35E+01 |
| difference P307 | 8.53E+02 | 1.43E+00 | 7.32E+03 | 1.82E+01 | 1.80E+00 | 1.74E+01 |
| log drop P307EX | 3.2 | 0.2 | 4.0 | 1.3 | 1.3 | 1.4 |
| log drop P307 | 2.9 | 0.2 | 3.9 | 1.3 | 0.3 | 1.2 |

Example 9

P307 is not Toxic to B Cells or Red Blood Cells.

P307 was mixed with red blood cells to determine if it would cause lysis. No lysis was observed at 200 µg of P307. When P307 was tested for lysis of a B cell line it was found to have only a slight effect on cell number after 24 hours. The results are shown in Table 7.

TABLE 7

(% viable)

| Sample | 0 min | 5 min | 30 min | 1 hour | 2 hour | 3 hour | 24 hours |
|---|---|---|---|---|---|---|---|
| Initial cell only | 97% | | | 83.60% | | 85% | 88.20% |
| Tris-HCl pH = 6.8 | | 97.20% | 89.70% | 94.70% | 81.50% | 90.90% | 89.90% |
| 200 µg P307 | | 94.60% | 1100% | 71.40% | 71.90% | 58.60% | 76.30% |
| 20 µg P307 | | 97.20% | 88.60% | 89.70% | 90.30% | 91.00% | 94.20% |
| 2 µg P307 | | 95.20% | 76.90% | 89.30% | 92.50% | 93.80% | 96.30% |

The peptides used in Examples 10-20 were chemically synthesized.

Peptides were created using a Protein Technologies Symphony™ peptide synthesizer (PTI Tucson, Ariz., USA) on pre-coupled Wang (p-alkoxy-benzyl alcohol) resin (Bachem, Torrance, Calif., USA). Reaction vessels were loaded at 25 µM and peptides were elongated using Fmoc protected amino acids (Anaspec, San Jose, Calif., USA) (1997. Standard Fmoc protocols. 289:44-67). Deprotection of the amine was accomplished with 20% piperidine (Sigma-Aldrich) in NMP (N-methylpyrrolidinone). Repetitive coupling reactions were conducted using 0.6 M HATU/Cl-HOBT (azabenzotriazol tetramethyluronium hexafluorophosphate/6-chloro-1-hydroxybenzotriazole) (P3 Biosystems, Shelbyville, Ky., USA) and 0.4 M NMM (N-methylmorpholine) using NMP (EMD) as the primary solvent (1989. New Coupling Reagents in Peptide Chemistry 30:1927-1930.). Resin cleavage and side-chain deprotection were achieved by transferring to a 100 ml round bottom flask and reacted with 4.0 ml concentrated, sequencing grade, trifluoracetic acid (Fisher) with triisopropylsilane (Fluka), degassed water, and 3,6-dioxa-1,8-octanedithiol (DODT, Sigma-Aldrich) in a ratio of 95:2:2:1 over a 6 hour time frame. This was followed by column filtration to a 50 ml round bottom flask and TFA volume reduced to 2 ml using a rotary evaporator. A standard ether precipitation was performed on the individual peptides by transferring to a 50 ml falcon tube containing 40 ml cold tert-butyl methyl ether (TBME, Sigma-Aldrich). Samples were placed in an ice bath for 2 hours to aid precipitation followed by pellet formation using centrifugation (3300 rpm, 5 min). Excess ether was removed by vacuum aspiration and the peptide pellets were allowed to dry overnight in a fume hood. Dried peptide pellets were resolved in 20% acetonitrile and 10 ml HPLC grade water, subsampled for LC/MS and lyophilized. All crude products were subsequently analyzed by reverse-phase Aquity™ UPLC (Waters Chromatography, Milford, Mass., USA) using a Waters BEH C18 column. Individual peptide integrity was verified by tandem electrospray mass spectrometry using a ThermoFinnigan LTQ™ (Thermo Fisher, Waltham, Mass., USA) spectrometer system. Preparative chromatography was accomplished on a Vydac C18 RP preparative column on a Waters 600 Prep HPLC. Individual fractions were collected in 30 seconds intervals, characterized using LC/MS and fractions containing desired product were lyophilized. These were stored at −20° C. until being resuspended in autoclaved Milli-Q water for various assays. The stock solutions were then stored at 4° C. The peptides are summarized with their amino acid sequences, isoelectric points (pI) and molecular weights (MW) in table 8.

to below the limit of detection (<10 cfu/mL). P307 was slightly more active than P307AE-8, but both peptides induced about a 3.8-log-unit decrease in viable bacteria (FIG. 2A). To investigate how the eight amino acids, SQSRESQC, contributed to the higher activity of P307SQ-8C, the same molar concentration of peptide SQSRESQC as 50 μg/mL P307 was added by itself or in combination with P307 to A. baumannii strains #1791 and S5. The activities were compared with 50 μg/mL of P307 and P307SQ-8C. The combination was only as active as P307 while SQSRESQC peptide alone has no activity (FIG. 2B). Hence the linkage is essential for the high bactericidal activity of P307SQ-8C. Next, we investigated the importance of sequence and composition. By scrambling the last eight amino acids in P307SQ-8C, we synthesized P307CS-8 with a C-terminal addition of CSQRQSES to P307. The activities of P307SQ-8C and P307CS-8 were comparable (FIG. 2C). The error bars show standard deviation and the black horizontal line marks the limit of detection. Thus, we concluded that the superior activity of P307SQ-8C derives from the composition of the last eight amino acids, regardless of the order of the last eight amino acids. For further investigation, we used P307SQ-8C because it is the most active, and compared its activity with P307.

Example 11

Bactericidal Activities of P307 and P307SQ-8C

The effects of pH and NaCl on the in vitro activities of P307 and P307SQ-8C were investigated. A. baumannii strain #1791 were treated with 50 μg/mL of peptides to test each condition. Two buffer systems (sodium phosphate and Tris-HCl) were used to test pH 6.8, 7.5, 8.0 and 8.8. The peptides were more active in Tris-HCl and higher pH elicited better killing (FIG. 13A). Thus, we elected to continue our in vitro experiments with 50 mM Tris-HCl, pH 7.5, which approximates physiological pH. The activities of both peptides were inversely proportional to the concentra-

TABLE 8

| Names | Amino acid sequences | pI | MW | SEQ ID NO: |
|---|---|---|---|---|
| F307 | | 10.12 | 16 kDa | 1 |
| P307 | NAKDYKGAAAEFPKWNKAGGRVLAGLVKRRK | 10.71 | 3.4 kDa | 43 |
| P307AE-8 | NAKDYKGAAAEFPKWNKAGGRVLAGLVKRRKAEMELFLK | 10.21 | 4.4 kDa | 49 |
| P307SQ-8C | NAKDYKGAAAEFPKWNKAGGRVLAGLVKRRKSQSRESQC | 10.38 | 4.3 kDa | 45 |
| P307C5-8 | NAKDYKGAAAEFPKWNKAGGRVLAGLVKRRKCSQRQSES | 10.38 | 4.3 kDa | 51 |
| P307SQ-8A | NAKDYKGAAAEFPKWNKAGGRVLAGLVKRRKSQSRESQA | 10.69 | 4.3 kDa | 53 |

Example 10

Comparison of In Vitro Bactericidal Activities of Peptides of the Present Disclosure.

To determine the in vitro bactericidal activities of the peptides, P307, P307AE-8, P307SQ-8C, and P307CS-8, bacteria were treated with the peptides for 2 hours at room temperature. The survived cells were serially diluted and plated on TSB agar plates to determine the activity.

The bactericidal activities of 50 μg/mL the peptides, P307, P307AE-8 and P307SQ-8C were compared by treating A. baumannii strains #1791, S5 and ATCC17978. P307SQ-8C was the most active, reducing about $10^6$ cfu/mL of bacteria tion of NaCl (FIG. 13B). Next, titration of P307 and killing kinetics of P307 and P307SQ-8C were investigated by treating A. baumannii strain #1791. The activity of P307 was concentration-dependent, beginning from 4 μg/mL (FIG. 13C). P307SQ-8C acted faster than P307, resulting in about 3.2-log-unit decrease already at the 5 minute time point (FIG. 13D). There was no difference in activities of either peptide at room temperature or 37° C. (data not shown). From these in vitro characterization experiments, we decided our optimal experimental conditions to be 50 mM Tris-HCl, pH 7.5, 50 μg/mL peptides and 2 hours at room temperature (22-25° C.), unless otherwise indicated.

Example 12

Figure 14:
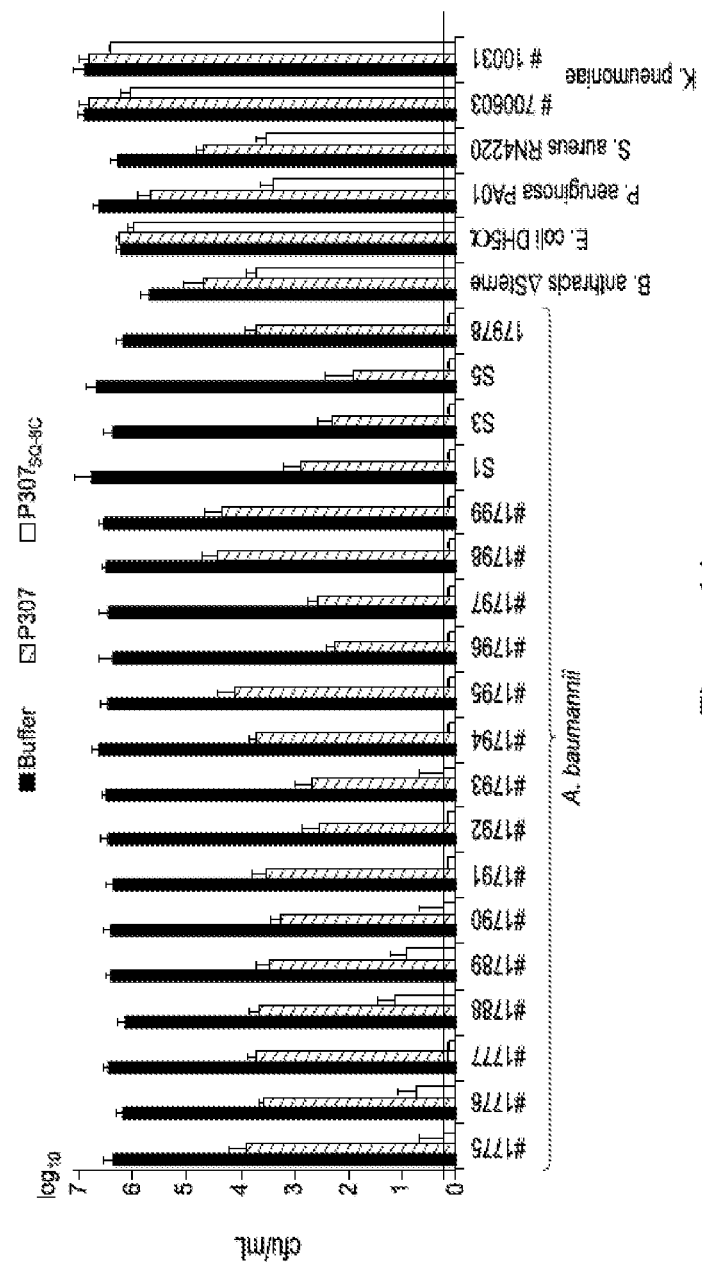
FIG. 14. Is a graph showing the sensitivity of different bacterial species to P307 and P307SQ-8C. The error bars show standard deviation and the black horizontal line marks the limit of detection.

Next, we investigated the in vitro bactericidal spectra of P307 and P307SQ-8C against different bacterial species, *A. baumannii* (strain Nos. 1775, 1776, 1777, 1788, 1789, 1790, 1791, 1792, 1793, 1794, 1796, 1797, 1798, 1799, ATCC 17978 and S1, S3, D5), *Bacillus anthracis* (ΔSterne), *Escherichia coli* (DH5α), *Pseudomonas aeruginosa* (PA01), *Staphylococcus aureus* (RN4220) and two strains of *Klebsiella pneumonia* (ATCC 700603 and ATCC10031). These bacterial species were treated with 50 μg/mL of P307 or P307SQ-8C in 50 mM Tris-HCl, pH 7.5 for 2 hours at room temperature to investigate the specificity of the peptides. Among the bacteria tested, *A. baumannii* strains were consistently most sensitive to the peptides, showing an average of 2.7- and 6.2-log-unit decrease with P307 and P307SQ-8C, respectively. *Bacillus anthracis, Pseudomonas aeruginosa* and *Staphylococcus aureus* are moderately sensitive. P307 and P307SQ-8C produced an average of about 1.3- and 2.9-log unit decrease, respectively, for these bacteria. However, *Escherichia coli* and *Klebsiella pneumoniae* are resistant to both peptides (FIG. 14).

performed a minimal inhibitory concentration assay for two *A. baumannii* strains, #1791 and ATCC17978. Microtiter dilution method was used to determine the MICs of levofloxacin, ceftazidime, polymyxin B, P307 and P307SQ-8C for *A. baumannii* strains #1791, #1798, S5 and ATCC17978. For the antibiotics, 1.5-2 fold serial dilutions (three lower and three higher) of the MICs determined by Etest Lood R, et al., 2015 Antimicrob. Agents Chemother. 59:1983-1991) were included. For the peptides, two-fold serial dilutions (500-31.25 μg/mL) were tested. The overnight cultures were re-suspended to $OD_{600}$ of 0.001 (about $10^5$ cfu/mL) in Mueller-Hinton broth (pH 7.9). The antibiotics or peptides were added to final 100 μL for each dilution. The bacteria were allowed to grow at 37° C. for 24 hour at 220 rpm. The absorbance at 595 nm was then read in a SpectraMax Plus Reader (Molecular Devices). The MICs were determined as the lowest concentrations of antimicrobial agents that completely inhibit bacterial growth. Alamar®Blue was used to confirm the data obtained from $OD_{595}$. The experiments were conducted at least twice in duplicate.

The strains displayed varying degree of sensitivity to all antimicrobial agents (Table 9).

TABLE 9

| *A. baumannii* strains | Levofloxacin | | Ceftazidime | | Polymyxin B | | P307 | | P307SQ-8C | |
|---|---|---|---|---|---|---|---|---|---|---|
| | μg/mL | μM | μg/mL | μM | μg/mL | μM | μg/mL | μM | μg/mL | μM |
| #1791 | 6 | 16.6 | 250 | 457 | 0.25 | 0.19 | 375 | 110 | 125 | 29 |
| ATCC17978 | ≤0.1 | 0.3 | 12 | 21.9 | 0.25 | 0.19 | 750 | 220 | ≤500 | ≤116 |

Example 13

Figures 15A, 15B:
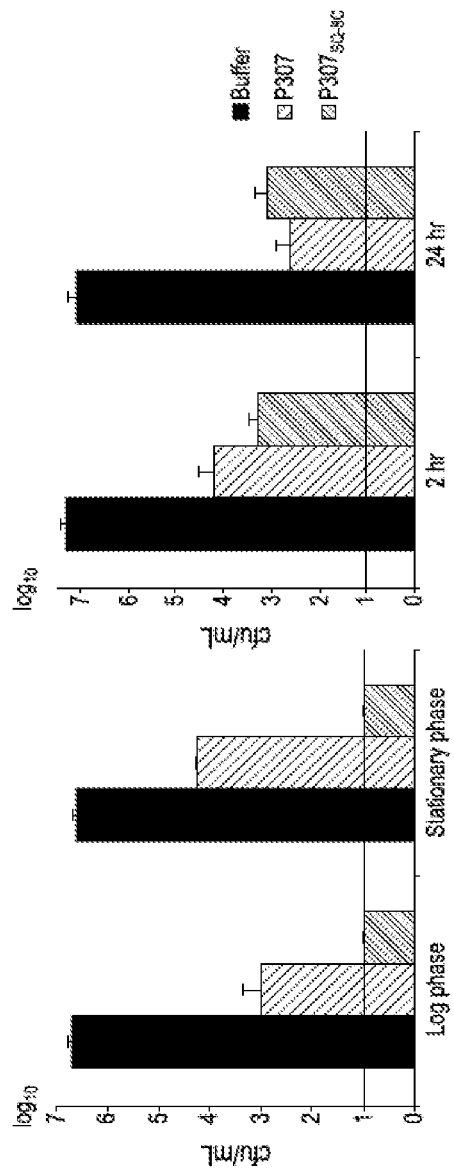
FIGS. 15A and 15B are graphs that show the bactericidal activities of P307 and P307SQ-8C against the log phase and stationary phase of *A. baumannii* strain No. 1791 (15A) and the biofilm phase (15B).

In addition, to investigate the activities of the peptides against *A. baumannii* at different growth phases, we compared the sensitivities of strain #1791 at log phase, stationary phase and biofilm state. The bacteria in log phase (3 hours post inoculation of 1:100 overnight culture in fresh media) and stationary phase (overnight culture) were treated with 50 μg/mL of P307 or P307SQ-8C for 2 hours at room temperature. The survived cells were serially diluted and plated on TSB agar plates to determine cfu/mL. (FIG. 15A). *A. baumannii* biofilms were established by incubating about $10^5$ cfu/mL of strain #1791 in TSB with 0.2% glucose inside about 2.5 cm long catheters for 72 hours at 37° C. The catheters were then washed to remove planktonic cells and treated with 250 μg/mL of P307 or P307SQ-8C. After 2 hours and 24 hours at room temperature, the biofilm was thoroughly disrupted and survived cells re-suspended to be plated and counted to determine the killing efficiency of the peptides against in vitro biofilm (FIG. 15B) The log phase organisms were slightly more sensitive to P307 than stationary phase (about 3.7—versus 2.4-log-unit decrease). There seems to be no such difference with P307SQ-8C (FIG. 15A). The biofilms were the most resistant of all growth phases. Biofilms were treated with 250 μg/mL P307 or P307SQ-8C for 2 or 24 hr. After 2 hours, about 3- and 4-log-unit decrease in cfu/mL was observed with P307 and P307SQ-8C, respectively. After 24 hours, P307 produced an additional about 1.3-log-unit decrease while P307SQ-8C did not (FIG. 15B).

Example 14

Figure 2:
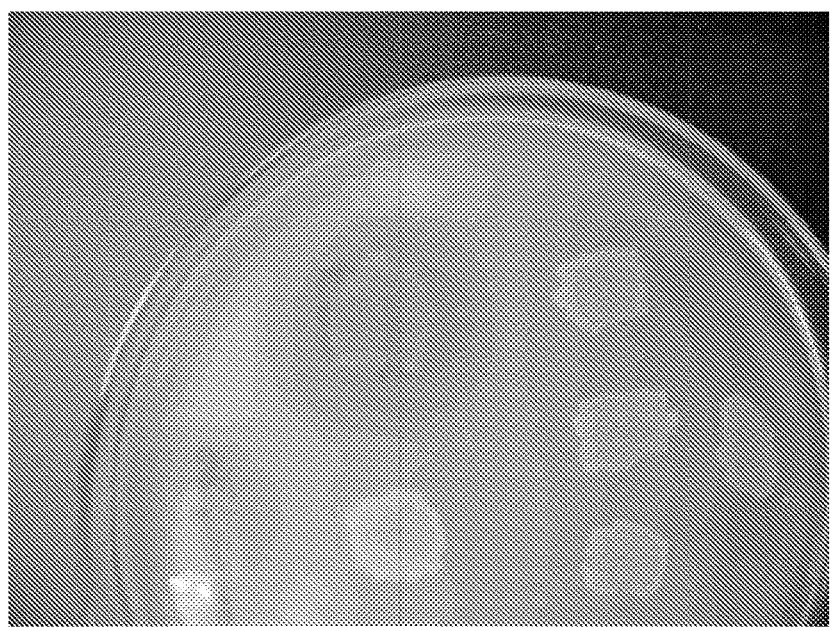
FIG. 2. A representative image of lysin clone activity in clearing live *A. baumannii* imbedded in the agar.
Figure 3:
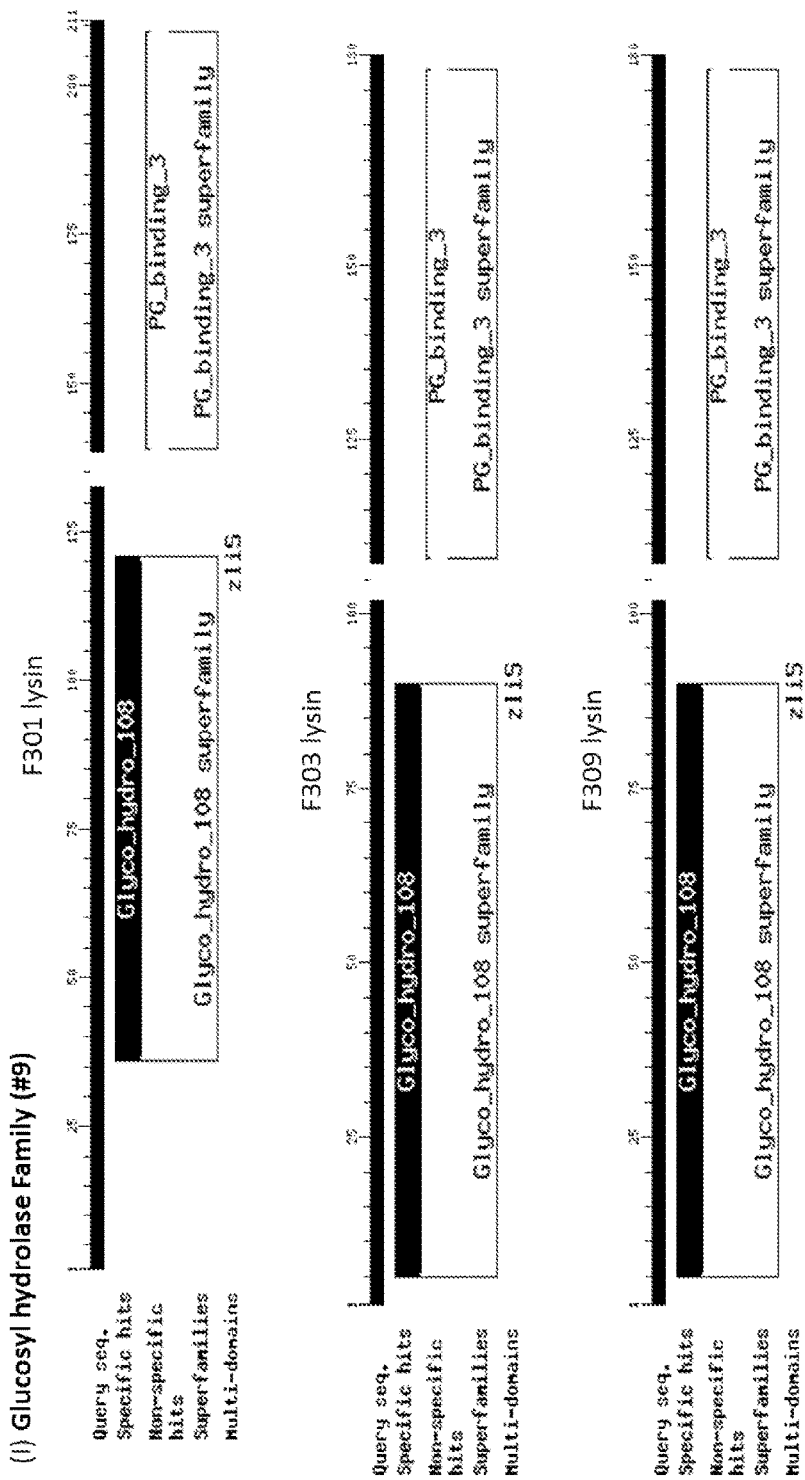
FIG. 3. Schematic of amino acid sequences of cloned lysins showing four classes of lytic activity: i) glycosyl hydrolase family, ii) phage baseplate lysozymes, iii) lysozyme autolysins, and iv) lysins.
Figure 3:
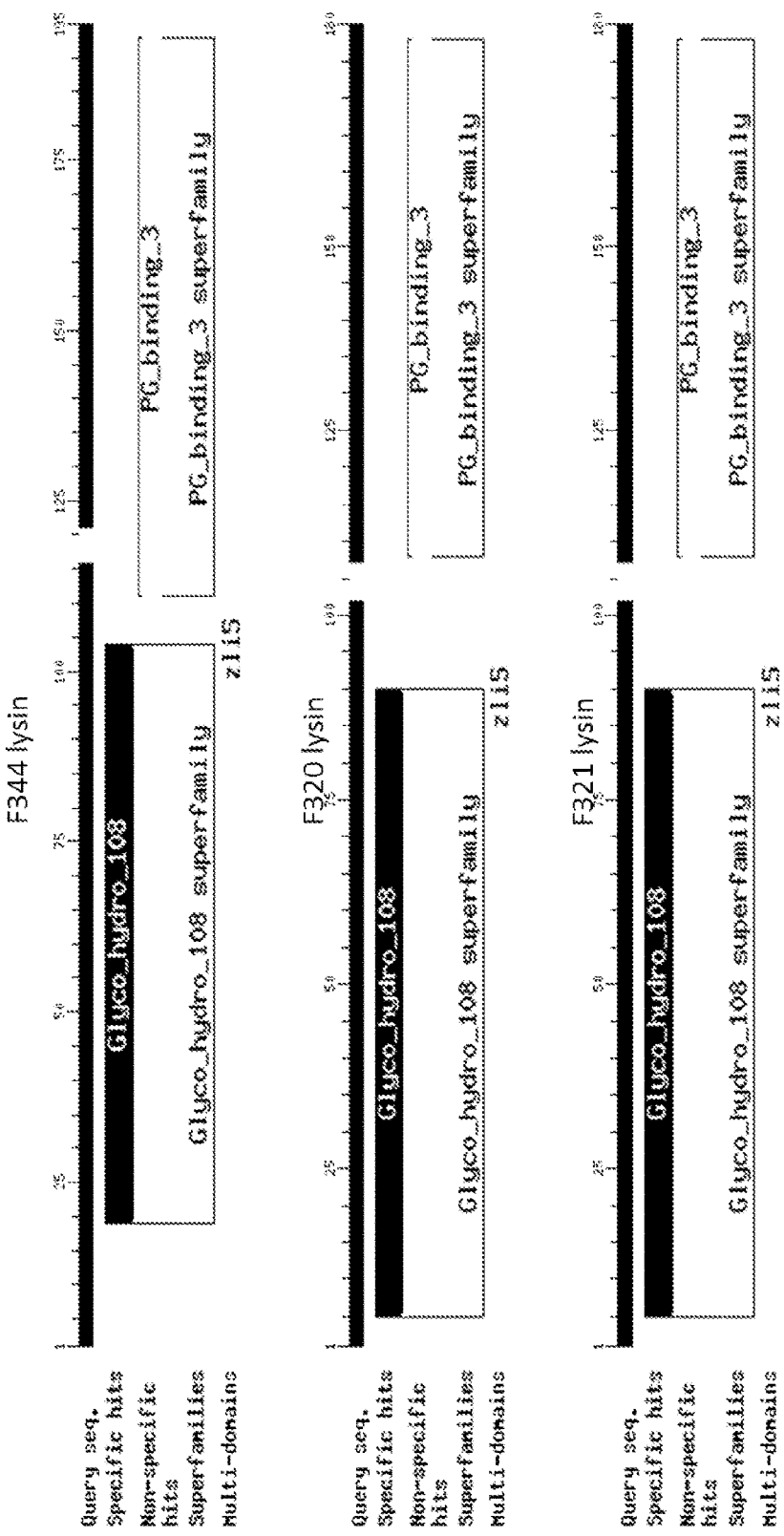
Figure 3:
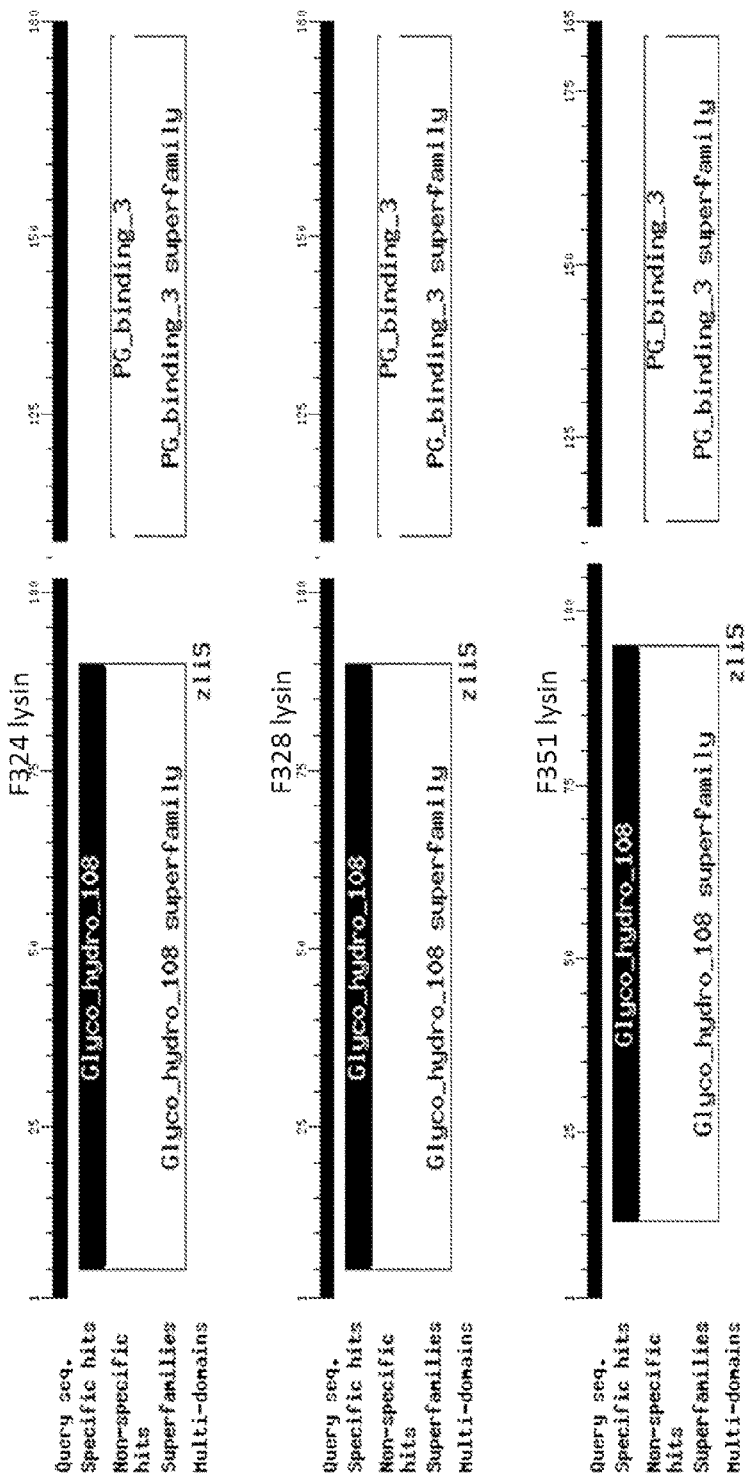
Figure 3:
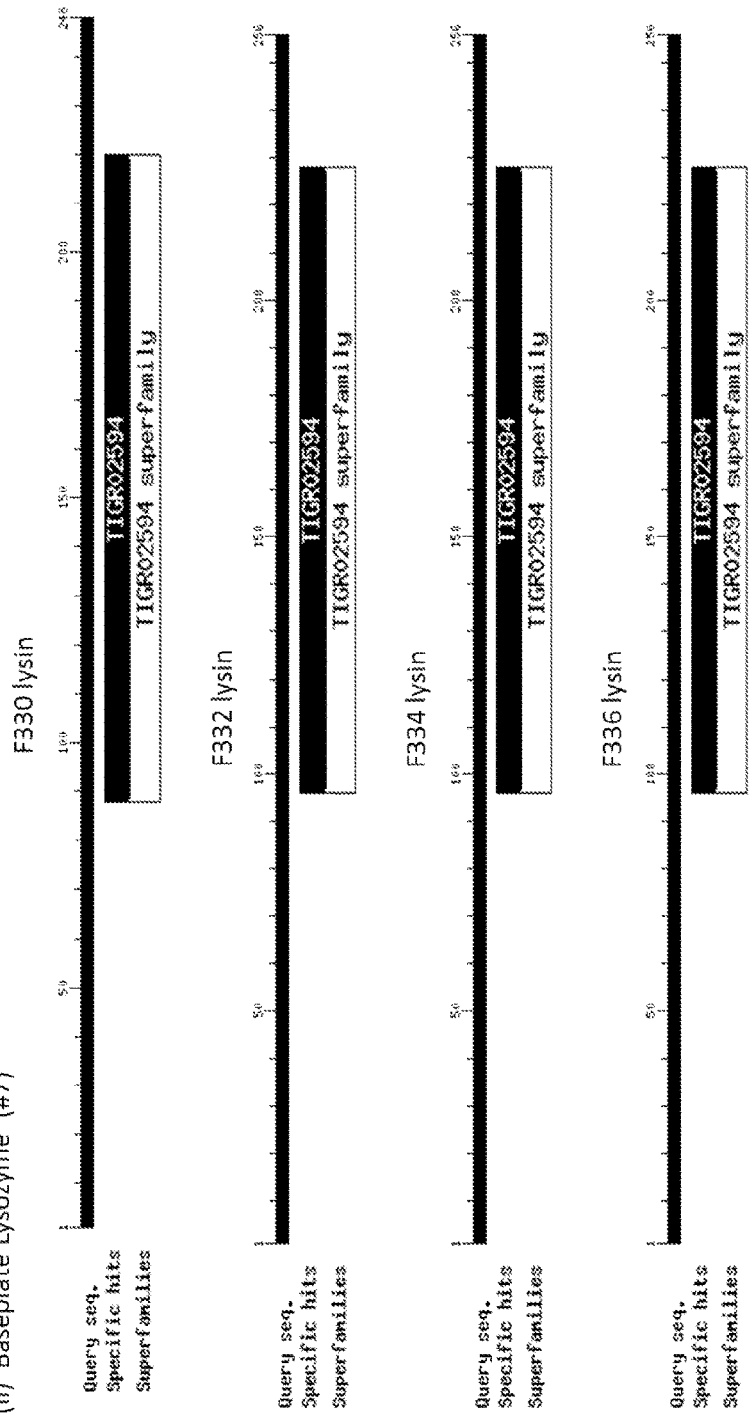
Figure 3:
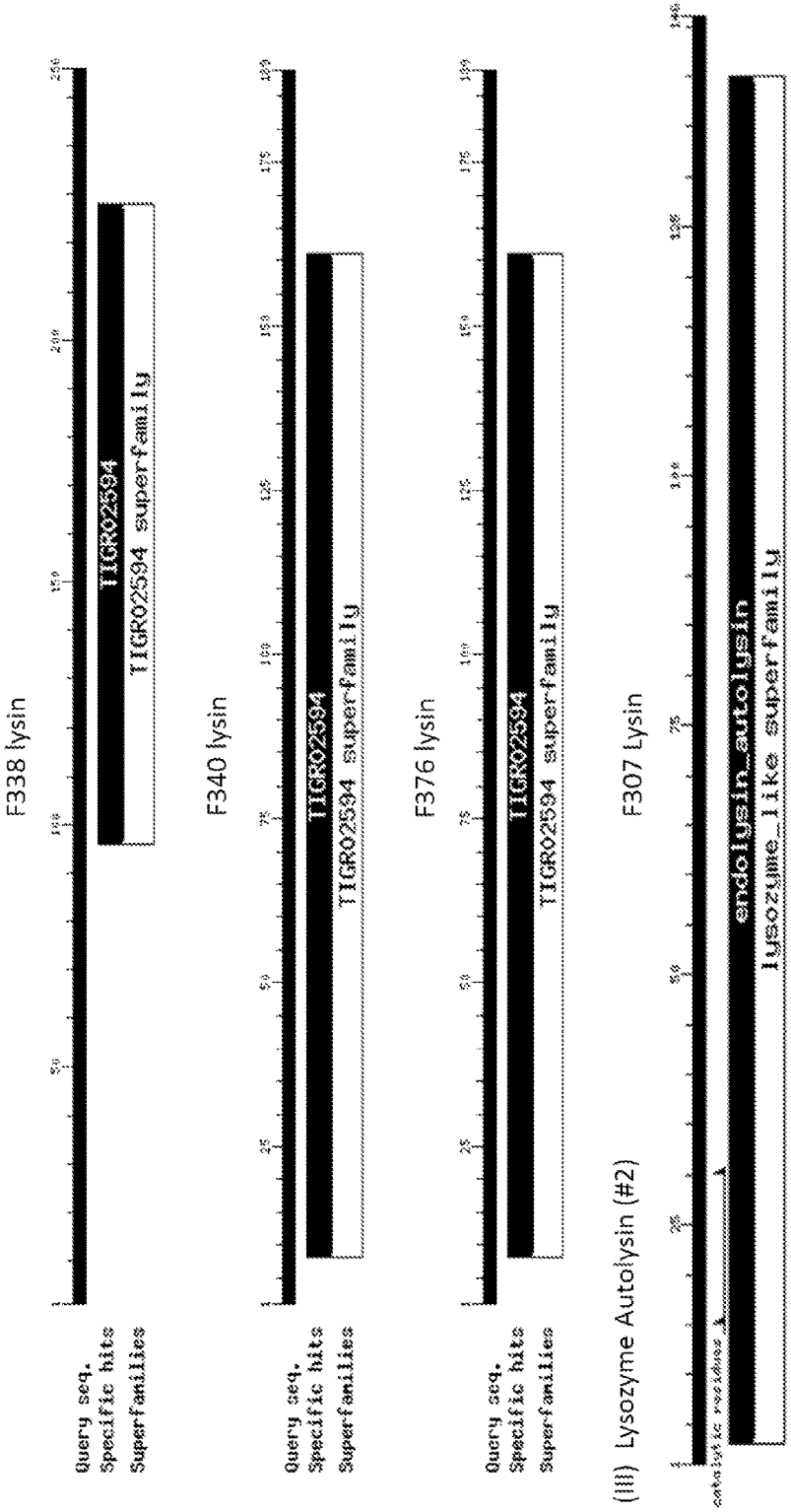
Figure 3:
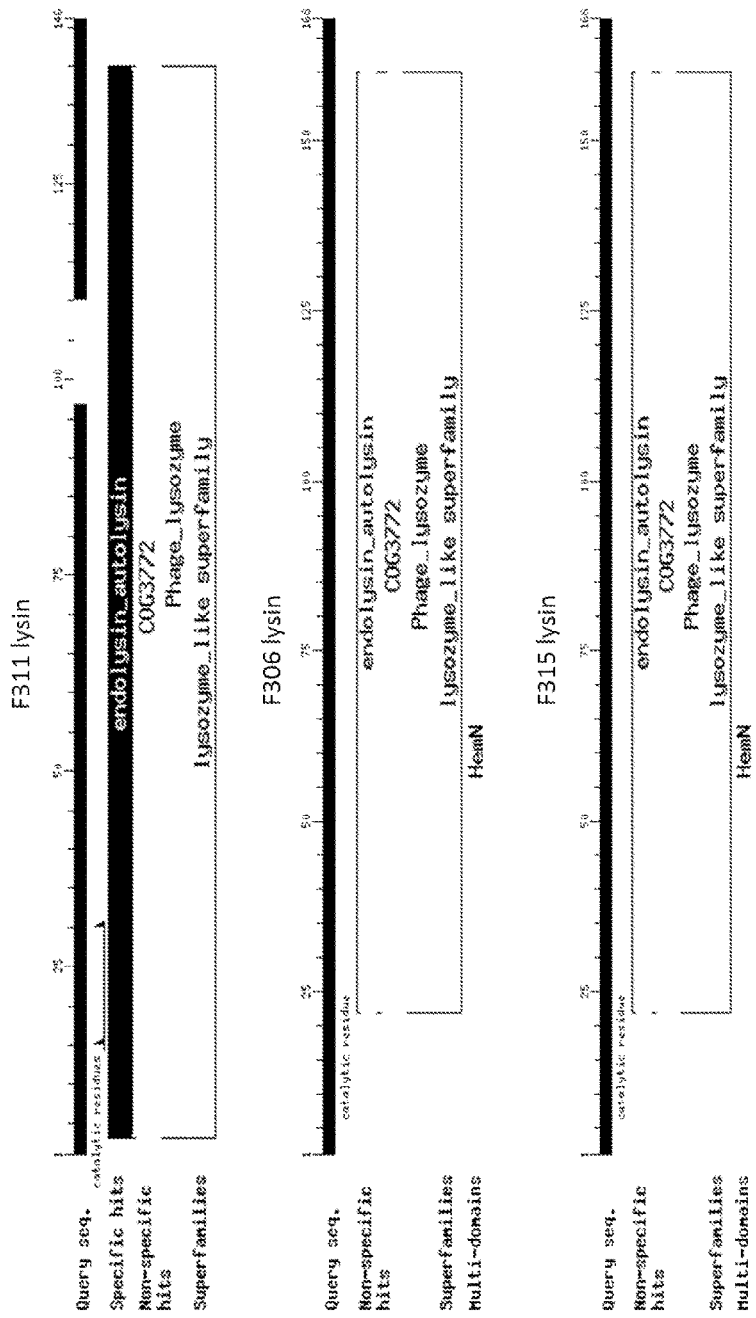
Figure 3:
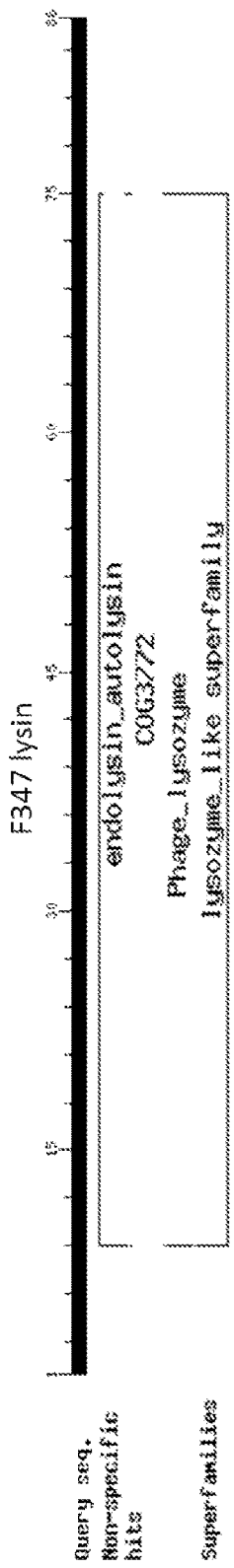
Figure 6:
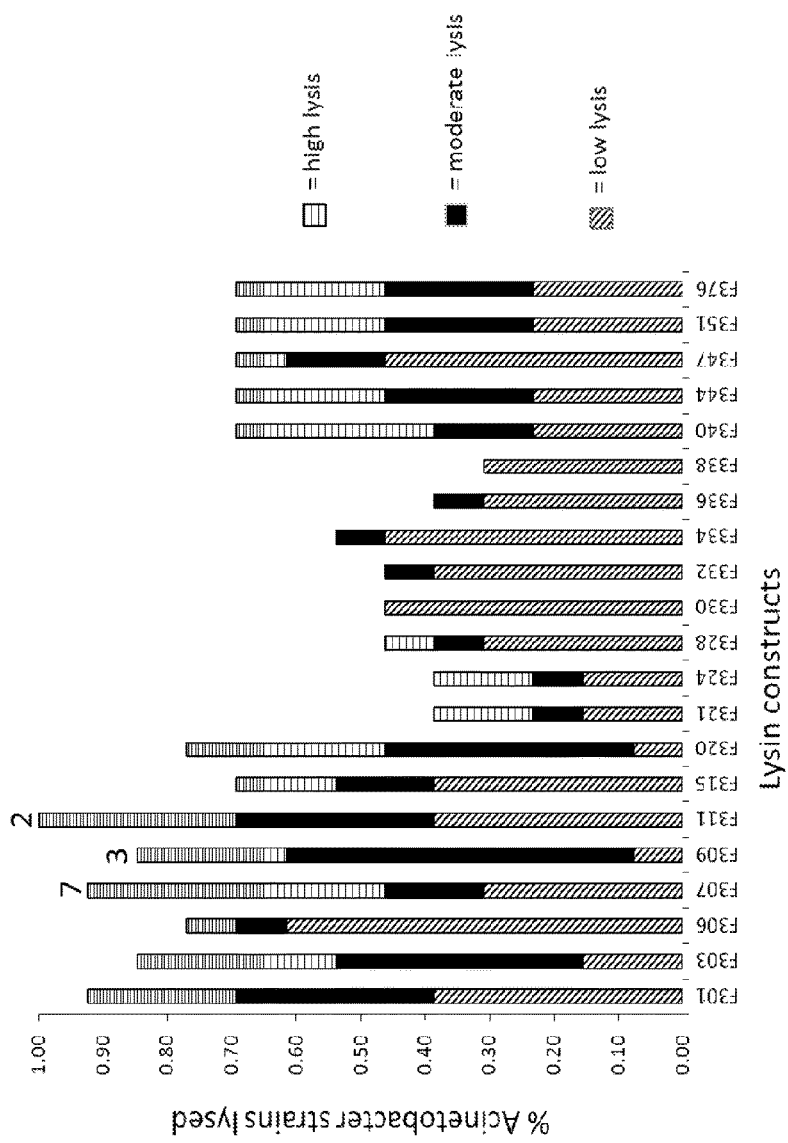
FIG. 6. Is a graph showing the lytic activity of 21 cloned constructs against thirteen. different *A. baumannii* clinical isolates.
Figure 7A:
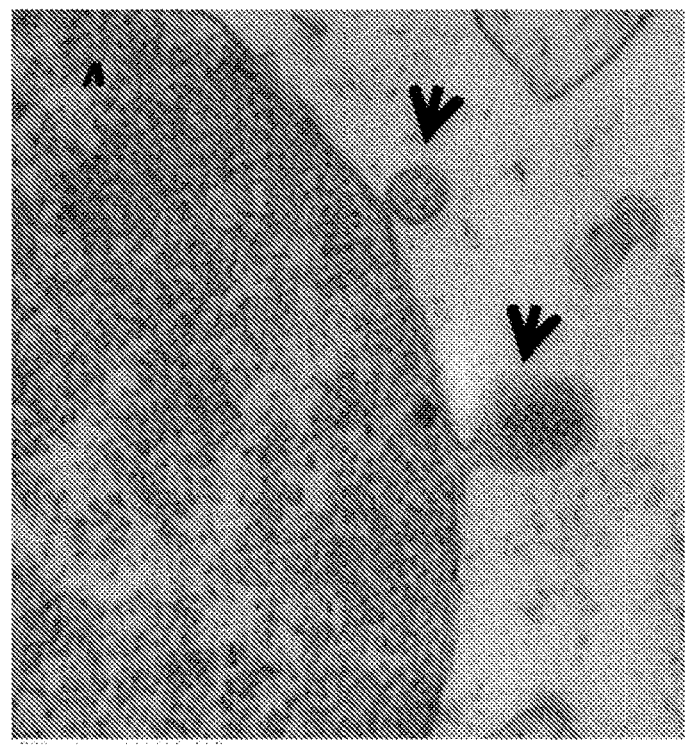
FIGS. 7A, and 7B. Blebbing of the cytoplasmic membrane containing cytosolic contents from *A. baumannii* cells are observed after treatment with F307 (arrows).
Figure 7B:
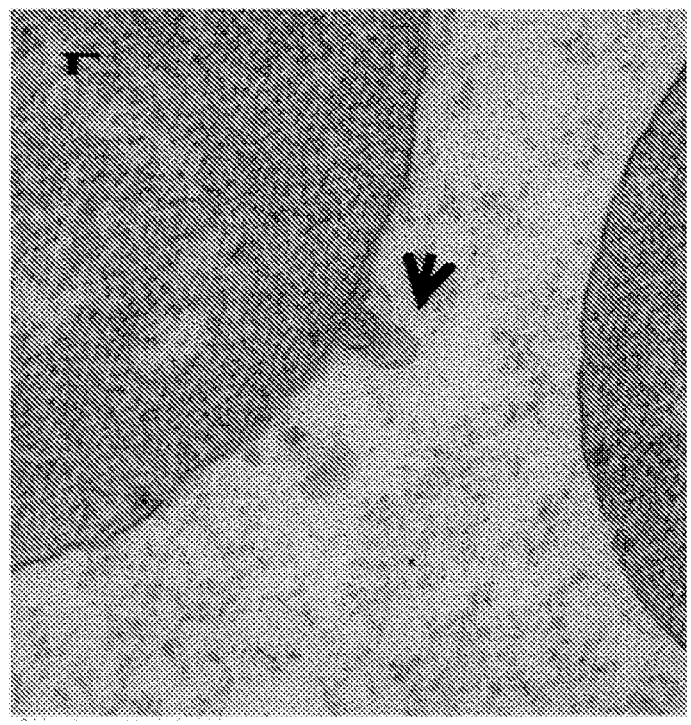

In order to compare the efficiency of the peptides P307 and P307SQ-8C with some clinically used antibiotics, we P307SQ-8C has a lower MIC than P307, which is in accordance with the in vitro killing activity (FIGS. 2 and 3).

Example 15

Cytotoxic Effects of P307 and P307SQ-8C as Measured by B Cell Survival and Hemolysis.

Human B-cells obtained from a rheumatic fever patient at The Rockefeller University Hospital were grown in RPMI media supplemented with 10% bovine serum, penicillin and streptomycin. Cells were harvested by low speed centrifugation, washed once in media, and resuspended in pre-warmed media to a concentration of $10^7$ cells/ml, as determined by trypan blue exclusion tests. The peptides (P307, P307SQ-8C and melittin) were serially diluted (80-0.3125 μM) in culture media, and added to $5\times10^4$ live cells. Cells were incubated for 1 hour at 37° C. in a humidified 5% $CO_2$ atmosphere, after which they were stained (CellTiter 96 Non-radioactive cell proliferation assay; Promega) according to manufacturer's instructions. The samples were incubated for additionally 4 hours, before a Solubilization/Stop solution was added, and incubated overnight. The absorbance at 570 nm was measured in SpectraMax Plus Reader (Molecular Devices). The reactions were carried out twice in triplicate and representative data are shown as mean±standard deviation.

Human blood from a healthy individual was gathered in an EDTA-tube, and red blood cells (RBC) collected through low speed centrifugation. Cells were washed in PBS, and resuspended to a 10% RBC solution. P307 and P307SQ-8C were serially diluted in PBS (80-0.3125 μM). PBS and 1% Triton X-100 were used as negative and positive controls, respectively. Samples were mixed, and incubated for 1 hour at 37° C. The supernatant was collected, and absorbance at 405 nm recorded through SpectraMax Plus Reader (Molecular Devices). The reactions were carried out twice in triplicate and representative data are shown as mean±standard deviation.

Serial dilutions of peptides were incubated with about $5 \times 10^4$ live B cells for 1 hr at 37° C. in a humidified 5% $CO_2$ atmosphere, and melittin was used as a positive control. CellTiter 96® Non-Radioactive Cell Proliferation Assay (Promega) was conducted according to manufacturer's protocol to quantify the survival of B cells. Red blood cells (RBCs) were incubated with serial dilutions of the peptides and the release of hemoglobin into the supernatant was measured by $OD_{405}$ to determine hemolysis. Triton X-100 was used as a positive control. The error bars show standard deviation.

The peptides were tested for their cytotoxicity using human B cells and red blood cells (RBCs). In contrast to the melittin positive control, the membranes of B cells are not affected by either P307 or P307SQ-8C. Even at the highest concentration tested (80 µM), the viability of the cells remains the same as the buffer control (FIG. 16A). Similarly, the integrity of RBCs are also not affected by either peptide in comparison to the Triton X-100 positive control (FIG. 16B).

Example 16

Figure 17B:
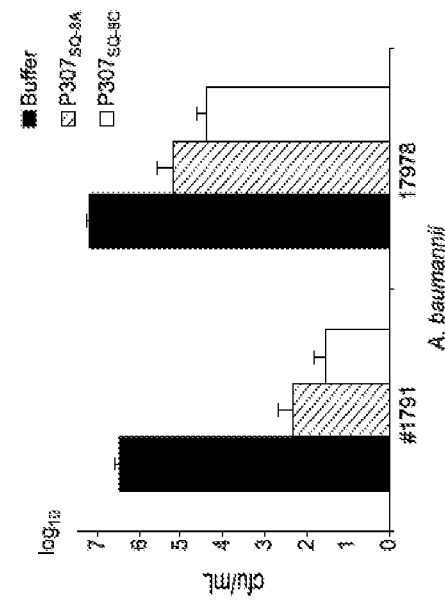
FIG. 17.
FIG. 17A shows the effect of DTT at 0, 0.1 and 1 mM on the activity of P307 and P307SQ-8C.
Figure 17A:
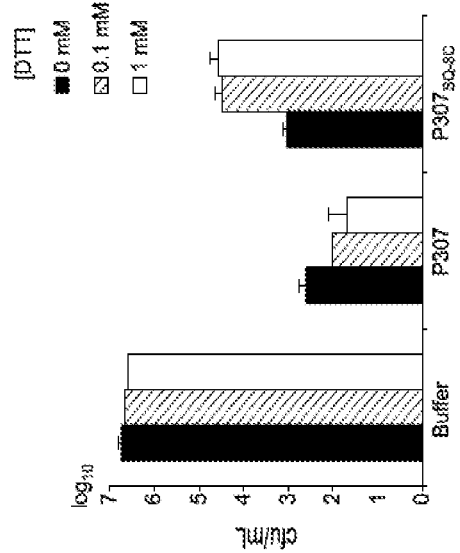

A portion of P307SQ-8C (about 25%) runs at twice the theoretical molecular weight in comparison to P307SQ-8A, which runs at 4.3 kD (data not shown). To determine the importance of disulfide bond formation for the high activity of P307SQ-8C the bactericidal activities of P307 and P307SQ-8C were compared in the presence of 0, 0.1 and 1 mM dithiothreitol (DTT). *A. baumannii* strain #1791 was treated with 50 µg/mL P307 or 10 µg/mL P307SQ-8C in 50 mM Tris-HCl, pH 7.5 for 2 hours at room temperature. The survived cells were serially diluted and plated on TSB agar. P307SQ-8C becomes less active with higher DTT concentration whereas the activity of P307 slightly increases (FIG. 17A). To further confirm the importance of disulfide formation for P307SQ-8C activity, we synthesized P307SQ-8A with the last cysteine changed to alanine. *A. baumannii* strains no. 1791 and ATCC17978 were treated with 10 µg/mL of each peptide. The bactericidal assays of P307SQ-8C and P307SQ-8A showed that the former is slightly more active than the latter (FIG. 17B). These results altogether pointed out that part of the superior activity of P307SQ-8C derives from disulfide bond formation between two molecules.

Example 17

Figure 18:
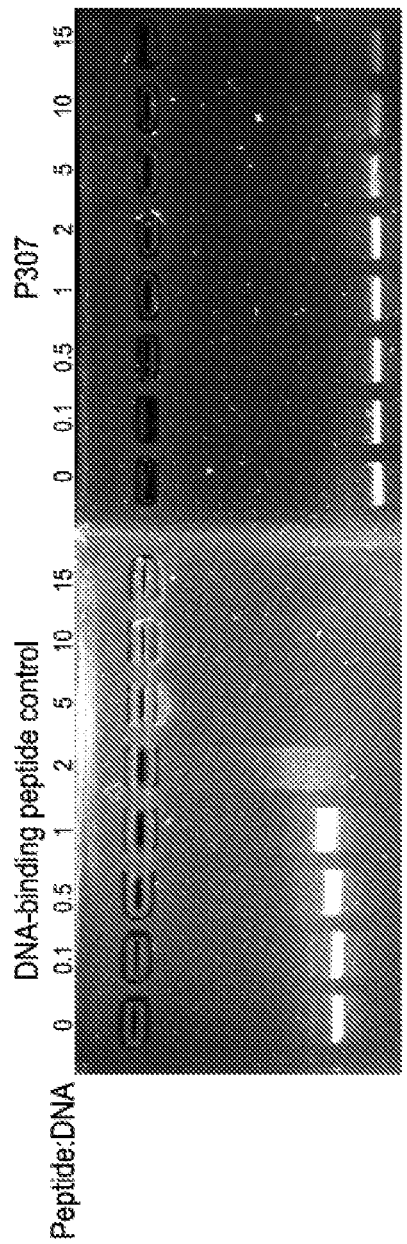
FIG. 18. Is a DNA shift gel showing the shift for control peptide and P307.

Next, we investigated whether P307 binds to DNA, given the positive charges on the peptides (net charge of +7). The peptide P307 was mixed with DNA at different peptide:DNA ratios (0:1-15:1) and incubated for 1 hour before being analyzed on an agarose gel. In comparison to positive control peptide, no shift in molecular weight was observed for P307 at any of the ratios of peptide to DNA tested (FIG. 18).

Example 18

Because the peptides did not appear to kill the bacteria by interacting with DNA, we investigated whether they affect the bacterial membrane using transmission electron microscopy (TEM). *A. baumannii* strain #1791 was treated with buffer (control) or 300 µg/mL P307SQ-8C for 5 minutes or 2 hours. Comparing the TEM images of the samples reveals disruption of inner membrane and changes in intracellular density (FIGS. 19A, B and C). In addition, we found that the resistant bacteria at pH 7.5 (FIG. 3) were sensitive to P307 at pH 8.8, including *E. coli* and *K. pneumoniae* (FIG. 19D). Because the charges on the peptide do not vary as pH changes from 7.5 to 8.8, we reasoned that the changes occur on the bacterial membrane. At higher pH, the bacterial membrane becomes more negatively charged, allowing the positively charged peptides to establish stronger ionic interactions.

Example 19

Without wishes to be bound by theory, we hypothesize the following mechanism of action: P307SQ-8C interacts with the bacterial membrane to gain entry into the cell, and in the process, disrupts the cytoplasmic membrane. Membrane permeabilization is more effective when the peptide is dimerized. The disruption induces the production of reactive oxygen species such as hydroxyl radicals, which disturbs the intracellular content. To investigate this hypothesis, we determined membrane disruption using SYTOX® Green uptake assay.

Overnight cultures of bacteria were washed in 50 mM Tris-HCl pH 7.5, and resuspended to an $OD_{600}$ of 0.3 (about $10^7$ cfu/ml). Benzonase® nuclease (25 U/ml)(Novagen) and SYTOX® Green (1 µM) (Invitrogen) was added to the bacterial cells, and incubated for 15 minutes at room temperature in the dark. Peptides were added (50 µg/ml; 14.7 µM P307 and 11.6 µM P307SQ-8C, and melittin (14.7 µM) (Sigma) was used as a control. Relative fluorescence units (RFU) were measured in a SpectraMax Plus reader (Molecular Devices) at room temperature (ex: 485 nm, em: 520 nm) for 2 hours. The reactions were carried out twice in duplicate and representative data are shown as mean±standard deviation.

Figure 20:
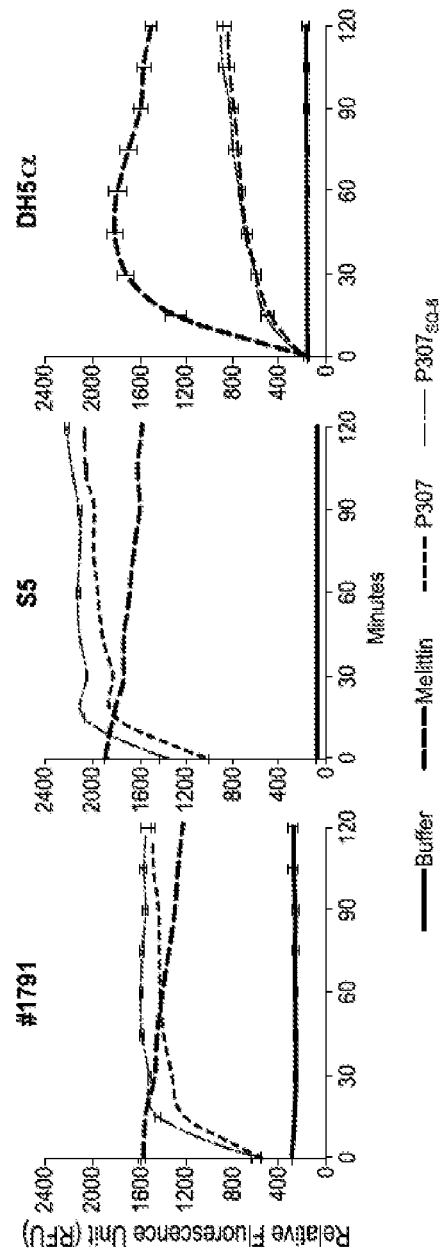
FIG. 20. Shows the membrane permeability of *A. baumannii* strains #1791 and S5 treated with P307 and P307SQ-8C.

Both peptides permeabilize the membranes of sensitive bacteria, giving rise to an increase in fluorescent signals of SYTOX® Green dye as it binds to intracellular DNA (FIG. 20). Hydroxyl radical formation was investigated by treating the bacteria with P307 and P307SQ-8C in the presence of hydroxyl radical scavenger, thiourea. Polymyxin B was included as a control since it has been reported that its bactericidal activity partially relies on hydroxyl radical death pathway. Thiourea (300 mM) inhibits the activity of P307 and P307SQ-8C completely (FIG. 21A). However, it cannot be disregarded that thiourea affects the activities by other pathways. Therefore, bactericidal activities were also compared under aerobic and anaerobic conditions. Since *A. baumannii* is a strictly aerobic bacteria, *E. coli* was used for the bactericidal assay with 50 mM Tris-HCl, pH 8.8. Both peptide activities were completely inhibited by anaerobic condition (FIG. 21B). Although we cannot rule out other possibilities such as effect on oxygen-dependent transport mechanism, the current results support our hypothesis of hydroxyl radical formation.

Example 20

Figure 22:
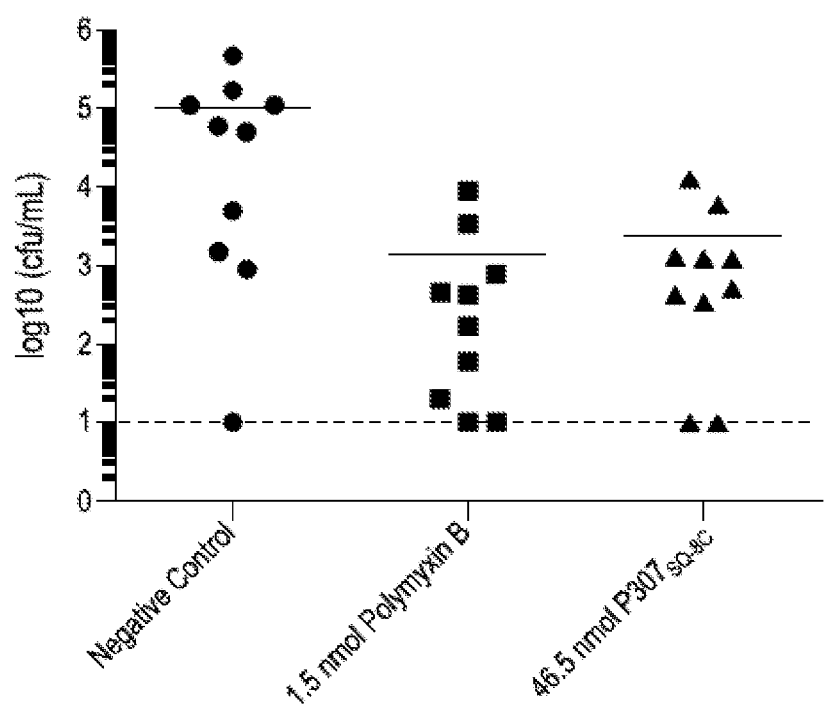
FIG. 22. Shows the effect of treatment of a skin infection with polymyxin B and P307SQ-8C.

We investigated the in vivo activity of P307SQ-8C using mouse skin model because skin infection is a common route of disease by *A. baumannii*. The backs of 40 female CD-1 mice (6 to 8 weeks of age; Charles River Laboratories) were shaved with an electric razor. Nair™ (Hair remover lotion for body and legs, aloe and lanolin) was applied to the shaved areas to remove any remaining hair. The areas were then disinfected with alcohol wipes, and skin abrasion was induced by tape-stripping. An area of ~1 cm² of the tape striped skin was then marked and infected with 10 μL of about $10^8$ cfu/mL A. baumannii strain no. 1791. The bacteria were allowed to colonize for 16-18 hours, after which the infected area was either left untreated or treated with 200 μg of P307SQ-8C or 2 μg of polymyxin B for 2 hours. To harvest the remaining bacteria on the skin, the mice were sacrificed and the infected skin was processed in 500 μL PBS for 1 minute in a Stomacher® 80 Biomaster using a microbag (Seward Ltd., UK). The solution was serially diluted and plated on LB agar containing 4 μg/mL levofloxacin and 12 μg/mL ampicillin for selection. The resulting cfu/mL from each animal is shown as a point and the horizontal bars represent the means. Both treatments reduce the bacterial load significantly (p-value=0.0023, ordinary one-way ANOVA) (FIG. 22).

---

What is claimed is:

1. A polypeptide, wherein the polypeptide comprises an amino acid sequence having the SEQ ID NO:1, SEQ ID NO:3, SEQ ID NO:6, SEQ ID NO:8, SEQ ID NO:13, SEQ ID NO:14, SEQ ID NO:15, SEQ ID NO:16, SEQ ID NO:20, or SEQ ID NO:21, and the polypeptide is conjugated to an antimicrobial peptide having the amino acid sequence SQS-RESQC (SEQ ID NO:44) to yield a conjugated polypeptide and the conjugated polypeptide has antibacterial activity.

2. The conjugated polypeptide according to claim 1, wherein the C-terminus of the polypeptide is conjugated to the antimicrobial peptide.

3. The conjugated polypeptide according claim 1, wherein the N-terminus of the polypeptide is conjugated to the antimicrobial peptide.

4. The conjugated polypeptide according to claim 1, wherein the conjugated polypeptide has antibacterial activity against a gram negative bacterium.

5. The conjugated polypeptide according to claim 1, wherein the C-terminus of the polypeptide is conjugated to the antimicrobial peptide or the N-terminus of the polypeptide is conjugated to the antimicrobial peptide.

6. The conjugated polypeptide according to claim 5, wherein the conjugated polypeptide has antibacterial activity against a gram negative bacterium.

7. A polypeptide, wherein the polypeptide comprises an amino acid sequence having the SEQ ID NO:1 or SEQ ID NO:21, or a fragment of the polypeptide consisting of the amino acid sequence of SEQ ID NO:43 (P307) and the polypeptide or polypeptide fragment is conjugated to an antimicrobial peptide having the amino acid sequence SQS-RESQC (SEQ ID NO:44) to yield a conjugated polypeptide and the conjugated polypeptide has antibacterial activity.

8. The conjugated polypeptide according to claim 7, wherein the C-terminus of the conjugated polypeptide is conjugated to the antimicrobial peptide.

9. The conjugated polypeptide according claim 7, wherein the N-terminus of the conjugated polypeptide is conjugated to the antimicrobial peptide.

10. The conjugated polypeptide according to claim 7, wherein the conjugated polypeptide has antibacterial activity against a gram negative bacterium.

11. The conjugated polypeptide according to claim 7, wherein the C-terminus of the polypeptide or fragment is conjugated to the antimicrobial peptide or the N-terminus of the polypeptide or fragment is conjugated to the antimicrobial peptide.

12. The conjugated polypeptide according to claim 7, wherein the conjugated polypeptide has antibacterial activity against a gram negative bacterium.

13. The polypeptide fragment of claim 7, wherein the conjugated polypeptide has the amino acid sequence of SEQ ID NO:45.

* * * * *